(12) United States Patent
Bulaj et al.

(10) Patent No.: US 8,933,020 B2
(45) Date of Patent: *Jan. 13, 2015

(54) METHODS AND COMPOSITIONS RELATED TO IMPROVING PROPERTIES OF PHARMACOLOGICAL AGENTS TARGETING NERVOUS SYSTEM

(71) Applicant: University of Utah Research Foundation, Salt Lake City, UT (US)

(72) Inventors: Grzegorz Bulaj, Salt Lake City, UT (US); H. Steve White, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/853,945

(22) Filed: Mar. 29, 2013

(65) Prior Publication Data

US 2013/0244947 A1 Sep. 19, 2013

Related U.S. Application Data

(63) Continuation of application No. 12/160,035, filed as application No. PCT/US2007/000261 on Jan. 5, 2007, now Pat. No. 8,435,940.

(60) Provisional application No. 60/757,047, filed on Jan. 5, 2006, provisional application No. 60/844,024, filed on Sep. 11, 2006.

(51) Int. Cl.
*A01N 37/18* (2006.01)
*C07K 1/00* (2006.01)
(Continued)

(52) U.S. Cl.
CPC .............. *C07K 7/08* (2013.01); *C07K 2319/01* (2013.01); *C07K 14/665* (2013.01); *C07K 5/1019* (2013.01); *C07K 14/57545* (2013.01); *C07K 14/6555* (2013.01); *C07K 7/06* (2013.01); *C07K 7/23* (2013.01); *C07K 14/575* (2013.01)
USPC ......... 514/5.2; 514/17.7; 514/17.9; 514/18.3; 530/350; 530/311; 530/326; 530/327

(58) Field of Classification Search
None
See application file for complete search history.

(56) References Cited

U.S. PATENT DOCUMENTS

| 3,610,795 A | 10/1971 | Antoine |
| 4,704,692 A | 11/1987 | Ladner |

(Continued)

FOREIGN PATENT DOCUMENTS

| EP | 0514361 | 11/1992 |
| EP | 1217071 | 6/2002 |

(Continued)

OTHER PUBLICATIONS

Banks et al., Peptides and the blood-brain barrier: Lipophilicity as a predictor of permeability. Brain Research Bulletin, vol. 15, Issue 3, Sep. 1985, pp. 287-292.*

(Continued)

*Primary Examiner* — Gregory S Emch
*Assistant Examiner* — Aurora M Fontainhas
(74) *Attorney, Agent, or Firm* — Seed IP Law Group PLLC

(57) ABSTRACT

Disclosed are compositions and methods related to improving pharmacological properties of bioactive compounds targeting nervous system.

7 Claims, 38 Drawing Sheets

(51) Int. Cl.
| | |
|---|---|
| C07K 7/08 | (2006.01) |
| C07K 14/665 | (2006.01) |
| C07K 5/11 | (2006.01) |
| C07K 14/575 | (2006.01) |
| C07K 14/655 | (2006.01) |
| C07K 7/06 | (2006.01) |
| C07K 7/23 | (2006.01) |

(56) References Cited

U.S. PATENT DOCUMENTS

| | | |
|---|---|---|
| 4,868,116 A | 9/1989 | Morgan |
| 4,897,355 A | 1/1990 | Eppstein |
| 4,980,286 A | 12/1990 | Morgan |
| 5,670,477 A | 9/1997 | Poduslo et al. |
| 5,965,788 A | 10/1999 | Houdebine |
| 6,261,834 B1 | 7/2001 | Srivastava |
| 7,786,133 B2 | 8/2010 | Bentley et al. |
| 8,435,940 B2 | 5/2013 | Bulaj |
| 2002/0013266 A1 | 1/2002 | Bently et al. |
| 2005/0186174 A1 | 8/2005 | Bossard |
| 2009/0281031 A1 | 11/2009 | Bulaj et al. |
| 2013/0324467 A1 | 12/2013 | White et al. |

FOREIGN PATENT DOCUMENTS

| | | |
|---|---|---|
| EP | 0527063 | 8/2004 |
| EP | 2 651 429 A2 | 10/2013 |
| WO | WO 89/07136 | 8/1989 |
| WO | WO 90/02806 | 3/1990 |
| WO | WO 2007/081792 | 12/2007 |
| WO | 2012/082942 A2 | 6/2012 |
| WO | WO 2012/082942 | 6/2012 |

OTHER PUBLICATIONS

Partial European Search Report issued Dec. 5, 2012 in European Divisional Application No. 12153130.5.
Extended European Search Report issued Aug. 27, 2009 in European Patent Application No. 07717960.4.
Notification of Transmittal of the International Search Report and the Written Opinion of the International Searching Authority issued Oct. 3, 2007 in International Application No, PCT/US2007/00261.
Notification Concerning Transmittal of Copy of International Preliminary Report on Patentability issued Jul. 17, 2008 in International Application No. PCT/US2007/00261.
Abrahmsen, L., et al., "Engineering Subtillsin and Its Substrates for Efficient Ligation of Peptide Bonds in Aqueous Solution," Biochemistry, vol. 30, pp. 4151-4159, (1991).
Baggiolini, M., et al., "Interleukin-8, a chemotactic and inflammatory cytokine," FEBS Lett., vol. 307, pp. 97-101, (1992).
Bagshawe, K.D., et al., "A cytotoxic agent can be generated selectively at cancer sites," Br. J. Cancer, vol. 58, pp. 700-703, (1988).
Bagshawe, K.D., "Towards generating cytotoxic agents at cancer sites," Br. J. Cancer, vol. 60, pp. 275-281, (1989).
Banerji, J., et al., "A lymphocyte-specific cellular enhancer is located downstream of the joining region in immunolgbulin heavy chain genes," Cell, vol. 33, p. 729, (1983).
Battelli, et al., "T lymphocyte killing by a xanthine-oxidase-containing immunotoxin," Cancer Immunol. Immunother, vol. 35, pp. 421-425, (1992).
Berkner et al., "Abundant expression of polymavirus middle T Antigen and dihydrofolate reductase in an adenovirus recombinant," J. Virology, vol. 61, pp. 1213-1220, (1987).
Bout, et al., "Lung gene therapy: In vivo adenovirus-mediated gene transfer to rhesus monkey airway epithelium," Human Gene Thereapy, vol. 5, pp. 3-10, (1994).
Brigham et al., "Expression of a prokaryotic gene in cultured lung endothelial cells after lipofaction with a plasmid vector," Am. J. Resp. Cell. Mol Biol., vol. 1, pp. 95-100, (1989).
Brown and Burlingham, "Penetration of Host Cell Membranes by Adenovirus 2," J. Virology, vol. 12, pp. 386-396, (1973).

Brown and Greene, "Molecular and Cellular Mechanisms of Receptor-Mediated Endocytosis," DNA and Cell Biology, vol. 10, Issue 6, pp. 399-409, (1991).
Bulaj, et al., "Design, Synthesis, and Characterization of High-Affinity, Systemically-Active Galanin Analogues with Potent Anticonvulsant Activities," Journal of Medicinal Chemistry, vol. 51, No. 24, pp. 8038-8047, (Dec. 25, 2008).
Caillaud C., et al., "Adenoviral vector as a gene delivery system into cultured rat neuronal and glial cells," EurJ Neurosci, vol. 5, pp. 1287-1291, (1993).
Chapman V, Dickenson AH, "The effects of sandostatin and somatostatin on nociceptive transmission in the dorsal horn of the rat spinal cord," Neuropeptides, vol. 23, pp. 147-152, (1992).
Chardonnet, Y, Dales, S, "Early events in the interaction of adenoviruses with Hela cells: penetration of type 5 and intercellular release of the DNA genome," Virology, vol. 40, pp. 462-477, (1970).
Clark-Lewis I., et al., "Chemical Synthesis, Purification, and Characterization of Two Inflammatory Proteins, Neutrophil Activating Peptide 1 (Interleukin-8) and Neutrophil Activating Peptide 2," Biochemistry, vol. 30, pp. 3128-3135, (1991).
Clark-Lewis I., et al., "Structural requirements for interleukin-8 function identified by design of analogs and CXC chemokine hybrids," J. Biol. Chem., vol. 269, pp. 16076-16081, (1994).
Cotter, M.A., et al., "Molecular genetic analysis of herpesviruses and their potential use as vectors for gene therapy applications," Curr Opin Mol Ther., vol. 1, pp. 633-644, (1999).
Davidson et al., "Overproduction of Polyomavirus Middle T Antigen in Mammalian Cells through the Use of an Adenovirus Vector" J. Virology, vol. 61, pp. 1226-1239, (1987).
Dawson et al., "Synthesis of proteins by native chemical ligation," Science, vol. 266, pp. 776-779, (1994).
de Lisle Milton, R. C., et al., "Synthesis of proteins by chemical Ligation of unprotected peptide segments: mirror-image enzyme molecules, D- & L-HIV protease analogs," Techniques in Protein Chemistry IV, Academic Press, New York, pp. 257-267, (1993).
Dietz GP, Bahr M., "Delivery of bioactive molecules into the cell: The Trojan horse approach," Mol Cell Neurosci, vol. 27, pp. 85-131, (2004).
Felgner et al., "Lipofection: A Highly Efficient, Lipid-mediated DNA-transfection Procedure," Proc. Natl. Acad. Sci. USA, vol. 84, pp. 7413-7417, (1987).
Fiers et al., "Complete nucleotide sequence of SV40 DNA," Nature, vol. 273, pp. 113-120, (1978).
Gomez-Foix, "Adenovirus-mediated Transfer of the Muscle Glycogen Phosphorylase Gene into Hepatocytes Confers Altered Regulation of Glycogen Metabolism," J. Bioi. Chem., vol. 267, pp. 25129-25134, (1992).
Greenway, et al., "Human cytomegalovirus DNA: BamHi,-EcoRI and PstI restriction-endonuclease cleavage maps," Gene, vol. 18, pp. 355-360, (1982).
Guzman, "Efficient Gene Transfer Into Myocardium by Direct Injection of Adenovirus Vectors," Circulation Research, vol. 73, pp. 1201-1207, (1993).
Haj-Ahmad et al., "Development of a Helper-Independent Human Adenovirus Vector and Its Use in the Transfer of the Herpes Simplex Virus Thymidine Kinase Gene," J. Virology, vol. 57, pp. 267-274, (1986).
Hawes, J.J., et al., "Galanin and galanin-like peptide modulate neurite outgrowth via protein kinase C-mediated activation of extracellular singal-related kinase," Eur J Neurosci. Jun, vol. 23, Issue 11, pp. 2937-2946, (2006).
Hughes, et al., "MonoClonal Antibody Targeting of Liposomes to Mouse Lung in Vivo," Cancer Research, vol. 49, pp. 6214-6220, (1989).
Ikuta, et al., "Synthesis and use of synthetic oligonucleotides," Annu Rev Biochem., vol. 53, pp. 323-356, (1984).
Jaeger, J.A., et al., "Predicting optimal and suboptimal secondary structure for RNA," Methods Enzymol., vol. 183, pp. 281-306, (1990).
Jaeger et al., "Improved Predictions of Secondary Structures for RNA," Proc. Natl. Acad. Sci. USA, vol. 86, pp. 7706-7710, (1989).

(56) References Cited

OTHER PUBLICATIONS

Kirshenbaum, L.A., et al., "High efficient gene transfer into adult ventricular myocytes by recombinant adenovirus," J. Clin. Invest., vol. 92, pp. 381-387, (1993).
Kroll, R.A., et al., "outwitting the blood-brain barrier for therapeutic purposes: osmotic opening and other means," Neurosurgery, vol. 42, Issue 5, pp. 1083-1100, (1998).
La Salle et al., "An adenovirus vector for gene transfer into neurons and glia in the brain," Science, vol. 259, pp. 988-990, (1993).
Laimins, L., et al., "osmotic control of kdp operon expression in *Escherichia coli*," Proc. Natl. Acad. Sci. USA, vol. 78, No. 1, pp. 464-468, (1981).
Langel et al., "Chemistry and molecular biology of galanin receptor ligands," Ann NY Acad Sci, vol. 863, pp. 860-890, (1998).
Litzinger and Huang, "Biodistribution and immunotargetability of ganglioside-stabilized dioleoylphosphatidylethanolamine liposomes", Biochimica et Biophysica Acta, vol. 1104, pp. 179-187, (1992).
Liu, et al., "Receptor Subtype-Specific Pronociceptive and Analgesic Actions of Galanin in the Spinal Cord: Selective Actions via GalR1 Receptors," Proceedings of the National Academy of Sciences, National Academy of Sciences, US. vol. 98, No. 17, Aug. 14, 2001, pp. 9960-9964.
Lusky, et al., "Bovine papilloma virus Contains an activator of gene expression at the distal end of the early transcription unit," Mol. Cell Bio., vol. 3, Issue 6, pp. 1108-1122, (1983).
Maletinska, et al., "Angiotensin Analogues Palmitoylated in Positions 1 and 4," Journal of Medcinal Chemistry, American Chemical Society, US, vol. 10, No. 20, Sep. 26, 1997, pp. 3272-3279.
Massie, et al., "Construction of a helper-free recombinant adenovirus that expresses polyomavirus large T antigen," Mol. Cell. Biol., vol. 6, Issue 8, pp. 2872-2883, (1986).
Morsy, "Efficient adenoviral-mediated ornithine transcarbamylase expression in deficient mouse and human hepatocytes," J. Clin. Invest. vol. 92, Issue 3, pp. 1580-1586, (1993).
Moullier, "Correction of lysosmal storage in the liver and spleen of MPS VII mice by implantation of genetically modified skin fibroblasts," Nature Genetics vol. 4 Issue 2, pp. 154-159, (1993).
Mulligan, et al., "Expression of a bacterial gene in mammalian cells," Science, vol. 209 No. 4463, pp. 1422-1427, (1980).
Mulligan, et al., "The basic science of gene therapy," Science vol. 260, pp. 926-932, (1993).
Narang, et al., "Chemical synthesis of deoxyoligonucleotides by the modified triester method," Methods Enzymol., vol. 65, pp. 610-620, (1980).
Needleman, S.B., et al., "A general method applicable to the search for similarities in the amino acid sequence of two proteins," J. Mol. Biol., vol. 48, pp. 443-453, (1970).
Nielsen et al., "Peptide Nucleic Acid (PNA), A DNA Mimic with a Peptide Backbone," Bioconjug. Chem., vol. 5, pp. 3-7, (1994).
Osborne, et al., "Transcription control region within the protein-coding portion of adenovirus E1A genes," Mol. Cell Bio., vol. 4, Issue 7, pp. 1293-1305, (1984).
Peareson and Lipman, "Improved tools for biological sequence comparison," Proc. Natl. Acad. Sci. U.S.A., vol. 85, p. 2444, (1988).
Pietersz, et al., "Antibody conjugates for the treatment of cancer," Immunolog. Reviews, vol. 129, pp. 57-80, (1992).
Pooga M., et al., "Novel galanin receptor ligands," J Pept Res, vol. 51, Issue 1, pp. 65-74, (1988).
Racine RJ., "Modification of seizure activity by electrical stimulation," II. Motor seizure. Electroencephalogr Clin Neurophysiol. Mar; vol. 32, Issue 3, pp. 281-294, (1972).
Ragot, T., et al., "Replication defective recombinant adenovirus expressing the Epstein-Barr virus (EBV) envelope glycoprotein gp340/220 induces protective immunity against EBV-induced lymphomas in the cottontop tamarin," J. Gen. Virology, vol. 74, pp. 501-507, (1993).
Rajarathnam, K., et al., "1H NMR studies of interleukin 8 analogs: characterization of the domains essential for function," Biochemistry vol. 33, pp. 6623-6630, (1994).

Rivera Baeza et al., "Analogs of galanin (1-16) modified in positions 103 as ligands to rat hypothalamic galanin receptors," Acto Chem Scand, vol. 48, Issue 5, pp. 434-438, (1994).
Roessler, "Adenoviral-mediated Gene Transfer to Rabbit Synovium In Vivo," J. Clin. Invest., vol. 92, pp. 1085-1092, (1993).
Roffler, et al., "Anti-neoplastic glucuronide prodrug treatment of human tumor cells targeted with a monoclonal antibody-enzyme conjugate," Biochem. Pharmacol., vol. 42, Issue 10, pp. 2062-2065, (1991).
Saito, T., et al., "Somatostatin regulates brain amyloid beta peptide Abeta42 through modulation of proteolytic degradation," Nature Medicine, vol. 11, pp. 434-439, (2005).
Schnolzer, M., et al., "Constructing proteins by dovetailing unprotected synthetic peptides: backbone-engineered HIV protease," Science, vol. 256, p. 221, (1992).
Senter, et al., "Generation of 5-Fluorouracil from 5-Fluorocytosine by Monoclonal Antibody-Cystosine Deaminase Conjugates, Bioconjugate Chem.," vol. 2, pp. 447-451, (1991).
Senter, et al., "Generation of Cytotoxic Agents by Targeted Enzymes," Bioconjugate Chem., vol. 4, Issue 1, pp. 3-9, (1993).
Seth, et al., "Role of low-pH environment in adenovirus enhancement of the toxicity of a *Pseudomonas* exotoxin-epidermal growth factor conjugate," J. Virol., vol. 51, Issue 3, pp. 650-655, (1984).
Seth, et al., "Evidence that the penton base of adenovirus is involved in potentiation of toxicity of *Pseudomonas* exotoxin conjugated to epidermal growth factor," Mol. Cell. Biol., vol. 4, Issue 8, pp. 1528-1533, (1984).
Smith and Waterman, "Comparison of biosequences," Adv. Appl. Math., vol. 2, pp. 482, (1981).
Southern P., et al., "Transformation of Mammalian Cells to Antibiotic Resistance with a Bacterial Gene Under Control of the SV40 Early Region Promoter" J. Molec. Appl. Genet., vol. 1, pp. 327-341, (1982).
Suarez V, et al, "The axotomy-induced neuropeptides galanin and pituitary adenylate cyclase-activating peptide promote axonal sprouting of primary afferent and cranial motor neurons," Eur J Neurosci., 200624(6):1555-64 (2006).
Sugden, B., et al., "A vector that replicates as a plasmid and can be efficiently selected in B lymphocytes transformed by Epstein-Barr virus," Mol. Cell. Biol. 5:410-413 (1985).
Sun, T.Q., et al., "Human artificial episomal chromosomes for cloning large DNA in human cells," Nature Genetics, vol. 8, pp. 33-41, (1994).
Svensson, et al., "Role of vesicles during adenovirus 2 internalization into hela cells," J. Virology, vol. 55, Issue 2, pp. 442-449, (1985).
Toyobuku, et al., "Delivery of peptide drugs to the brain by adenovirus-mediated heterologous expression of human oligopeptide transporter at the blood-brain barrier" J. Pharmacol. Exp. Ther., vol. 305, Issue 1, pp. 40-47, (2003).
Varga, et al., "Infectious Entry Pathway of Adenovirus Type 2," J. Virology, vol. 65, Issue 11, pp. 6061-6070, (1991).
Vezzani, A., et al., "Brain somatostatin: a candidate inhibitory role inseizures and epileptogenesis," EurJ. Neurosci., vol. 11, pp. 3767-3776, (1999).
White, et al., "Developing Novel Antiepileptic Drugs: Characterization of NAX 5055, a Systemically-Active Galanin Analog, in Epilepsy Models." Neurotherapeutics: The Journal of the American Society for Experimental Neurotherapeutics, vol. 6, No. 2, pp. 372-380, (Apr. 2009).
Wickham, T.J., et al., "Integrins alpha v beta 3 and alpha v beta 5 promote adenovirus internalization but not virus attachment," Cell 73, pp. 309-319, (1993).
Witt, et al., "Peptide drug modifications to enhance bioavailability and blood-brain barrier permeability," Peptides, vol. 22, Issue 12, pp. 2329-2338, (2001).
Wolff, J.A., "Human Dystrophin Expression in MDX Mice After Intramuscular Injection of DNA Constructs," Nature, vol. 352, pp. 815-818, (1991).
Wolff, J.A., et al., "Direct Gene Transfer Into Mouse Muscle In Vivo", Science, vol. 247, pp. 1465-1468, (1990).
Zabner, J., et al., "Adenovirus-mediated gene transfer transiently corrects the chloride transport defect in nasal epithelia of patients with cystic fibrosis," Cell 75, pp. 207-216, (1993).

(56) References Cited

OTHER PUBLICATIONS

Zabner, "Safety and efficacy of repetitive adenovirus-mediated transfer of CFTR cDNA to airway epithelia of primates and cotton rats," *Nature Genetics*, vol. 6, Issue 1, pp. 75-83, (1994).

Zhang "Generation and identification of recombinant adenovirus by liposome-mediated transfection and PCR analysis" BioTechniques, vol. 15, pp. 868-872, (1993).

Zuker, M., "On finding all suboptimal foldings of an RNA molecule," *Science*, vol. 244, pp. 48-52, (1989).

Rich, Human Gene Therapy, vol. 4, pp. 461-476, (1993).

Verma, I.M., "Retroviral vectors for gene transfer in Microbiology," American Society for Microbiology, pp. 229-232, (1985).

Benner, "Expanding the genetic lexicon: incorporating non-standard amino acids into proteins by ribosome-based synthesis," *TIBTECH* 12(2):158-162, 1994.

Anthony-Cahill et al., "Site-Specific mutagenesis with unnatural amino acids," *TIBS* 14(10):400-403, 1989.

Chaplan et al., "Quantitative assessment of tactile allodynia in the rat paw," *Journal of Neuroscience Methods* 53:55-63, 1994.

Dirig et al., "Characterization of variables defining hindpaw withdrawal latency evoked by radiant thermal stimuli," *Journal of Neuroscience Methods* 76:183-191, 1997.

Hargreaves et al., "A new and sensitive method for measuring thermal nociception in cutaneous hyperalgesia," *Pain* 32:77-88, 1988.

Ibba et al., "Twards Engineering Proteins by Site-Directed Incorporation In Vivo of Non-Natural Amino Acids," *Bio/Technology* 12(7):678-682, 1994.

Ibba, "Strategies for in vitro and in vivo translation with non-natural amino acids," *Biotechnology and Genetic Engineering Reviews* 13:197-216, 1995.

International Preliminary Report on Patentability, mailed Jun. 27, 2013, for International Application No. PCT/US2011/064977, 9 pages.

International Search Report and Written Opinion of the International Searching Authority, mailed Aug. 17, 2012, for International Application No. PCT/US2011/064977, 13 pages.

Jensen et al., "Effects of an Intrathecal Dopamine Agonist, Apomorphine, on Thermal and Chemical Evoked Noxious Responses in Rats," *Brain Research* 296(2):285-293, 1984.

Rizo et al., "Constrained Peptides: Models of Bioactive Peptides and Protein Substructures," *Annu. Rev. Biochem.* 61:387-418, 1992.

Thorson et al., "A Biosynthetic Approach for the Incorporation of Unnatural Amino Acids into Proteins," *Methods in Molecular Biology* 77:43-73, 1998.

Tjolsen et al., "The formalin test: an evaluation of the method," *Pain* 51:5-17, 1992.

Zoller, "New recombinant DNA methodology for protein engineering," *Current Opinion in Biotechnology* 3:348-354, 1992.

\* cited by examiner

Figure 9: Design of peptide analogs that penetrate the BBB

Figure 16: NAX 5055, but not the native peptide (Gal 1-16) attenuates formalin-induced hyperalgesia Note: NAX 5055 was administered 60 min prior to plantar injection of formalin. Time was based on anticonvulsant time of peak effect.

Figure 17: Effect of gabapentin (GBP) on formalin-induced hyperalgesia

Figure 18: NAX 5055 (2 mg/kg) Displays a Time-dependent Analgesic Effect in Rat Sciatic Ligation Model of Chronic Pain

| Spacer | Analog |
|---|---|
| - | NAX 30611 |
| Gly | NAX 30612 |
| Ahx | NAX 30613 |
| Ahx-Gly | NAX 30614 |
| PEG-O2Oc | NAX 30615 |

GWTLNSAGYLLGPHAV-NH$_2$

Figure 35

| NAX | Structure | % Protection at 1, 2 and 4 hours afforded by a dose of 4 mg/kg, i.p. |
|---|---|---|
| Gal(1-16) | GWTLNSAGYLLGPHAV (SEQ ID NO: 1) | Not active |
| Individual (cationization OR lipidization) | | |
| 1105-2 | (Sar)WTLNSAGYLLGPKKKK (SEQ ID NO: 21) | 30%, 0%, 0%* (3.7mg/kg) |
| 306-5 | (Sar)WTLNSAGYLLGPHA(K$_P$) (SEQ ID NO: 68) | Not active |
| Combination (cationization AND lipidization) | | |
| 5055 | (Sar)WTLNSAGYLLGPKK(K$_P$)K (SEQ ID NO: 18) | 100%, 100%, 0% (0.8 mg/kg) |

# METHODS AND COMPOSITIONS RELATED TO IMPROVING PROPERTIES OF PHARMACOLOGICAL AGENTS TARGETING NERVOUS SYSTEM

CROSS-REFERENCE TO RELATED APPLICATIONS

This application is a continuation of U.S. application Ser. No. 12/160,035, filed Dec. 18, 2008, which is a U.S. National Stage Application and claims priority to International Application No. PCT/US2007/000261, filed Jan. 5, 2007, which claims the benefit of U.S. Provisional Application No. 60/757,047, filed Jan. 5, 2006, and to U.S. Provisional Application No. 60/844,024, filed Sep. 11, 2006. This application hereby incorporates by reference U.S. application Ser. No. 12/160,035, International Application No. PCT/US2007/000261, U.S. Provisional Application No. 60/757,047 and U.S. Provisional Application No. 60/844,024.

BACKGROUND OF THE INVENTION

The blood—brain barrier (BBB) separates the mammalian brain from the systemic circulation and plays a vital role in the homeostasis of the central nervous system (CNS). Despite the continuous progress in understanding transport of peptides through the blood-brain barrier, their efficient delivery directly into the CNS has remained a major challenge in developing neuropeptides as potential therapeutics.

Epilepsy, for example, is a complex neurological disorder. Intractable epilepsy is estimated to affect 30% of the patient population. Despite availability of various antiepileptic drugs (AEDs), certain types of seizures and epilepsy syndromes respond with limited success to only a few AEDs. Therefore, there is an ongoing need to discover and develop new anticonvulsant therapeutics with improved efficacy and safety profiles. Moreover, recent discoveries of neurobiological changes that occur prior to an epileptic seizure have opened an opportunity for the discovery of new antiepileptogenic compounds, and such antiepileptogenic agents can include neuropeptides and neurotrophins.

Neuropeptides and their receptors that have been implicated in the mechanisms of epileptic seizures include galanin, neuropeptide Y, somatostatin and opioid peptides. Some of these neuropeptides, when delivered directly into the central nervous system (CNS), possess an anticonvulsant activity, but their poor bioavailability and marginal metabolic stability preclude development of neuropeptide-based antiepileptic drugs. On the other hand, advanced peptide engineering has produced many successful instances of peptide analogs with improved stability or bioavailability. However, none of the available peptide engineering techniques have been applied to neuropeptides with anticonvulsant activity. What is needed in the art are methods and compositions for improving permeability through the blood-brain barrier.

I. SUMMARY OF THE INVENTION

In accordance with the purposes of this invention, as embodied and broadly described herein, this invention, in one aspect, relates to an isolated polypeptide comprising SEQ ID NO: 3, an amino acid sequence at least about 90% identical to the amino acid sequence of SEQ ID NO: 3, or the amino acid sequence of SEQ ID NO: 3 having one or more conservative amino acid substitutions.

Also disclosed is an isolated polypeptide comprising an amino acid sequence selected from the group consisting of SEQ ID NO: 2, 4-29, 37-39, 50, 64, 65, 66, 67, 80, 82, and 89, an amino acid sequence at least about 90% identical to an amino acid sequence selected from the group consisting of SEQ ID NO: 2, 4-29, 37-39, 50, 64, 65, 66, 67, 80, 82, and 89, or the amino acid sequence selected from the group consisting of SEQ ID NO: 2, 4-29, 37-39, 50, 64, 65, 66, 67, 80, 82, and 89 having one or more conservative amino acid substitutions.

Also disclosed is an isolated polypeptide comprising an amino acid segment selected from the group consisting of SEQ ID NO: 31-36, an amino acid sequence at least about 90% identical to the amino acid sequence selected from the group consisting of SEQ ID NO: 31-36, or the amino acid sequence selected from the group consisting of SEQ ID NO: 31-36 having one or more conservative amino acid substitutions.

Also disclosed is an isolated polypeptide comprising SEQ ID NO: 40, an amino acid sequence at least about 90% identical to the amino acid sequence of SEQ ID NO: 40, or the amino acid sequence of SEQ ID NO: 40 having one or more conservative amino acid substitutions.

Also disclosed is an isolated polypeptide comprising an amino acid sequence selected from the group consisting of SEQ ID NO: 105, 106, 107, 108, 109-112, and 113-118, an amino acid sequence at least about 90% identical to the amino acid sequence selected from the group consisting of SEQ ID NO: 105, 106, 107, 108, 109-112, and 113-118, or the amino acid sequence selected from the group consisting of SEQ ID NO: 105, 106, 107, 108, 109-112, and 113-118 having one or more conservative amino acid substitutions.

Also disclosed is an isolated polypeptide comprising an amino acid sequence selected from the group consisting of SEQ ID NO: 58 and 135-141, an amino acid sequence at least about 90% identical to the amino acid sequence selected from the group consisting of SEQ ID NO: 58 and 135-141, or the amino acid sequence selected from the group consisting of SEQ ID NO: 58 and 135-141 having one or more conservative amino acid substitutions.

Further disclosed is a composition with increased permeability of the blood-brain barrier, wherein the composition comprises a peptide with increased lipophilic character and increased basicity when compared to the non-altered form of the peptide.

Disclosed is a method of increasing permeability of the blood-brain barrier for a peptide, comprising increasing lipophilic character and increasing basicity of the peptide compared to the non-altered form of the peptide.

Also disclosed is a method of treating epilepsy, comprising administering to a subject in need thereof an effective amount of a polypeptide as disclosed herein. Further disclosed is a method of treating epilepsy, comprising administering to a subject in need thereof an effective amount of a composition as disclosed herein.

Disclosed is a method of treating, preventing, or ameliorating pain or other neurological disorders comprising administering to a subject in need thereof an effective amount of a polypeptide as disclosed herein.

Also disclosed is a method of treating a subject in need of a composition that crosses the blood-brain barrier, comprising: identifying the composition to be used in treatment of the subject; modifying the composition by increasing lipophilicity and basicity of the composition; and administering the modified composition to the subject in need thereof.

Further disclosed is a method of treating a subject in need of a composition that crosses the blood-brain barrier, comprising: identifying the composition to be used in treatment of the subject; modifying the composition by increasing lipophilicity, glycosylation, and basicity of the composition; and administering the modified composition to the subject in need thereof.

Also disclosed is a method of treating a subject in need of a composition that crosses the blood-brain barrier, comprising: identifying the composition to be used in treatment of the subject; modifying the composition by increasing lipophilicity, glycosylation, and basicity of the composition; inserting the modified composition into a vector; and administering the vector to the subject in need thereof.

Further disclosed is a method of treating a subject in need of a composition that crosses the blood-brain barrier, comprising: identifying the composition to be used in treatment of the subject; modifying the composition by increasing lipophilicity and basicity of the composition; inserting the modified composition into a vector; and administering the vector to the subject in need thereof.

II. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows the role of neuropeptides in GABA- and GLU-mediated neurotransmission in SSSE hippocampal neuronal circuitry. Abbreviations: CA, pyramidal neurons; DYN, dynorphin; GABA, γ-amino butyric acid; GAL, galanin; GLU, glutamate; NE, norepinephrine; NPY, neuropeptide Y; SOM, somatostatin; SubsP, substance P (Wasterlain et al. 2002).

FIG. 2 shows galanin injected into the hilus before of after stimulation, shortened the duration of seizures in rats. Upper plot. Galanin (50 and 500 picomoles) was injected 30 minutes prior to perforant-path stimulation (PPS). Lower plot. Only injection of 500 picomoles of galanin was effective in reducing the duration of seizures when injected 30 minutes after the PPS (Mazarati et al. 1998).

Figure 8:
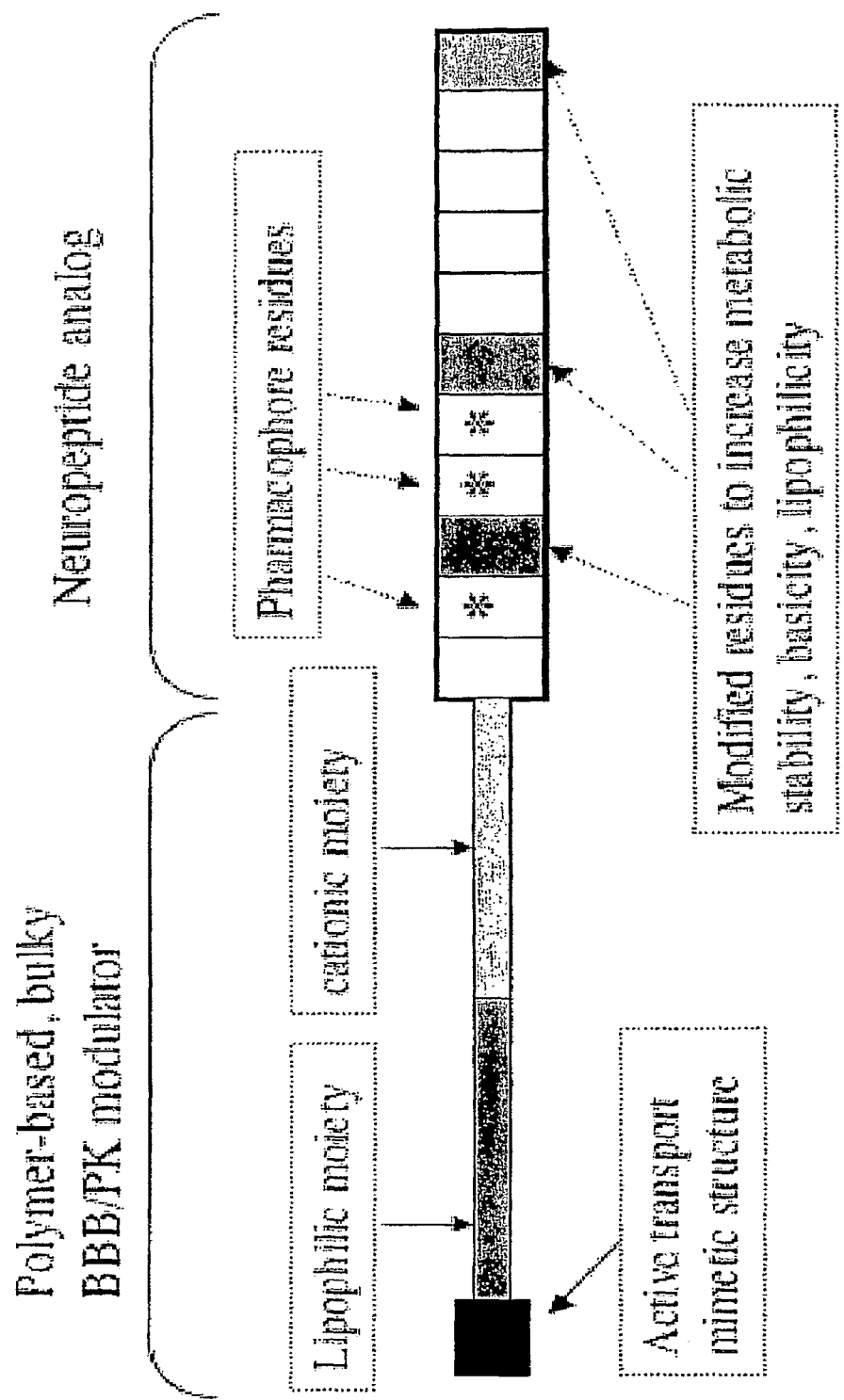

FIG. 8 shows structural organization of a prototype of an ideal neuropeptide drug. Stars denote residues of the pharmacophore. Grey boxes represent backbone and side chain modifications that increase metabolic stability, basicity and lipophilicity of the peptide moiety. The BBB/PK-modifier is a bulky, polymer-based structure containing lipophilic and cationic modules and endogenous nutrient mimetics. The cationic module increases absorptive-mediated endocytosis through electrostatic interactions with membranes. The lipophilic module increases passive transport through the blood-brain barrier. The active transport mimetic structure (e.g., hexose or phenylalanine) serves as a substrate for interactions with inwardly directed nutrient transporters located in the blood-brain barrier.

Figure 9:
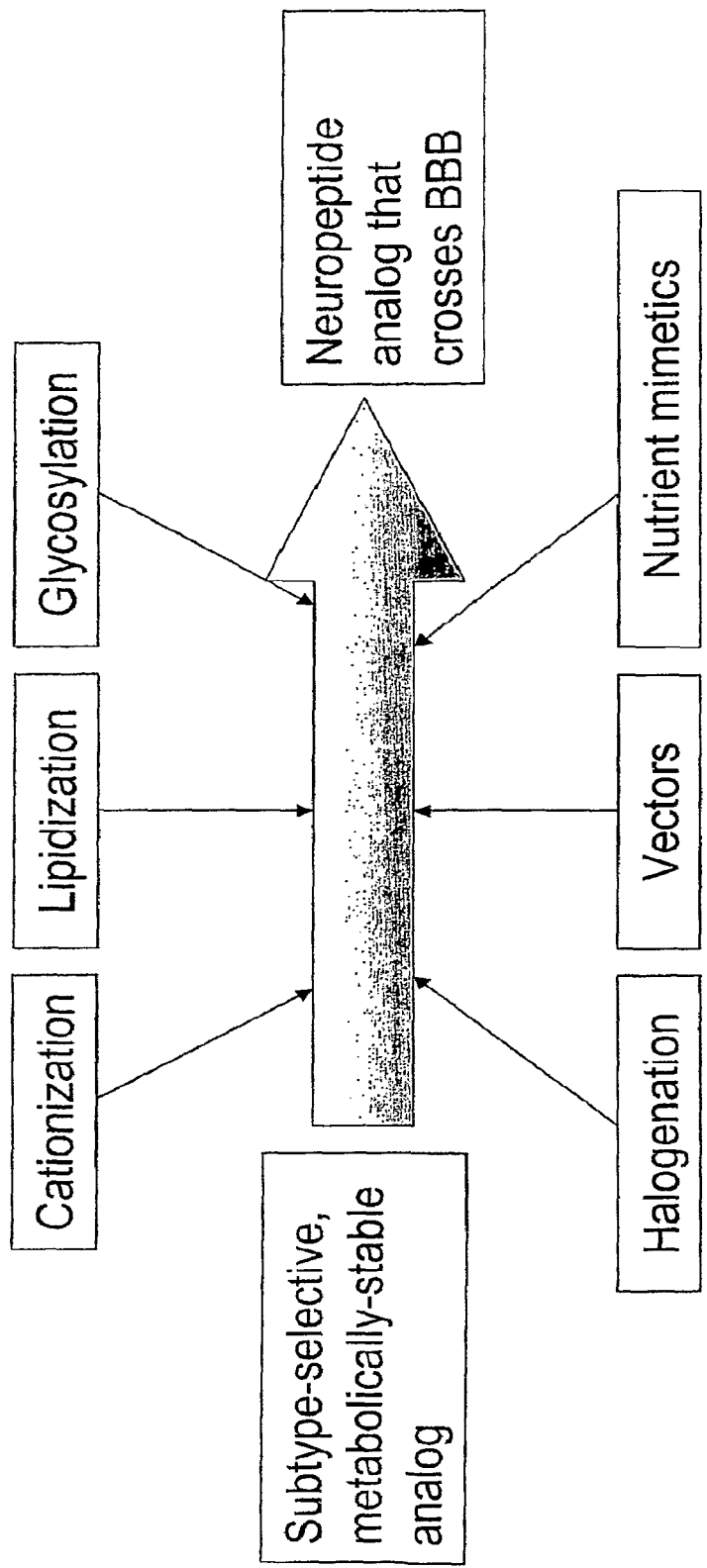

FIG. 9 shows the strategy used to design peptide analogs that penetrate the BBB. Combinations of two or more distinct chemical modifications that improve permeability of the analogs through the BBB are shown.

Figure 10:
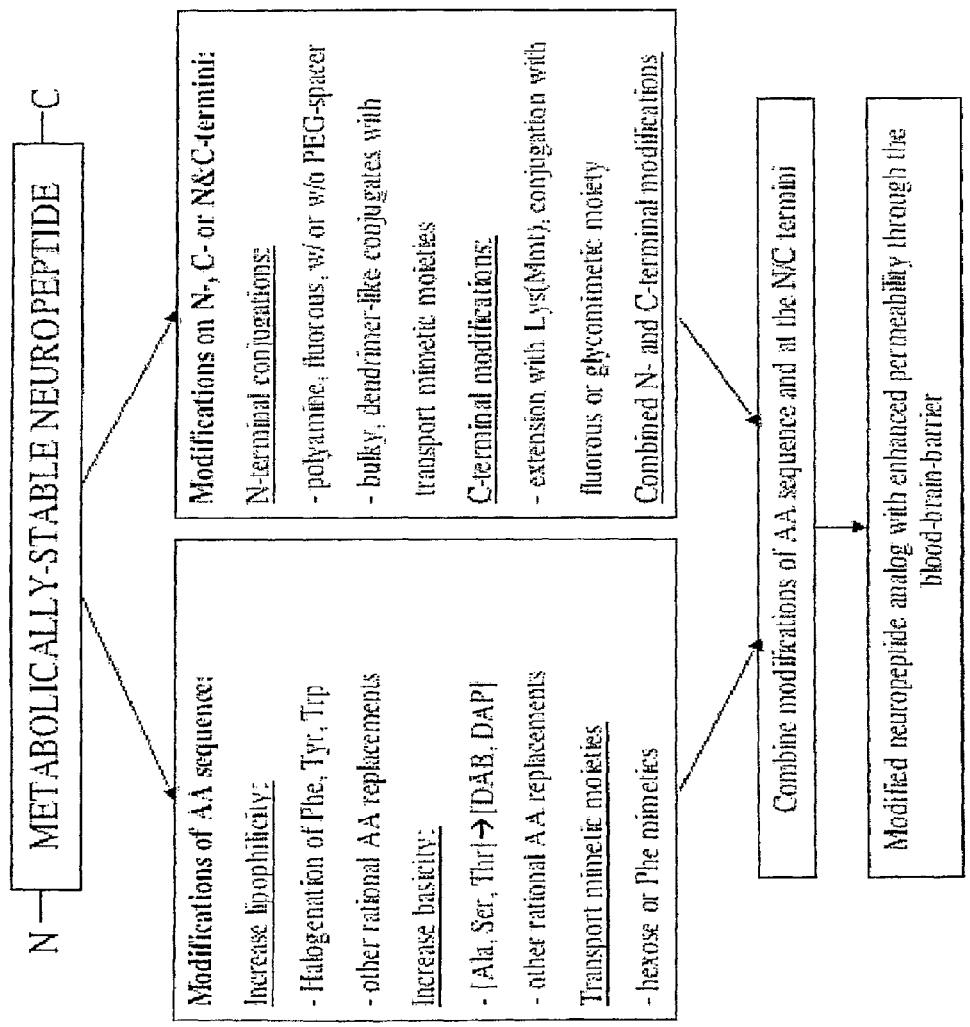

FIG. 10 shows a systematic approach to engineering neuropeptides to improve their permeability through the blood-brain barrier. Key: DAB, diaminobutyric acid; DAP, diaminopropionic acid; PEG, polyethylene glycol; Mmt, 4-methyltrityl.

Figure 11:
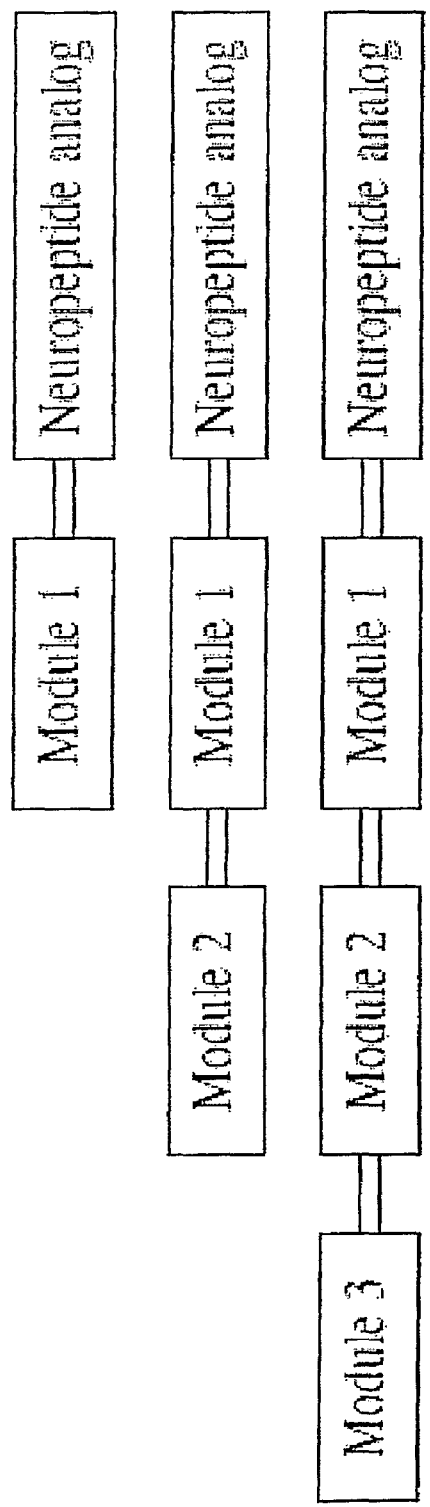

FIG. 11 shows modular structure of the N-terminal extension in somatostatin analogs. The modules are coupled during solid-phase peptide synthesis. The number and order of modules is arbitrary, and the structural composition of the BBB/PK modulator can be optimized.

Figure 12:
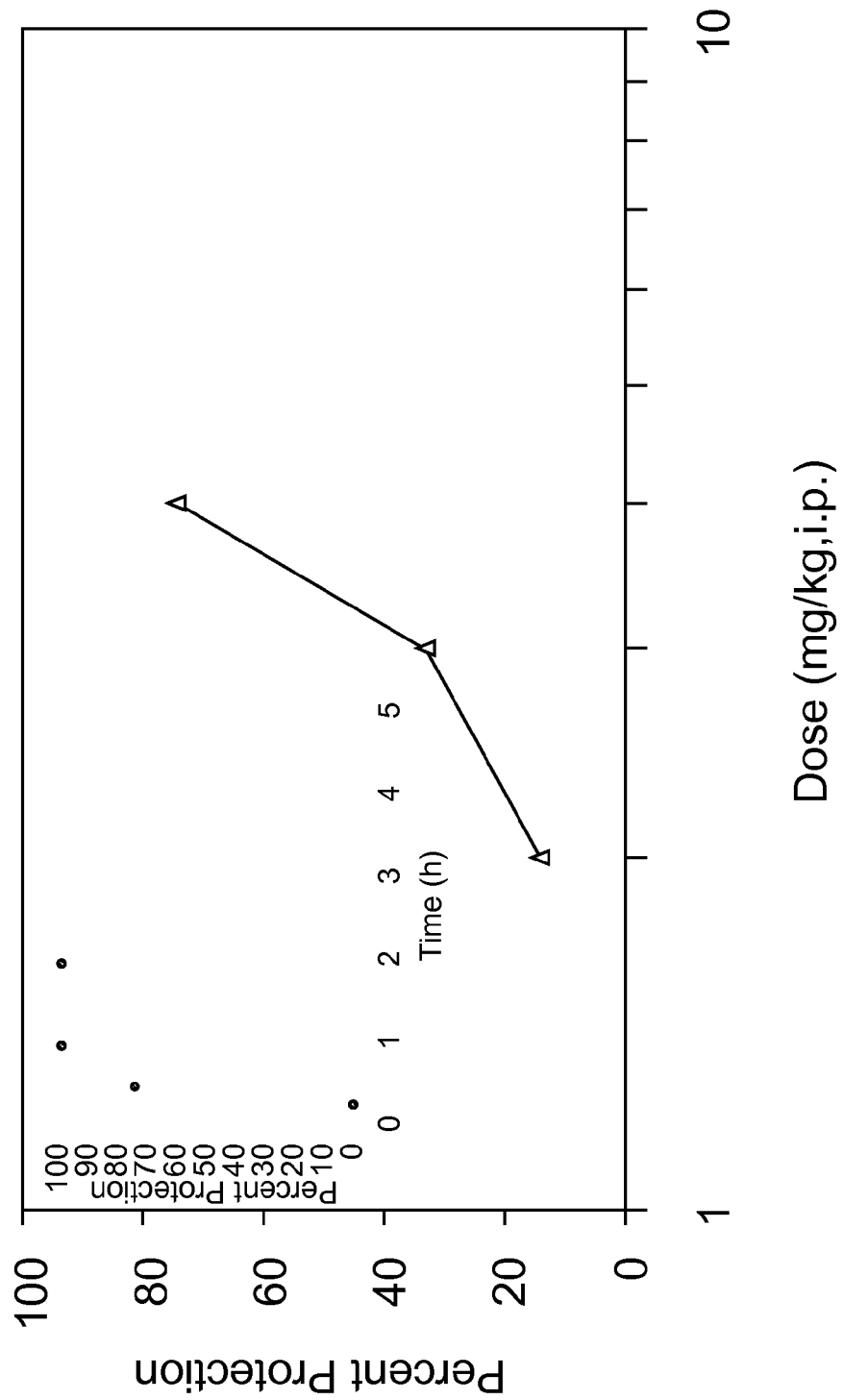

FIG. 12 shows Gal BBB-2 displays time (inset) and dose-dependent protection against audiogenic seizures in the Frings mouse. For the time course mice were treated with 4 mg/kg, i.p. Gal BBB-2 and tested at various times after administration. For the dose-response study groups of Frings mice were treated with increasing doses of Gal BBB-2 and tested one hour after i.p. administration.

Figure 13:
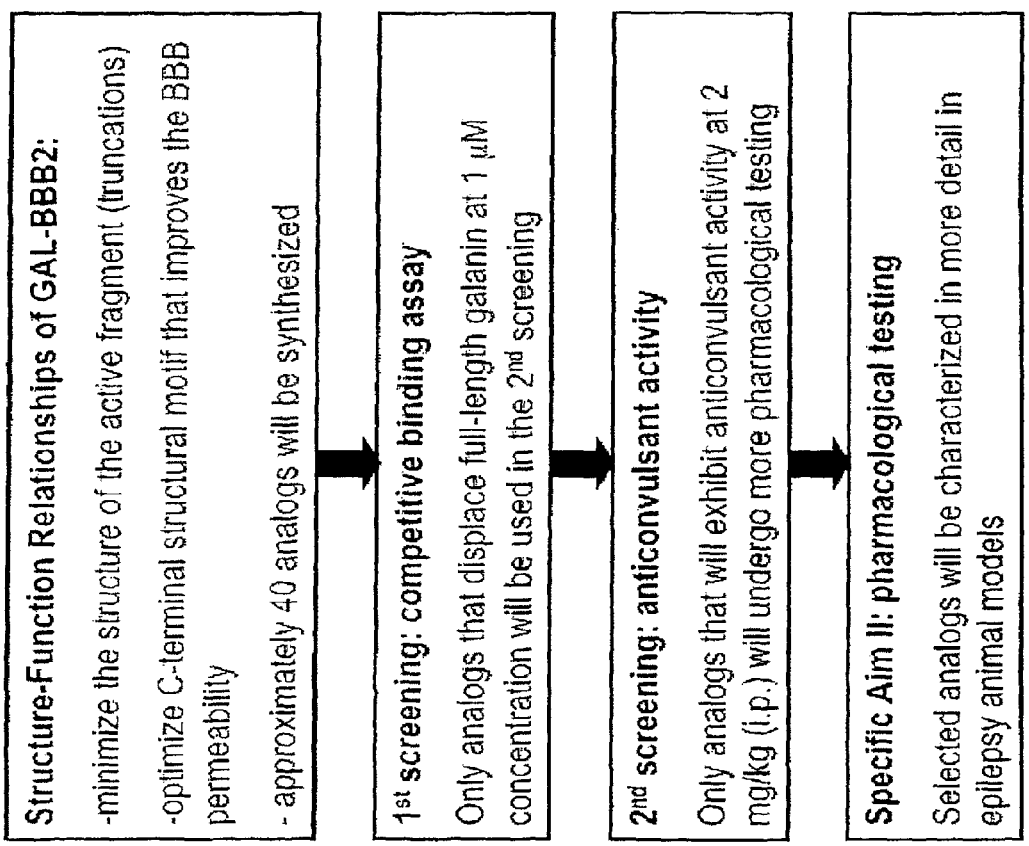

FIG. 13 shows general experimental strategy of optimizing GAL-BBB2. First three boxes summarize activity defined in Example 1. Approximately 40 analogs are synthesized and screened in the competitive binding assay. Only the most potent galanin ligands are further screened for their potent and long-lasting anticonvulsant activity, before more detailed pharmacological characterization.

Figure 14:
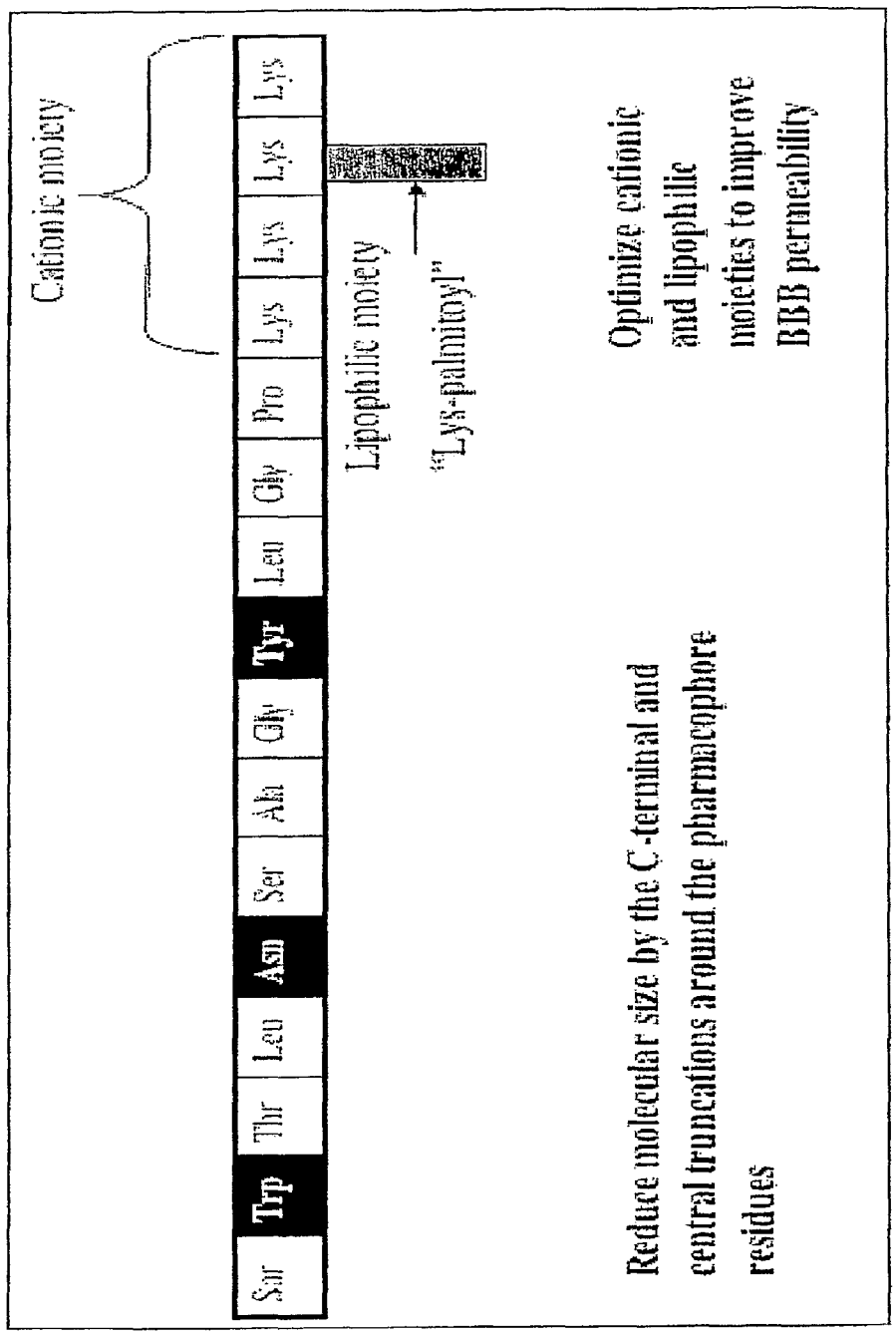

FIG. 14 shows structural organization of GAL-BBB2 and proposed SAR studies. Black boxes illustrate key pharmacophore residues.

Figure 15:
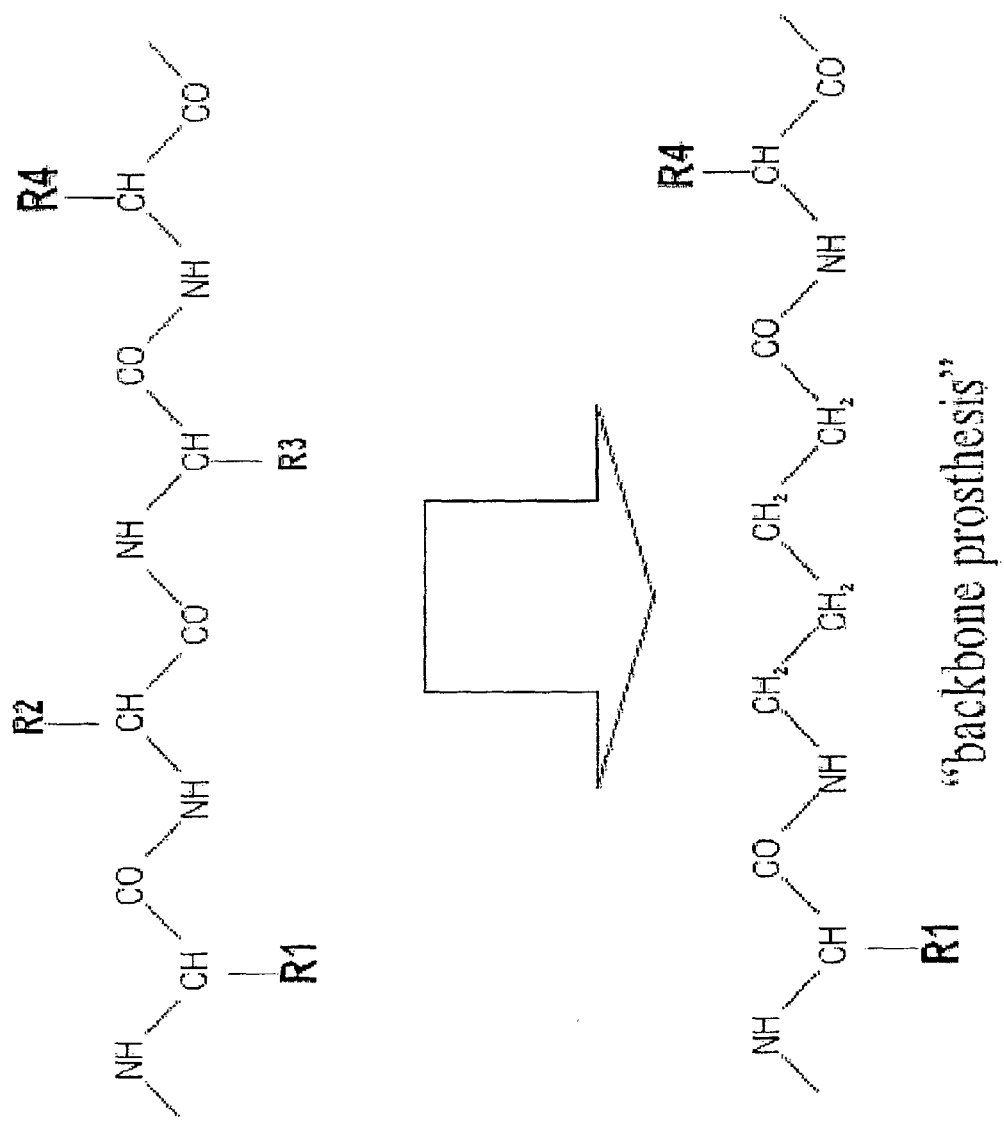

FIG. 15 shows "backbone prosthesis"—replacement of non-pharmacophore residues (R2 and R3) with a non-peptide spacer (5-aminovaleric acid). Other backbone spacers include aminohexanoic acid or amino-3,6-dioxaoctanoic acid (PEG-spacer).

Figure 16:
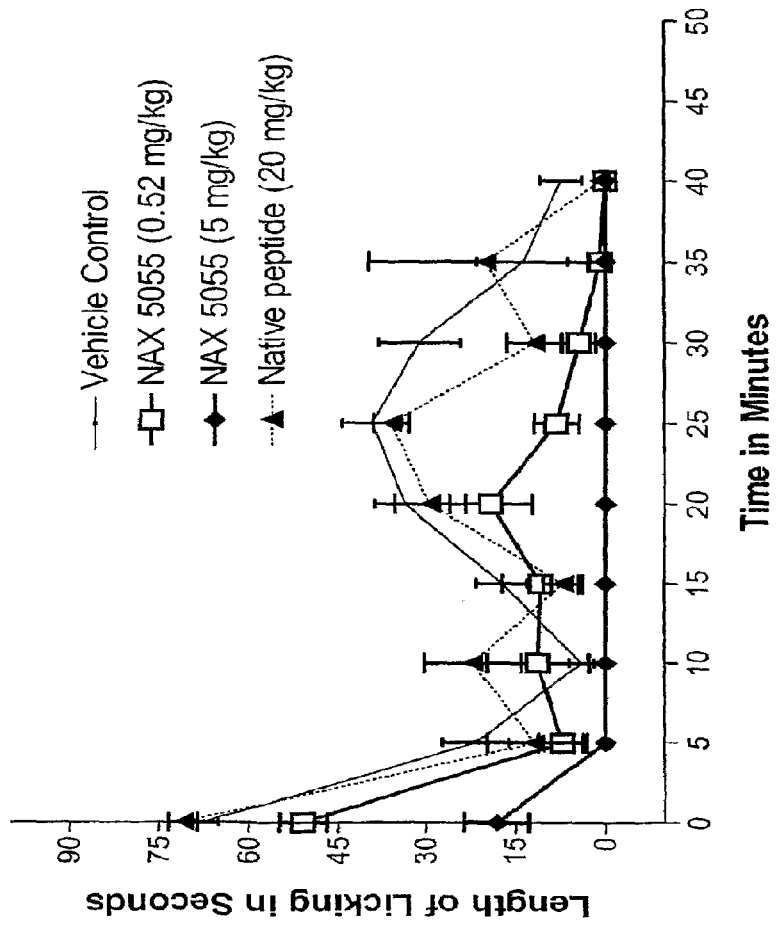

FIG. 16 shows GAL-BBB2 (labeled as NAX-5055 in the figure) (0.52-5 mg/kg) produced a dose-dependent reduction in paw licking during both the initial acute phase as well as the prolonged inflammatory phase. In contrast, the un-modified native fragment Gal 1-16 was found to be inactive following i.p. administration of a dose 4 times higher than the highest dose of GAL-BBB2 tested (i.e., 20 mg/kg).

Figure 17:
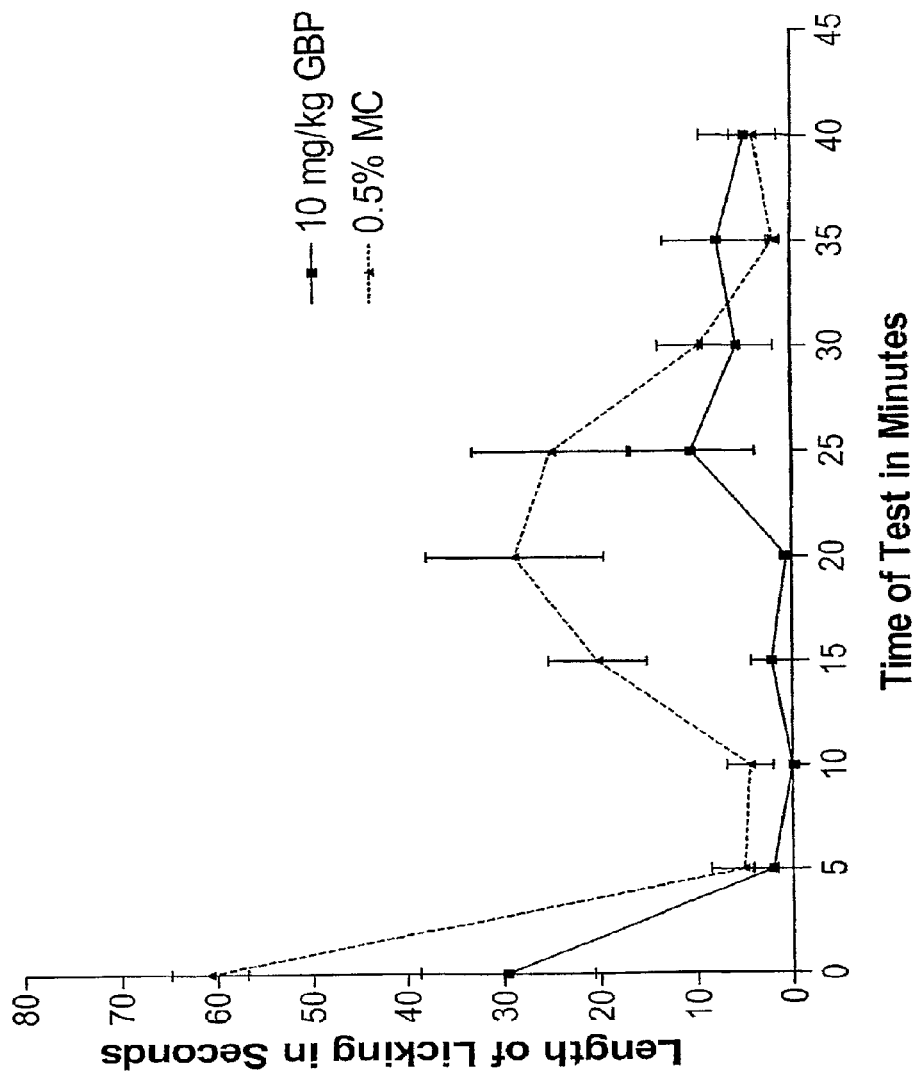

FIG. 17 shows that 5 mg/kg GAL-BBB2 was found to be equivalent to a 10 mg/kg dose of gabapentin.

Figure 18:
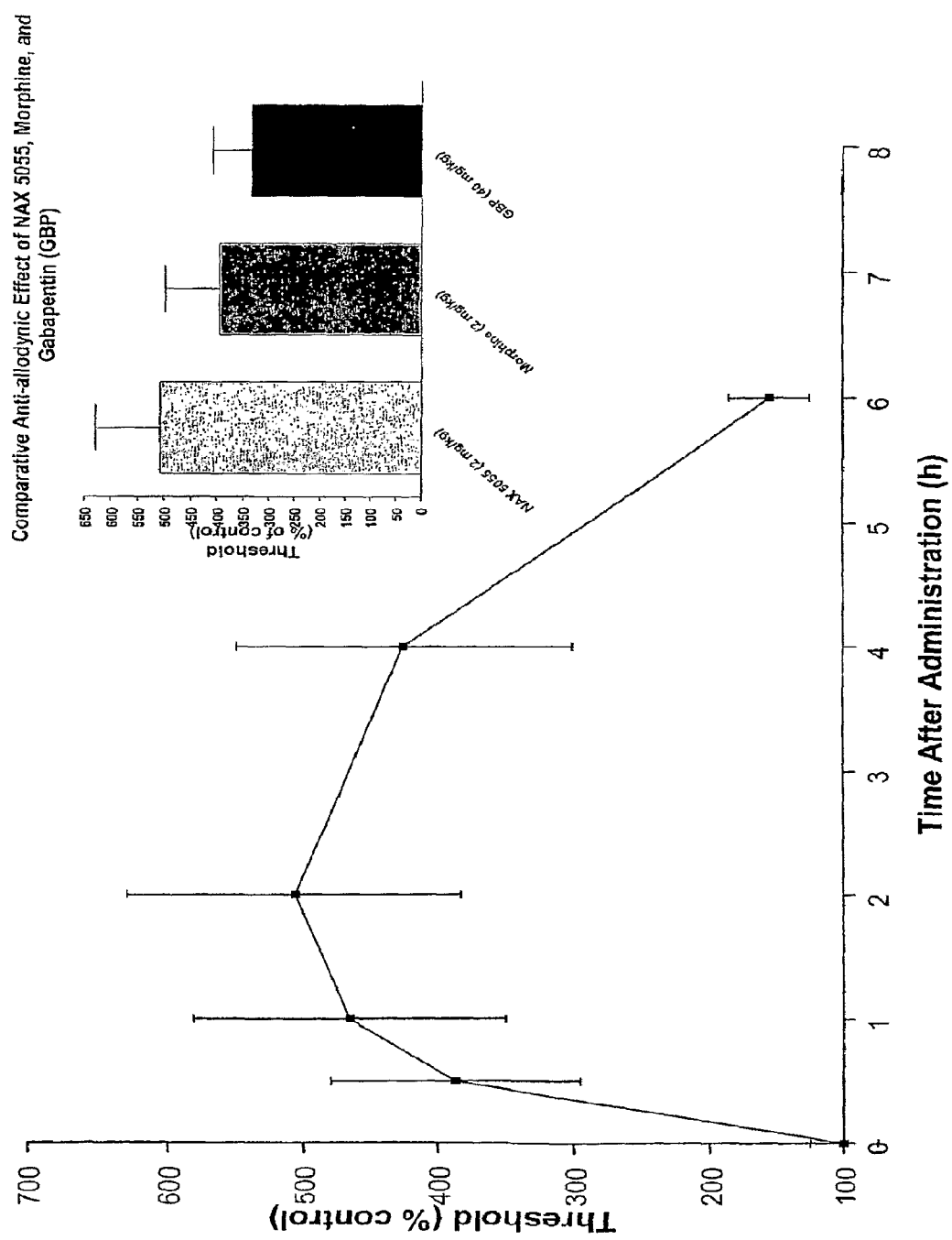

FIG. 18 shows that GAL-BBB2 (labeled as NAX-5055 in the figure) displayed a time-dependent increase in the threshold for mechanical allodynia in the sciatic ligation model of chronic pain. Furthermore, GAL-BBB2 was equi-potent to morphine and several fold more potent that gabapentin.

Figure 19:
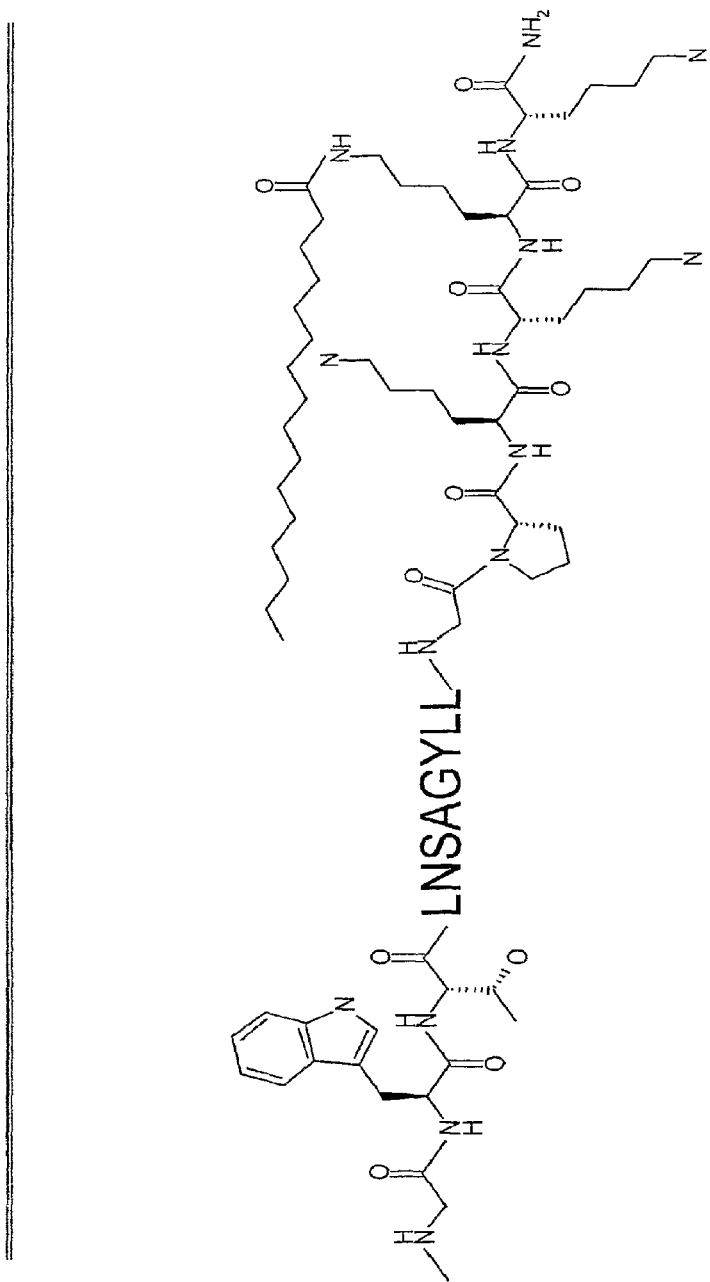

FIG. 19 shows the structure of GAL-BBB2, also referred to as NAX 5055.

Figure 20:
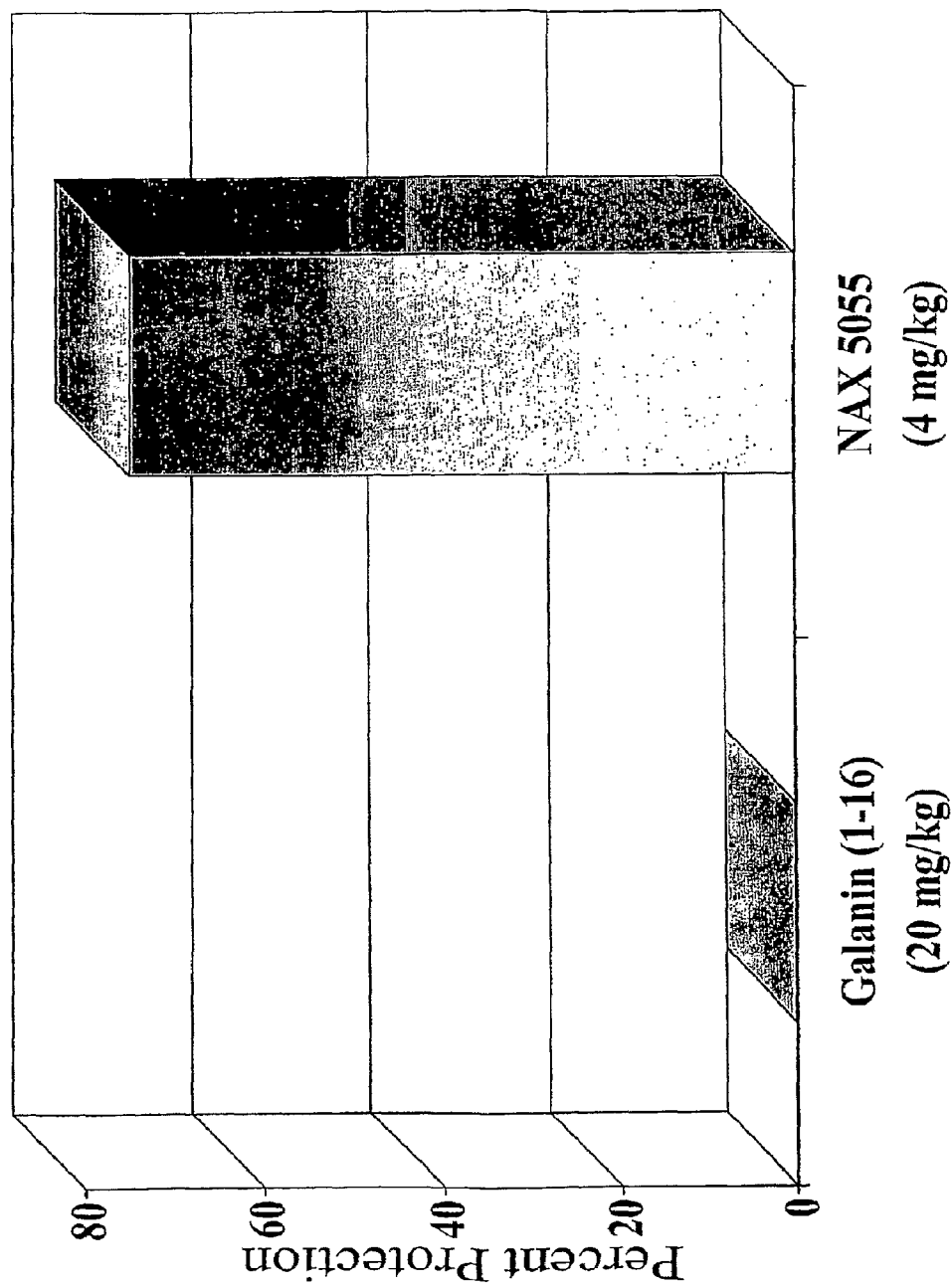

FIG. 20 shows NAX 5055 (GAL-BBB2), but not the native peptide fragment, is active in Frings mouse. Anticonvulsant efficacy was quantitated at the time to peak effect (i.e., 1 h) in a dose-response study. The results of this study demonstrated that GAL-BBB2 displayed a dose-dependent effect against sound-induced seizures. The calculated median effective dose (i.e., ED50) and 95% confidence intervals were obtained from a Probit analysis of the dose-response data was 3.2 (2.3-6.1) mg/kg. The native peptide fragment GAL(1-16) was inactive at a dose of 20 mg/kg, i.p. (six times the ED50 for GAL-BBB2)

Figure 21:
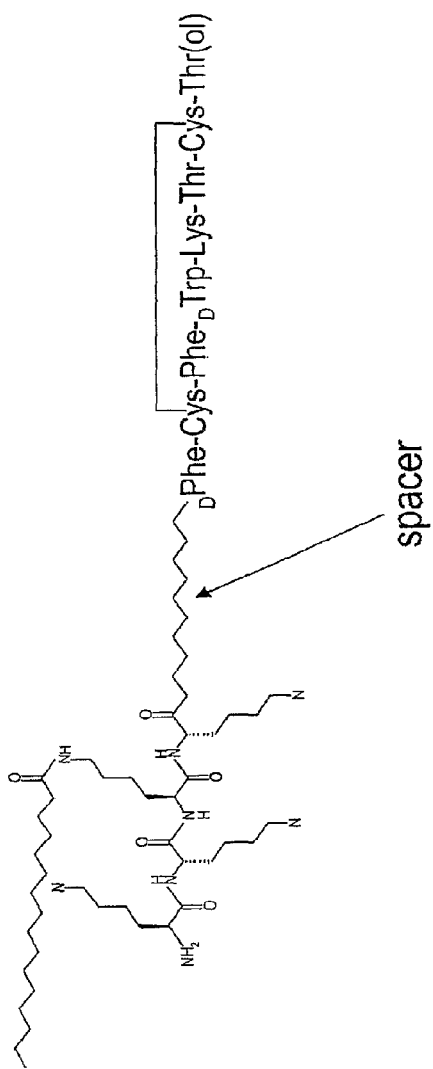

FIG. 21 shows the chemical structure and schematic for engineering octreotide.

Figure 22:
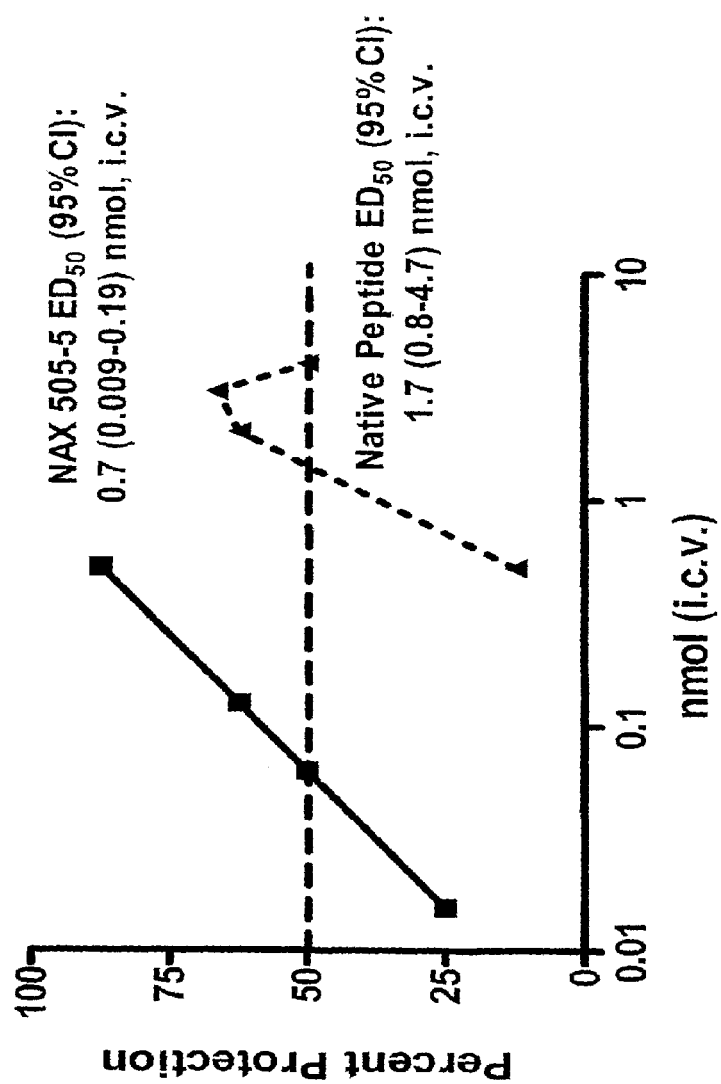

FIG. 22 shows that NAX 5055 (GAL-BBB2) is more potent and more efficacious than the native peptide in 6 Hz (32 mA) test.

Figure 23:
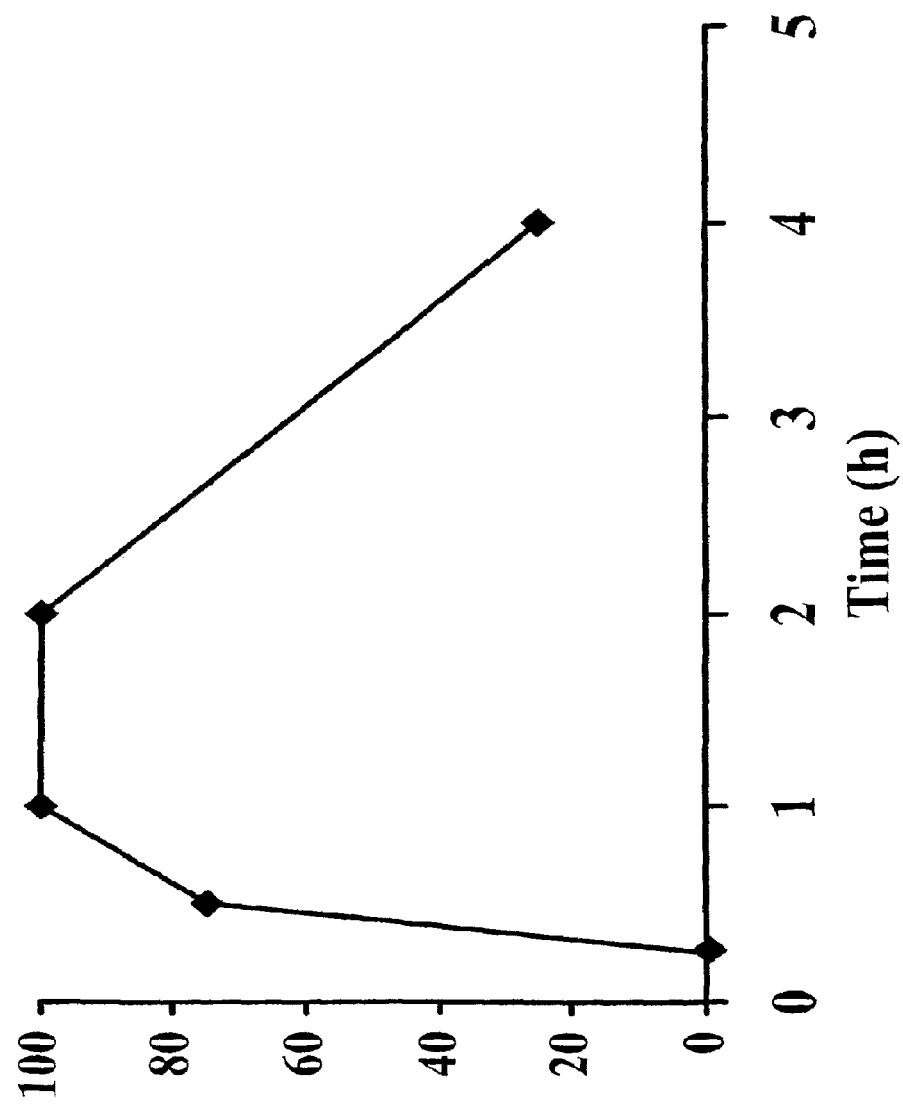

FIG. 23 shows that NAX 5055 (GAL-BBB2) (4 mg/kg, i.p.) displays a time-dependent anticonvulsant activity in Frings Mouse.

Figure 24:
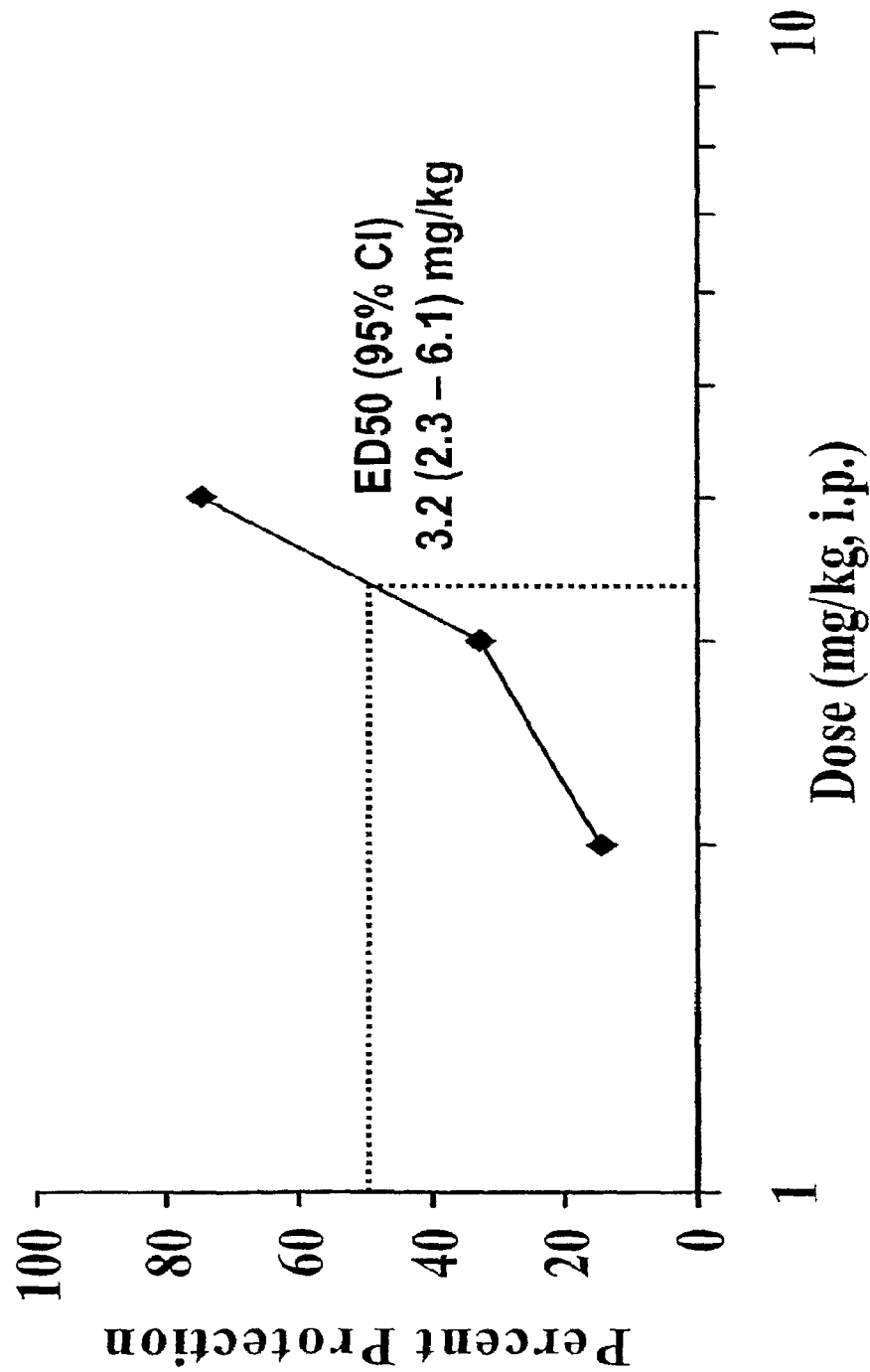

FIG. 24 shows that NAX 5055 (GAL-BBB2) displays dose-dependent protection against audiogenic seizures in the Frings mouse.

Figure 25:
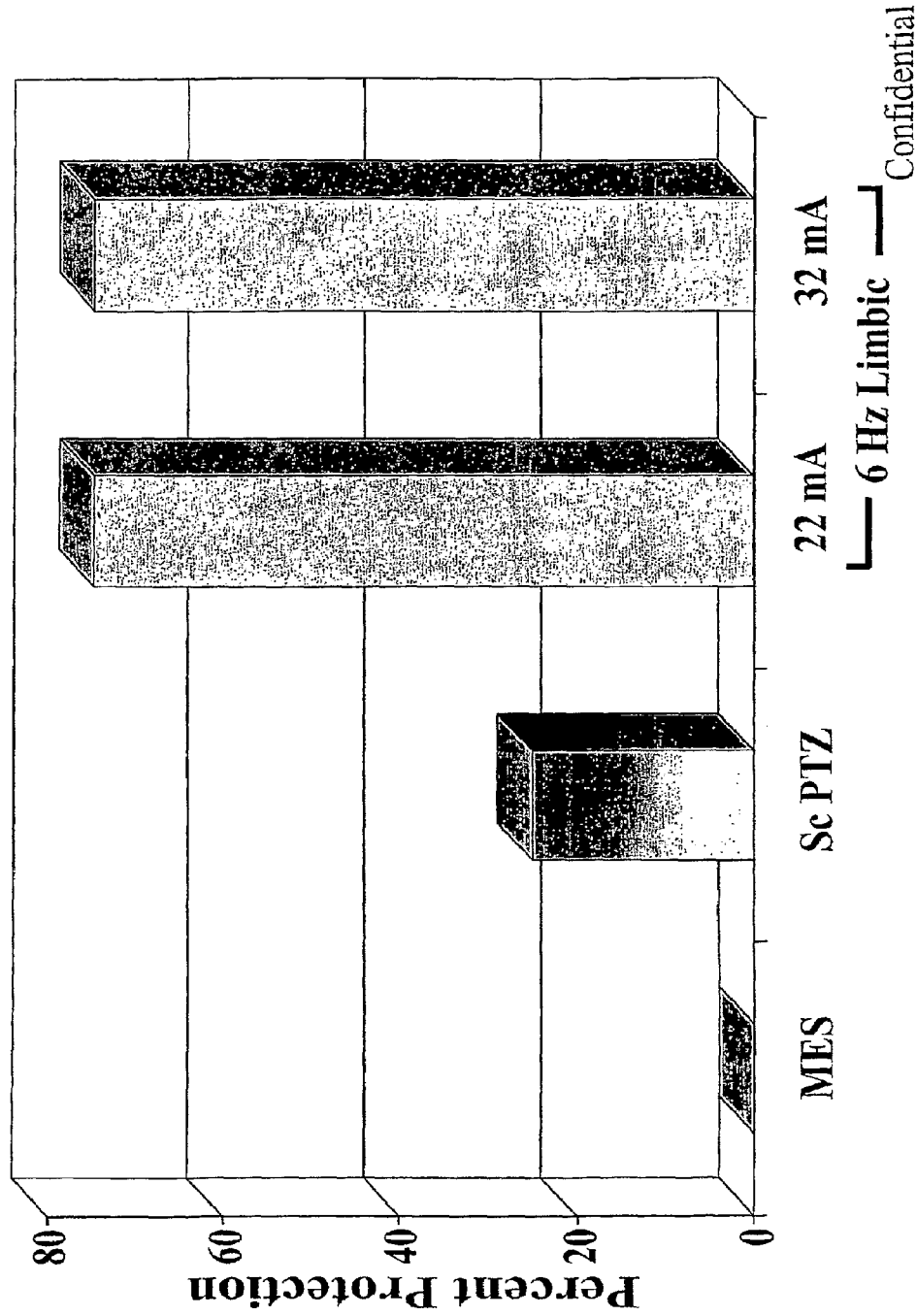

FIG. 25 shows NAX 5055 (GAL-BBB2) (4 mg/kg) is active in pharmaco-resistant seizure model.

Figure 26:
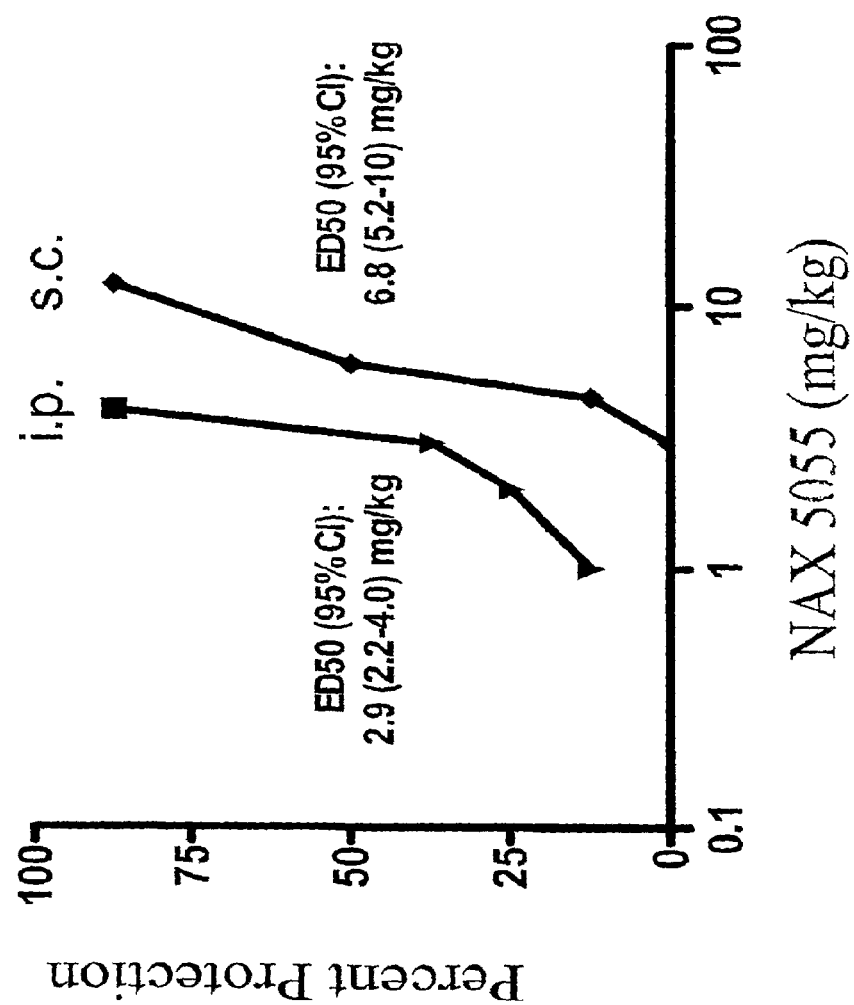

FIG. 26 shows NAX 5055 (GAL-BBB2) displays excellent bioavailability following i.p. and s.c. administration in 6 Hz seizure test. NAX 5055 was injected either intraperitoneally or subcuatenously into groups (n=6-8) male CF-1 mice. After 60 min, individual mice in each group were stimulated (32 mA, 6 Hz, 3 sec duration) via corneal electrodes. Mice not displaying limbic seizures were considered protected. Results demonstrate that the anticonvulsant activity of NAX 5055 is retained following subcutaneous administration. These findings show that a depot formulation amenable for subcutaneous delivery of NAX 5055 and/or other neuroactive peptides can be used.

Figure 27:
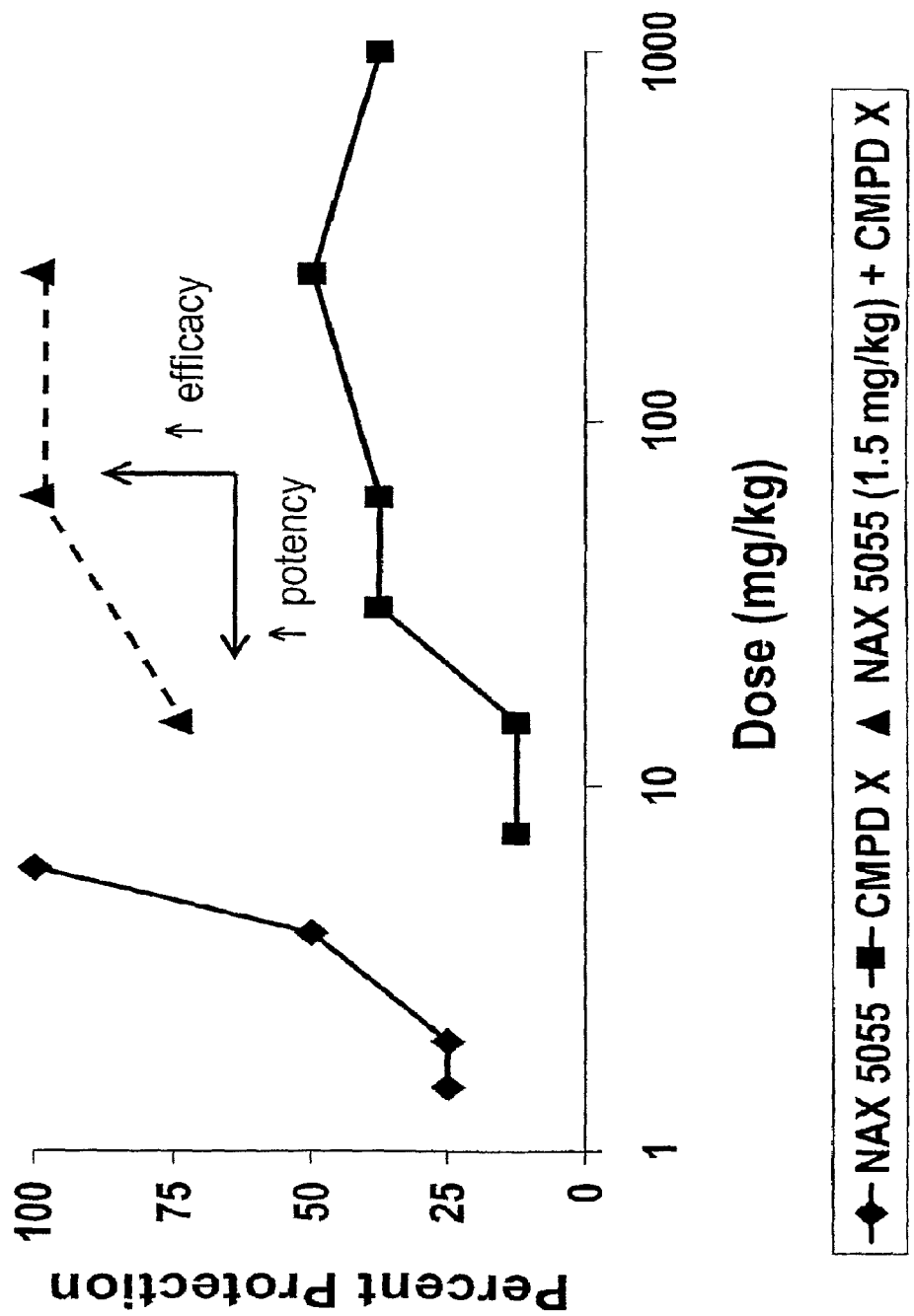

FIG. 27 shows NAX 5055 (GAL-BBB2) increases the efficacy and potency of CMPD X in 6 Hz (44 mA) test. When administered by itself, CMPD A (levetiracetam) is minimally effective against 6 Hz limbic seizures at very high doses (i.e., maximum 50% protection at 1000 mg/kg). In contrast, when a minimally effective dose of NAX5055 (1.5 mg/kg) is administered in combination with CMPDA A (levetiracetam), efficacy and potency is markedly increased. These results show that modulation of galanin receptors by NAX 5055 leads to a synergistic enhancement of the anticonvulsant efficacy of levetiracetam. When taken together, these findings show that a combination product that combines NAX 5055 with levetiracetam can offer therapeutic advantages over even very high doses of levetiracetam alone.

Figure 28:
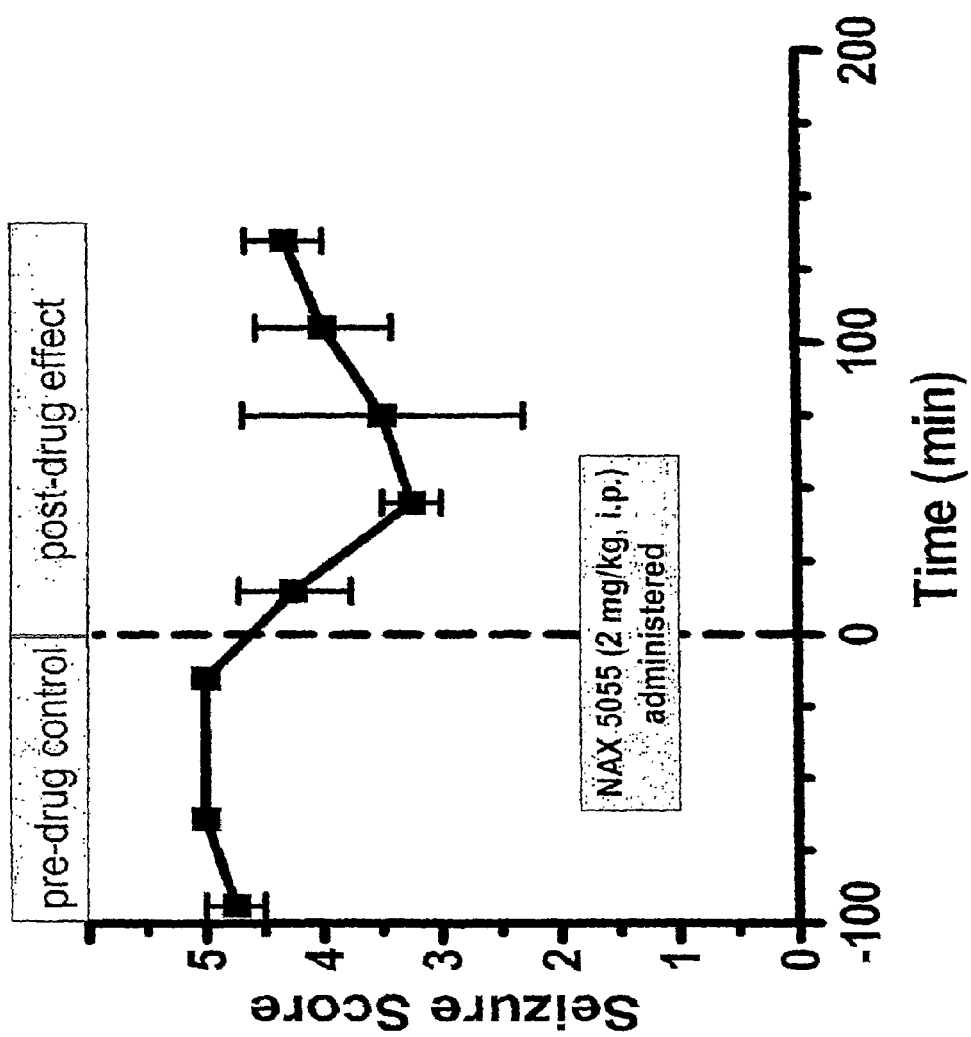

FIG. 28 shows NAX 5055 (GAL-BBB2) displays modest protection in hippocampal kindled rats. In the hippocampal kindled rat model of partial epilepsy, NAX 5055 decreases the seizure score from 5 to 3. These results show that modulation of galanin receptors by NAX 5055 is useful in preventing secondarily generalized partial seizures and is consistent with previous intracerebroventricular studies wherein galanin was directly injected into the brain of kindled rats. The finding that intraperitoneally administered NAX 5055 is active supports the conclusion that it is gaining access to the brain following systemic administration.

Figure 29:
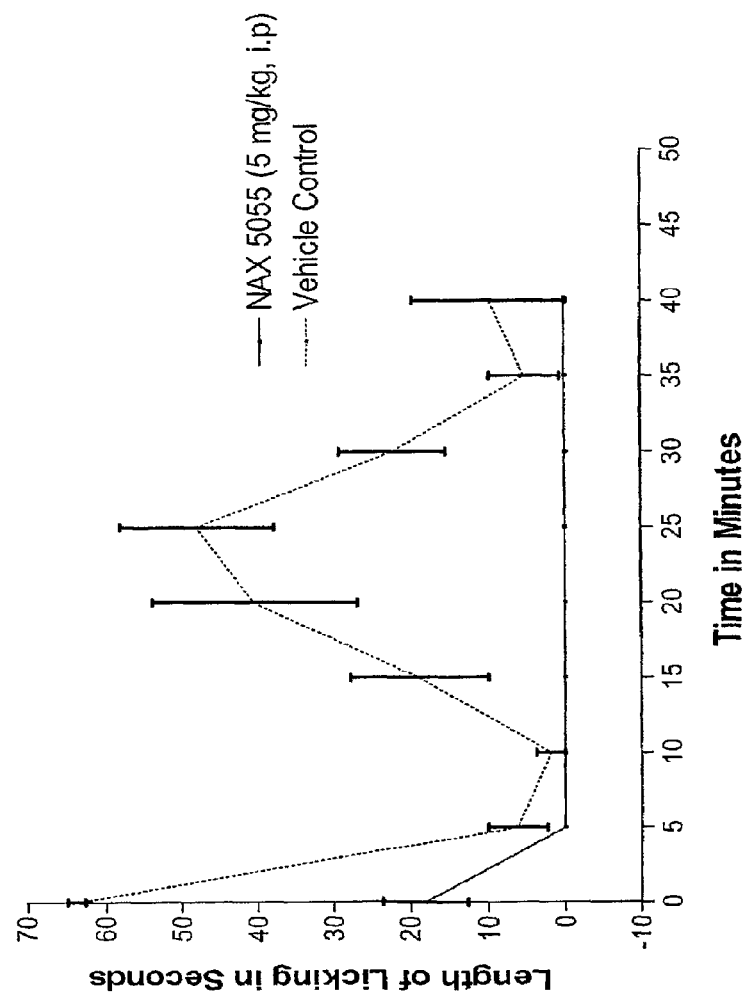

FIG. 29 shows the effect of NAX 5055 (GAL-BBB2) on formalin-induced hyperalgesia. NAX 5055 was administered 60 min prior to plantar injection of formalin. Time was based on anticonvulsant time of peak effect.

Figure 30:
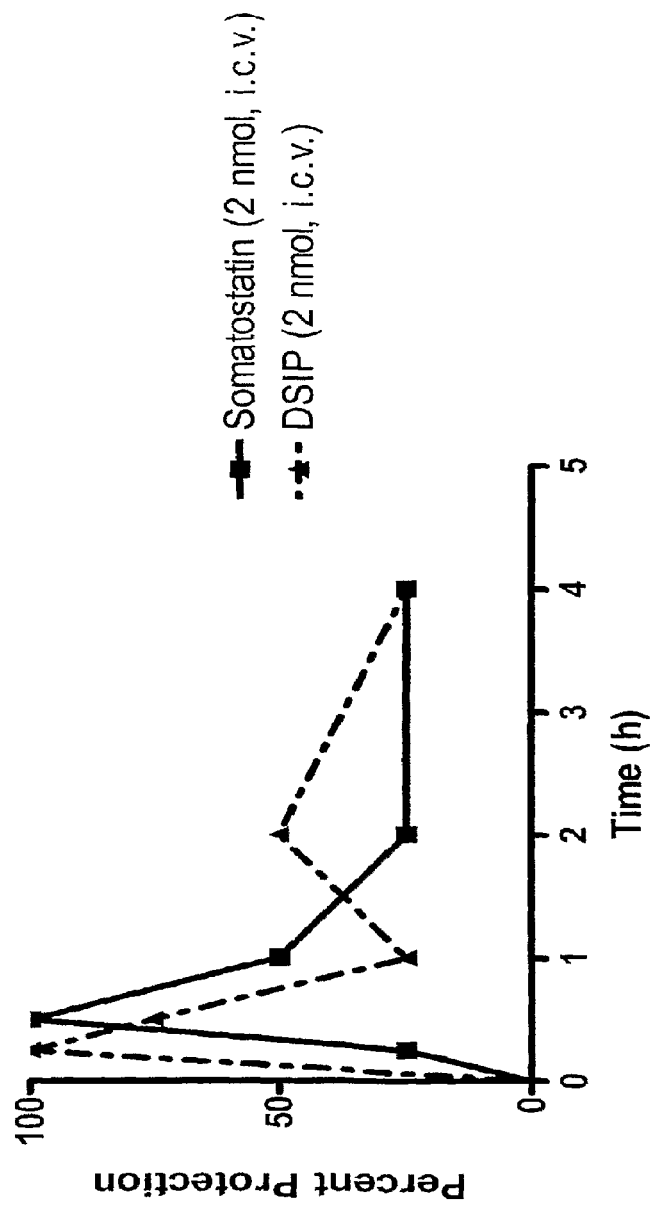

FIG. 30 shows somatostatin and Delta sleep-inducing peptide (DSIP) are both anticonvulsant in 22 mA 6 Hz seizure test. Result shown in this figure demonstrate that somatostatin and delta sleep-inducing peptide (DSIP) when administered directly into the ventricular space of CF-1 mice are effective against 6 Hz (22 mA) limbic seizures. These results provide the 'proof-of-concept' that modulation of somatostatin and DSIP binding sites in the brain is a viable approach. They further support the development of systemically active somatostatin and DSIP neuroactive peptides that cross the blood-brain-barrier using our proprietary technology.

Figure 31:
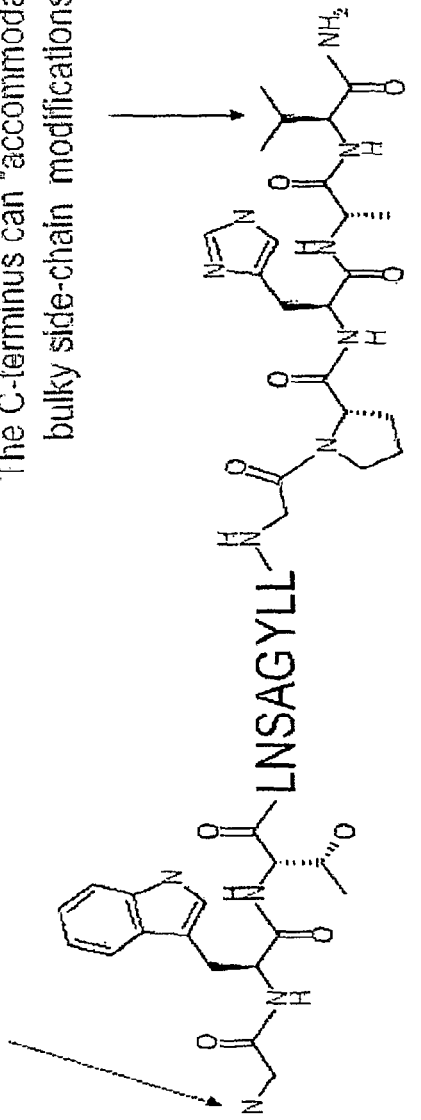

FIG. 31 shows the structure of GAL(1-16) analog. Marked are key pieces of information that were used to design analogs with increased BBB permeability.

Figure 32:
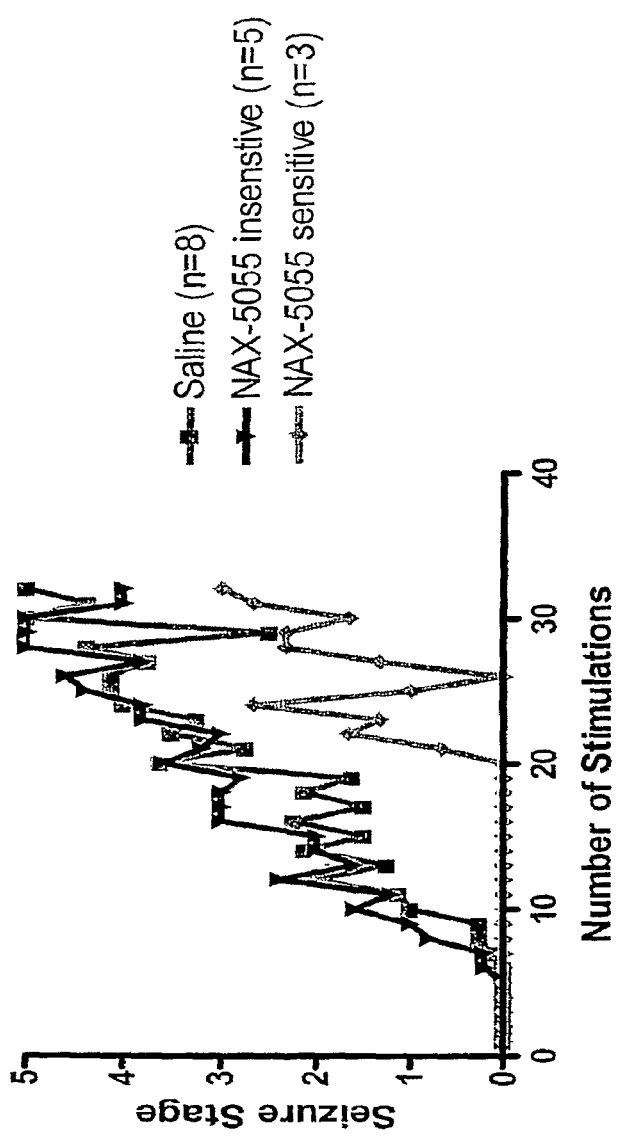

FIG. 32 shows the effect of twice daily injections of NAX-5055 (4 mg/kg, i.p.) on the acquisition of mouse corneal kindling. CF#1 mice were randomized to receive either vehicle (0.9% saline) or NAX-5055. Mice in the NAX-5055 group received two doses of NAX-5055 twelve (12 h) and 1 h prior to their first kindling stimulation. One hour (1 h) prior to each subsequent stimulation, mice in the NAX-5055 treated group received another dose of NAX-5055 (4 mg/kg, i.p.). Mice were stimulated twice daily for 16 days. Results are expressed as the mean seizure score per stimulation. As noted above, the results for the NAX-5055 treated mice segregated into two populations; i.e., sensitive (green line) and insensitive (blue line). Saline vs. NAX-5055 sensitive significantly different at $p<0.0002$; NAX-5055 sensitive vs. NAX-5055 insensitive significantly different at $p<0.0001$. The results obtained for this study support the claim that galanin-based peptides such as NAX-5055 possess the ability to prevent the acquisition of kindling and can be disease-modifying in patients at risk for the development of epilepsy and other neurological disorders.

Figure 33:
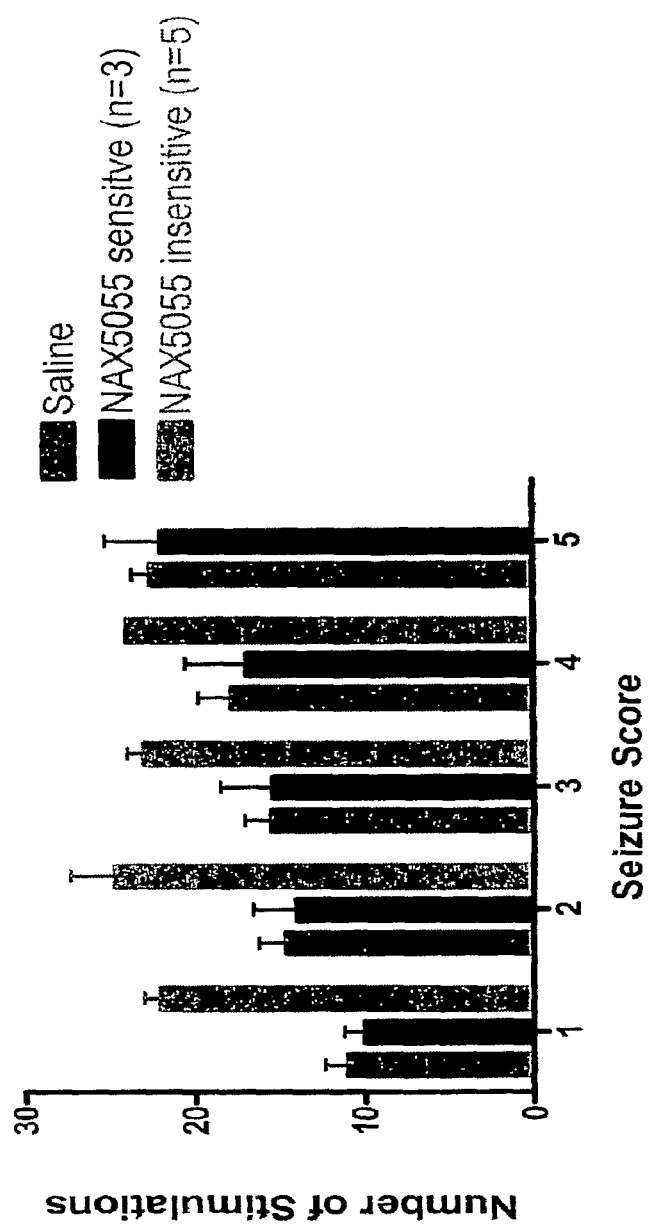

FIG. 33 shows the effect of twice daily treatment with NAX-5055 (mg/kg, i.p.) on the rate of corneal kindling. Mice treated with NAX-5055 (see legend to Figure X for experimental details) segregated into two treatment groups; i.e., NAX-5055 sensitive and NAX-5055 insensitive. Results are expressed as the number of stimulations required to reach a particular seizure score+/−S.E.M.; i.e., 1 to 5. Mice in the NAX-5055 sensitive group required two times more stimulations to reach a Stage 1 seizure and 35-40% more stimulations to reach Stage 2 and Stage 3 seizures, respectively. Furthermore, none of the mice in the NAX-5055 sensitive group reached Stage 5 seizures. One Way ANOVA, $p<0.0209$; post hoc analysis: saline vs. NAX-5055 insensitive, $p>0.05$; NAX-5055 sensitive vs. NAX-5055 insensitive, $p<0.05$. These results support the conclusion that modified galanin-based neuropeptides possess the ability to modify the development of kindling acquisition and that they are useful for the prevention of network hyperexcitability in a patient population susceptible to developing epilepsy and other neurological disorders.

Figure 34:
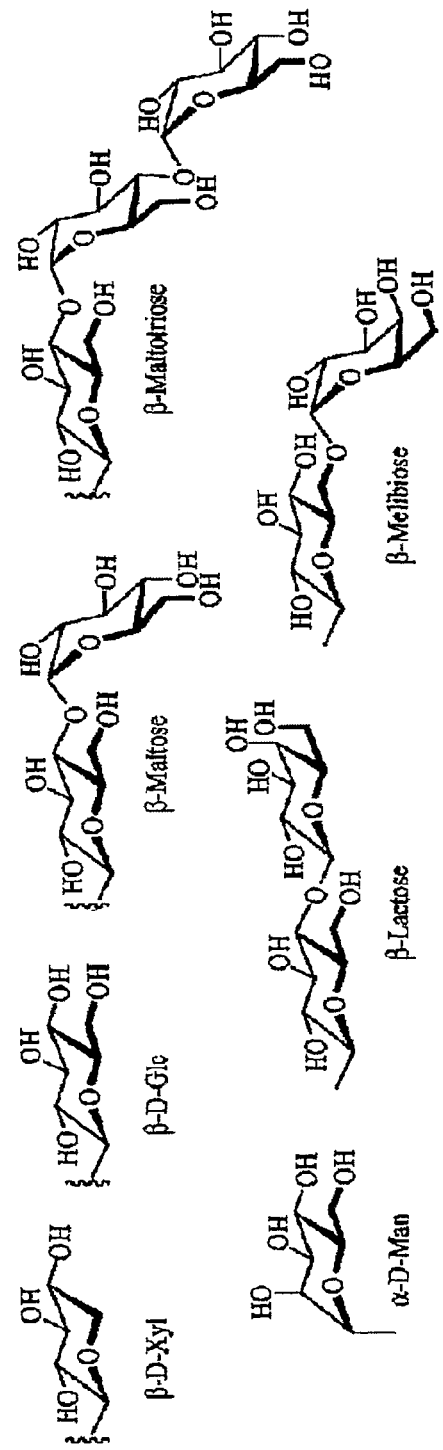

FIG. 34 shows structures of glycosyl groups introduced to enkephalin analogs (Elmagbari, Egleton et al. 2004).

FIG. 35 shows that the combination of two distinct chemical modifications is superior over individual modifications. Cationization or lipidization alone did not improve penetration of the 5055 analog as a combination of both.

Figure 36:
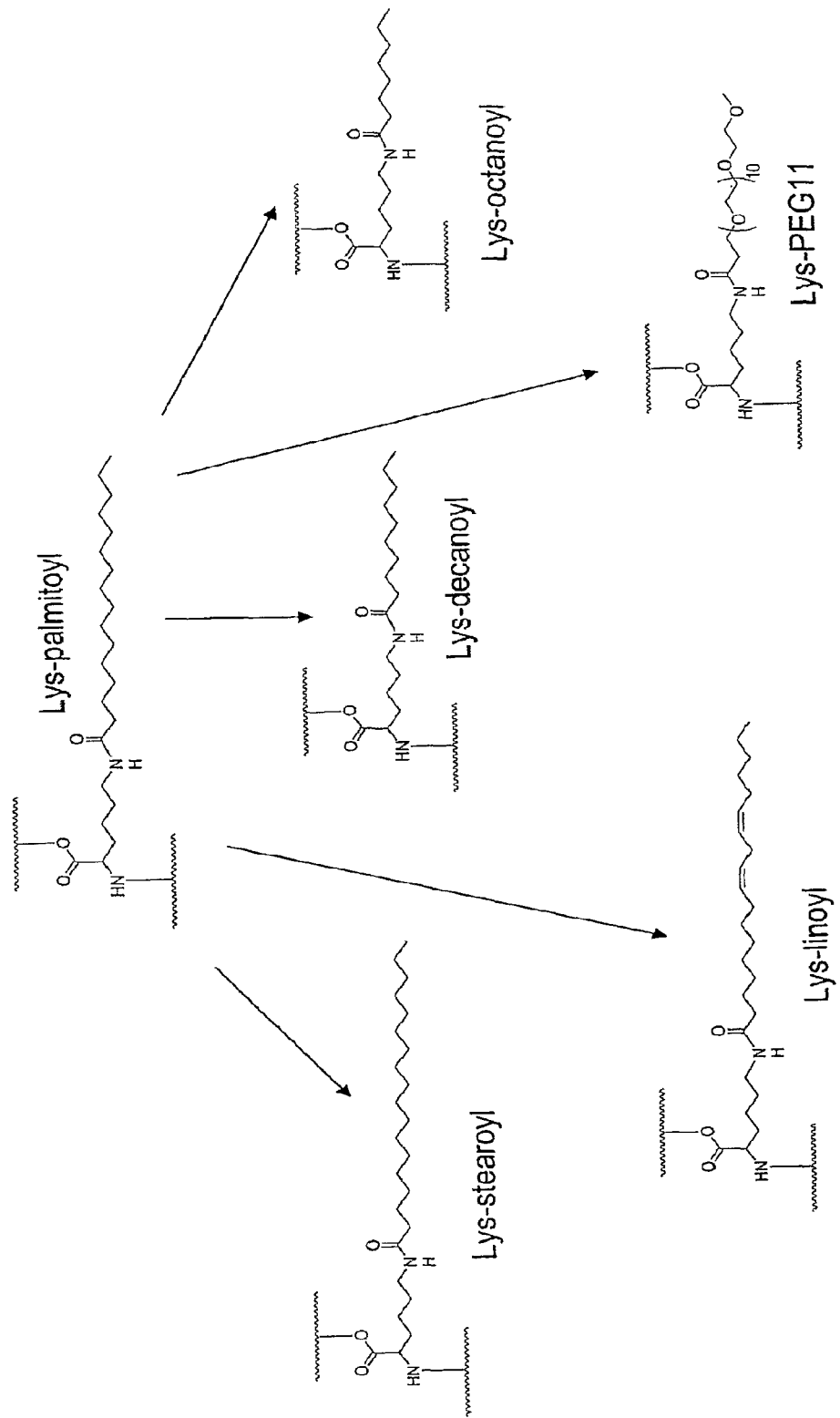

FIG. 36 shows examples of lipoamino acids which were used to improve permeability of peptides through the blood-brain-barrier. Such lipoamino acids can be combined with chemical modifications that increase basicity of the target peptide.

Figure 37:
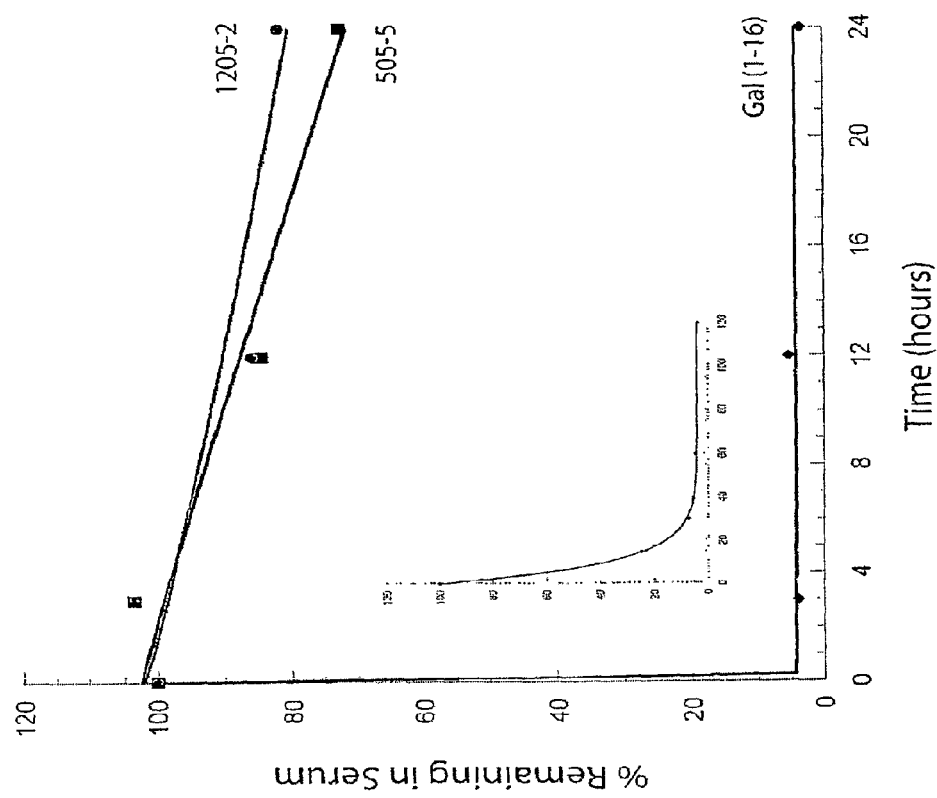

FIG. 37 shows chemical modifications improve metabolic stability of the neuropeptide analogs. Analogs 5055 (SEQ ID NO: 3) or 1205-2 (SEQ ID NO: 50) or unmodified analog Gal(1-16) were incubated in diluted rat serum at 37° C. Remaining amounts of the peptides were determined by HPLC.

Figure 38:
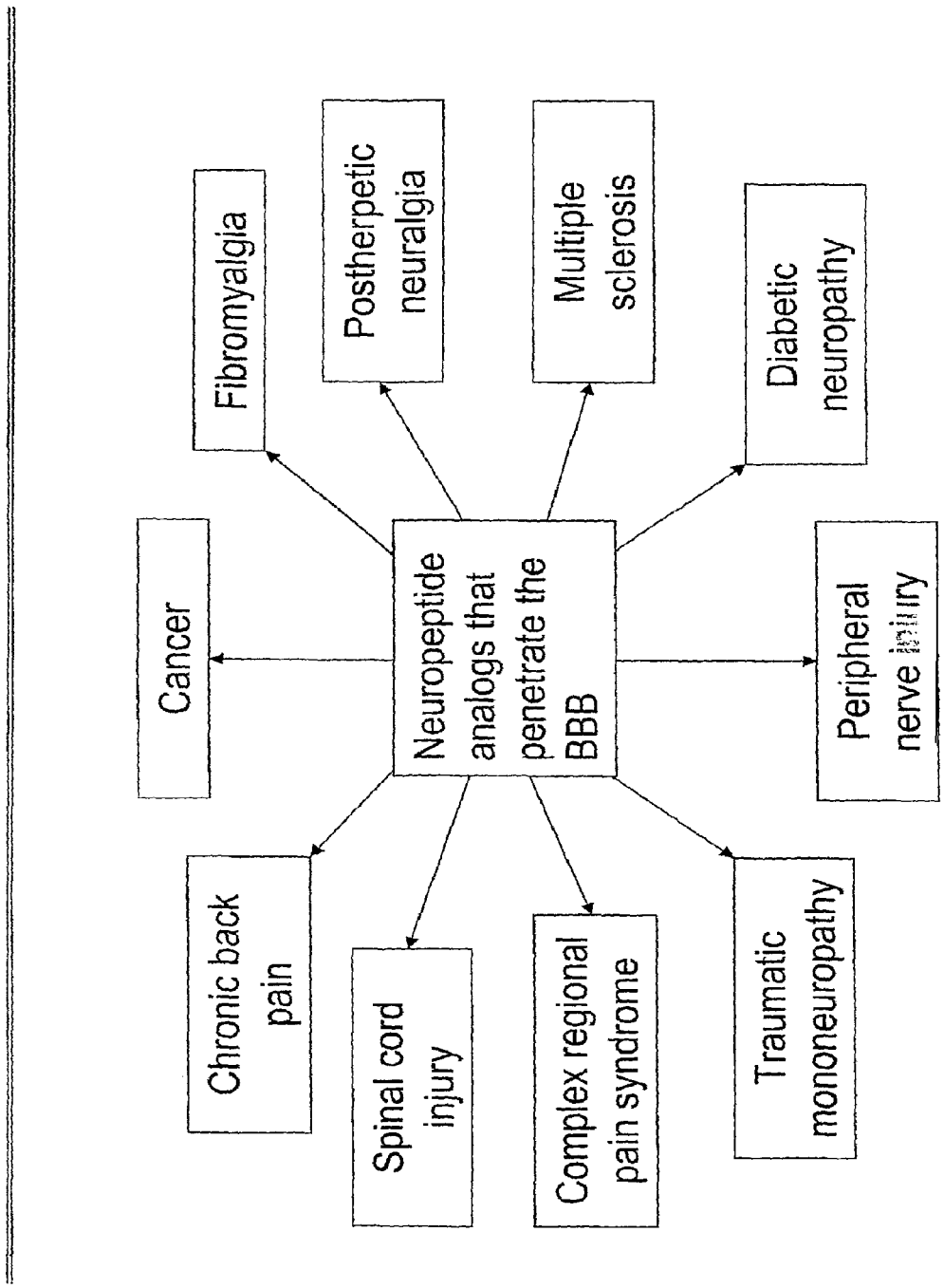

FIG. 38 shows the different types of neuropathic pain can be treated, prevented or reversed by neuropeptide analogs that cross the BBB.

III. DETAILED DESCRIPTION

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

B. COMPOSITIONS AND METHODS

1. The Blood-Brain Barrier

The blood-brain barrier (BBB) is the specialized system of capillary endothelial cells that protects the brain from harmful substances in the blood stream, while supplying the brain with the required nutrients for proper function. Unlike peripheral capillaries that allow relatively free exchange of substance across/between cells, the BBB strictly limits transport into the brain through both physical (tight junctions) and metabolic (enzymes) barriers. Thus the BBB is often the rate-limiting factor in determining permeation of therapeutic drugs into the brain.

A number of obstacles currently limit the use of many compounds for use as central nervous system (CNS) therapeutic agents. First, the brain is equipped with a barrier system. The brain barrier system has two major components: the choroid plexus and the blood-brain barrier (BBB). The choroid plexus separates cerebrospinal fluid (CSF) from blood and the BBB separates brain ISF from blood.

Also, the BBB has about 1000 times more surface area than the choroid plexus and is the primary obstacle to delivery of therapeutic compounds to the CNS. The BBB acts as a selective partition, regulating the exchange of substances, including peptides, between the CNS and the peripheral circulation. The primary structure of the BBB is the brain capillary endothelial wall. The tight junctions of brain capillary endothelial cells prevent circulating compounds from reaching the brain TSF by the paracellular route. Furthermore, recent work suggests the existence of a physiological barrier at the level of the basal lamina, in addition to the barrier provided by the tight junctions. (Kroll et al., Neurosurgery, Vol. 42, No. 5, p. 1083 (May 1998)). Other unique characteristics of the BBB include lack of intracellular fenestrations and pinocytic vesicles and a net negative charge on the luminal surface of the endothelium.

The mechanisms by which substances may traverse the BBB may generally be divided into active and passive transport mechanisms. Lipophilic molecules readily traverse the BBB by passive transport or diffusion through the endothelial plasma membranes. Hydrophilic molecules, such as peptides, typically require an active transport system to enable them to cross the BBB. Certain larger peptides, such as insulin, have receptors on the luminal surface of the brain capillaries which act as active transcytosis systems.

There are two main mechanisms for transporting peptides across the blood-brain barrier: (1) simple diffusion through the membrane, determined primarily by molecular size and lipophilicity, and (2) active influx, mediated by specific receptors and carriers located on the surface of the endothelial cells in the blood-brain barrier, or by non-specific absorption trancytosis (Tamai and Tsuji, 2000; Pan and Kastin, 2004a; Smith et al., 2004).

2. Improving Permeability

A number of strategies have been tested to improve permeability of peptides and proteins through the blood-brain barrier. These can be divided into several categories: (1) conjugation to a vector or nutrient-active transport that enhances uptake of the peptide into the CNS; (2) lipidization/halogenation resulting in increased lipophilicity to enhance simple diffusion, (3) cationization (increased basicity) to enhance transport through absorptive transcytosis; and (4) glycosylation or prodrugs that improve active/passive transport and the pharmacokinetic profiles of peptides ((Witt et al., 2001) and (Pan and Kastin, 2004a)). Examples of such studies and major findings are shown in Table 1. Each reference is herein incorporated in its entirety for its teaching regarding penetration of the blood-brain barrier.

TABLE 1

Examples of improving permeability of peptides through the blood-brain barrier.

| Strategy | Peptides | Major Findings | References |
| --- | --- | --- | --- |
| Halogenation of aromatic residues | Enkephalins | Chloro-Phe containing peptides elicited a much greater analgesic effect after intravenous administration | (Weber et al., 1991; Abbruscato et al., 1996) |

TABLE 1-continued

Examples of improving permeability of peptides through the blood-brain barrier.

| Strategy | Peptides | Major Findings | References |
| --- | --- | --- | --- |
| Conjugation with lipoamino acids | α-Conotoxin MII | 4-fold Increase in blood-brain barrier permeability | (Blanchfield et al., 2003) |
| Conjugation with polyamine derivatives | β-Amyloid-derived peptide | 7-fold increase in the blood-brain barrier permeability | (Poduslo et al., 1999) |
| Conjugation with DOPA/DTPA derivatives | Octreotide/ somatostatin Epidermal growth factor | More efficient brain uptake of radiopharmaceuticals for MRI and treatment of brain tumors | (Luyken et al., 1994; Kurihara and Pardridge, 1999) |
| Glycosylation | Enkephalins | Adding glycosyl moiety resulted in 20-fold increase in systemic bioavaliability | (Elmagbari et al., 2004) |
| Selective amino-acid side-chain replacements | Neurotensin | Trp replaced by Neo-Trp and Ile replaced by Tert-Leu resulted in an analog that crosses blood-brain barrier | (Hertel et al., 2001) |
| Selective amino-acid side-chain replacements | Thyrotropin-releasing hormone (TRH) | His replaced by pyridinium moiety increased 2- to 3-fold central activity of TRH | (Prokai et al., 2004) |
| Prodrug strategy | TRH-like peptides | Esterification of Glu residues enhanced analeptic activity | (Prokai-Tatrai et al., 2003) |
| Prodrug strategy | Enkephalin | C-terminal Extension with Phe increased half-life and permeability | (Greene et al., 1996) |
| Prodrug strategy | Enkephalin | Conjugation with adamantine moiety resulted in improved activity in subcutaneous administration | (Kitagawa et al., 1997) |
| Vector-mediated delivery | Enkephalin Dalargin | SynB3 peptide-based vectors enhanced brain uptake and analgesic activity | (Rousselle et al., 2003) |

Regarding the first item, conjugation, the increased molecular size of the conjugated peptides does not seem to hamper permeability. Adding the peptide-based vector SynB1 (MW=2,099) to the opioid peptide dalargin (MW=726) resulted in an almost four-fold increase in size, but also in an 18-fold increase in brain uptake (Rousselle et al., 2003). Similarly, adding disaccharide moieties to enkephalin analogs increased their antinociceptive activity up to 21-fold, following intravenous administration (Elmagbari et al., 2004).

Two important factors, namely lipophilicity and basicity, contribute to increased permeability of peptides through the blood-brain barrier without the need for specific transporters or carriers. The lipophilic character of a peptide can be altered by either conjugation to a hydrophobic moiety (e.g., poly-aliphatic chains), or halogenation of aromatic residues (e.g., chloro-Phe, as compared to Phe). It has been shown that polyamine-modified proteins and peptides cross the blood-brain barrier more efficiently, as compared to unmodified ones (Poduslo and Curran, 1996a; b; Poduslo et al., 1999). It has also been shown (Tamai et al., 1997) that the increased basicity of small peptides was an important determinant of transport through the blood-brain barrier via absorptive-mediated endocytosis (AME).

In addition to direct modification of the peptides, there are a few other drug delivery strategies with improved uptake of drugs into the CNS. These include liposome-, micelle- or nanoparticle-mediated delivery of peptides through the blood-brain barrier (Kreuter et al., 2003; Pan and Kastin, 2004b). These novel drug delivery technologies can also be applicable to neuropeptide-based compositions disclosed herein and known in the art.

Figure 6:
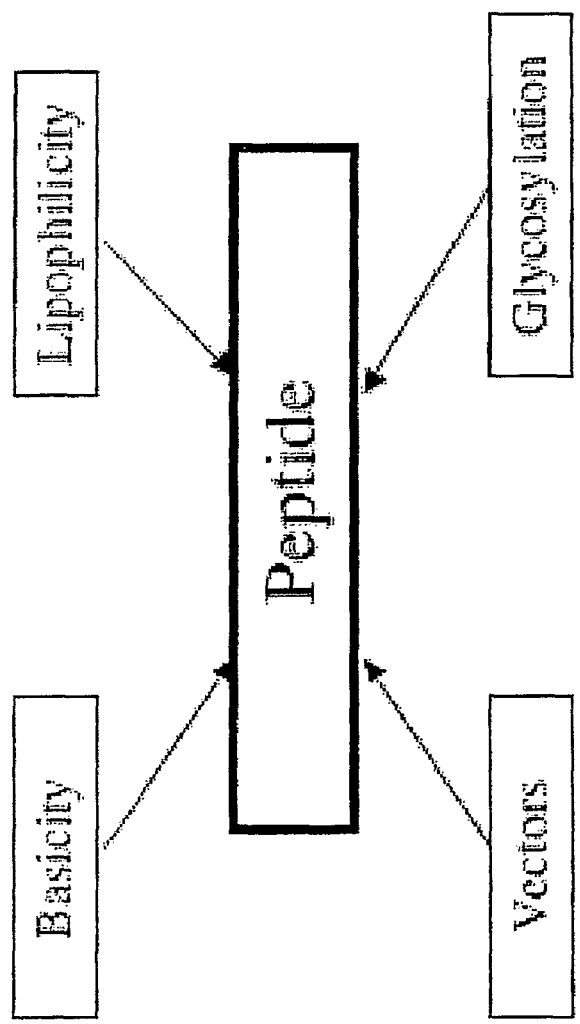
FIG. 6 shows key factors affecting permeability of peptides through the blood-brain barrier. Basicity and lipophilicity may improve the passive transport via diffusion and absorptive-mediated endocytosis, whereas glycosylation or vectors can also contribute to the active transport through the blood-brain barrier.

There are several peptide-engineering strategies to improve permeability of neuropeptides through the blood-brain barrier. These are summarized in FIG. 6. However, none of the studies mentioned above showed a systematic approach of combining these strategies to further boost the permeability of the peptides through the blood-brain barrier. What is disclosed herein is the application of these peptide-engineering strategies in combination to known anticonvulsant neuropeptides, such as somatostatin or galanin, thereby making these peptides anticonvulsant via the intravenous (i.v.) or subcutaneous (s.c.) route of administration.

Disclosed herein are methods and compositions for increasing permeability through the blood-brain barrier. By "increasing" is meant a higher percentage of the composition is able to cross the blood-brain barrier compared with the wild type, non-altered, or native peptide, or with a control composition. For example, the rate of increase can be 1, 2, 3, 4, 5, 6, 7, 8, 9, 10, 11, 12, 13, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 percent when compared with the control, native, or wild type peptide or composition.

Figure 7:
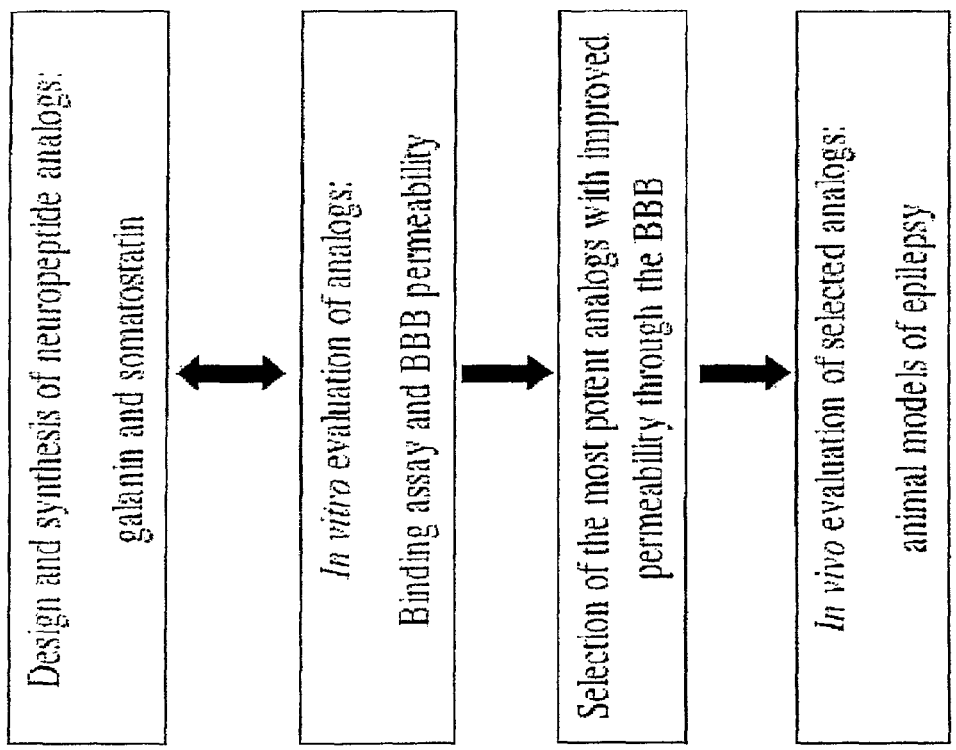
FIG. 7 shows a general strategy for the development of neuropeptide analogs with anticonvulsant activity. Two model neuropeptides were selected to evaluate the technology for improving their permeability though the blood-brain barrier.

Specifically disclosed herein is a composition with increased permeability of the blood-brain barrier, wherein the composition comprises a peptide with increased lipophilic character and increased basicity when compared to the non-altered form of the peptide (FIG. 7). Also disclosed are compositions with increased permeability of the blood-brain barrier, wherein the composition comprises a peptide with increased lipophilic character, increased basicity, and increased glycosylation when compared to the non-altered form of the peptide.

Also disclosed herein are methods of increasing permeability of the blood-brain barrier for a peptide, comprising increasing lipophilic character and increasing basicity of the peptide compared to the non-altered form of the peptide. Another method of increasing permeability of the blood-brain barrier for a peptide, comprises increasing lipophilic character, increasing basicity, and increasing glycosylation of the peptide compared to a non-altered form of the peptide.

a) Lipophilic Character

The lipophilic character of the composition can be increased by conjugating the peptide to a hydrophobic moiety, for example. Examples of hydrophobic moieties include, but are not limited to, polyaliphatic chains or aromatic residues. The lipophilic character can also be increased by increasing halogenation of aromatic residues or polyaliphatic reagents, such as perfluorohexanoic acid b) Basicity

The basicity of the composition can be increased by introducing homo- and heterooligomers of positively charged amino acid residues, including, but not limited to Lysine, Arginine, homo-Lysine, homo-Arginine, Ornitine in L- or D-isomer configuration; 2,3-Diaminopropioic acid; 2,4-Diaminobutric acid.

The basicity can also be increased by conjugation to polyamine-based moieties, such as spermine, spermidine, polyamidoamine dendrimers or polyamine toxins and derivatives thereof.

c) Glycosylation

The glycosylation can be introduced by conjugation to xylose, glucose, galactose, maltose, maltotriose, mannose, lactose, melibiose or similar saccharides.

d) Vectors

Also disclosed are vectors comprising the compositions disclosed herein. An example of vectors able to cross the BBB can be found in Toyobuku et al. (J Pharmacol Exp Ther. 2003 April; 305(1):40-7.),

C. METHODS OF TREATMENT

Disclosed herein are methods of treating specific diseases and disorders involving the central nervous system, or any application that involves the need for a compound to cross the blood-brain barrier. A variety of diseases and disorders can be treated with the methods and compositions disclosed herein, including stroke and related ischemic diseases, chronic back pain, spinal cord injuries, peripheral nerve injuries, traumatic brain injuries, retinal degeneration, neurodegenerative disorders, cataracts, antibiotic-induced ototoxicity, Alzheimer's disease, Amyotrophic Lateral Sclerosis (ALS, Lou Gehrig's disease), epilepsy (such as generalized, partial, or refractory epilepsy), Huntington's disease, Parkinson's disease, Multiple Sclerosis, chronic back pain, fibromyalgia, postherpetic neuralgia, diabetic neuropathy, traumatic mononeuropathy, complex regional pain syndrome, adjuvant analgesic, rhizotomy/nerve ablation, preamptive analgesia/amputations, epileptogenesis/trauma, chemical exposure, status epilepticus, chemotherapy-induced neuropathy, cancer, opioid withdrawal, and chronic neuropathic pain. Methods and routes of administration, dosages, and pharmaceutical compositions are discussed in more detail below.

Regarding the use of the compositions disclosed herein to treat spinal cord injury and multiple sclerosis, the following references are hereby incorporated in their entirety for their teaching concerning the treatment of these diseases: Hawes J J, Narasimhaiah R, Picciotto M R Galanin and galanin-like peptide modulate neurite outgrowth via protein kinase C-mediated activation of extracellular signal-related kinase. Eur J. Neurosci. 2006 June; 23(11):2937-46. Suarez V, et al, The axotomy-induced neuropeptides galanin and pituitary adenylate cyclase-activating peptide promote axonal sprouting of primary afferent and cranial motor neurons Eur J. Neurosci. 2006 September; 24(6):1555-64

The compositions and methods disclosed herein can also be useful in preventing anoxic damage, increasing growth hormone secretion in humans, controlling prolactin release from pituitary adenomas, prolonging morphine analgesia, as an antidepressant, and in feeding disorders, for example.

Also disclosed are methods of treating pain and other neurological disorders comprising administering to a subject in need thereof an effective amount of the polypeptides disclosed herein.

The methods and compositions disclosed herein can also be used in the prevention, amelioration, or treatment of neurological disorders, such as those disclosed above and known to those of skill in the art.

The methods and compositions disclosed herein can be used in conjunction with other compositions or treatment methods. For example, the following drugs and classes of drugs can be used in combination with the compositions disclosed herein for pain, epilepsy, neuroprotection, and depression, bipolar, other psychiatric disorders, as well as for any other disease or disorder treatable by the compositions disclosed herein: opioids and opioid peptides, morphine, hydroxymorphine, fentanyl, oxycodone, codeine; capsaicin; as well as antiepileptic drugs as a class including but not limited to carbamazepine, primidone, gabapentin, pregabalin, diazepam, felbamate, fluorofelbamate, lamotrigine, lacosamide, levetiracetam, phenobarbital, phenyloin, fosphenyloin, topiramate, valproate, vigabatrin, zonisamide, oxcarbazepine, nonsteroidal anti-inflamatory drugs (NSAIDs), local anesthetics (such as lidocaine), glutamate receptor antagonists, NMDA antagonists, alpha-adrenoceptor agonists and antagonists, adenosine, cannabinoids, NK-1 antagonist (CI-1021), antidepressants (amitriptyline, desipramine, imipramine, for example), analogs and derivatives of galanin, somatostatin, delta-sleep inducing peptide, enkephalins, oxytocin. cholecystikinin, calcitonin, cortistatin, nociceptin and other neuropeptide-based therapeutics, and pluronic P85 block copolymer.

The following drugs and classes of drugs can be used in combination with the compositions disclosed herein for Alzheimer disease: amyloid lowering agents, such as Flurizan; galantamine (Razadyne); rivastigmine (Exelon); donepezil (Aricept); tacrine (Cognex); memantine (Namenda); and vaccine for Alzheimer's disease. Also disclosed are methods of treating a subject in need of a composition that crosses the blood-brain barrier, comprising identifying the composition to be used in treatment of the subject; modifying the composition by increasing lipophilicity and basicity of the composition; and administering the modified composition to the subject in need thereof.

By "combination" is meant one or more additional compositions, in addition to the compositions disclosed herein, can be administered to the subject. These compositions can ben Also disclosed are methods of treating a subject in need of a composition that crosses the blood-brain barrier, comprising: identifying the composition to be used in treatment of the subject; modifying the composition by increasing lipophilicity, glycosylation, and basicity of the composition; and administering the modified composition to the subject in need thereof.

Also disclosed are methods of treating a subject in need of a composition that crosses the blood-brain barrier, comprising identifying the composition to be used in treatment of the subject; modifying the composition by increasing lipophilicity, glycosylation, and basicity of the composition; inserting the modified composition into a vector; administering the vector to the subject in need thereof.

Also disclosed is a method of treating a subject in need of a composition that crosses the blood-brain barrier, comprising: identifying the composition to be used in treatment of the subject; modifying the composition by increasing lipophilicity and basicity of the composition; inserting the modified composition into a vector; and administering the vector to the subject in need thereof.

1. Methods of Using the Compositions as Research Tools

The disclosed compositions can be used in a variety of ways as research tools. For example, the disclosed compositions, such as SEQ ID NOs: 1-55, can be used as reagents to study epilepsy, for example.

The compositions can be used, for example, as targets in combinatorial chemistry protocols or other screening protocols to isolate molecules that possess desired functional properties, such as galanin agonists or antagonists or partial agonists.

The compositions can be used to discover individual and network interactions between different neuropeptides, other neurotransmitters, receptors and ion channels in the nervous system. For example, the disclosed compositions can be used to discover synergistic interactions between galanin receptor antagonists and drugs that act on molecular targets expressed on the same neurons. Such positive drug-drug interactions are beneficial, since they can improve efficacy or/and safety of a treatment when two drugs are applied in combination.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

2. Methods of Gene Modification and Gene Disruption

The disclosed compositions and methods can be used for targeted gene disruption and modification in any animal that can undergo these events. For example, a gene producing galanin can be altered to express a galanin analog with increased permeability of the blood-brain barrier. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination event occurs at a low frequency.

Once the cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be used to clone a whole animal.

D. COMPOSITIONS

Disclosed are the components to be used to prepare the disclosed compositions as well as the compositions themselves and to be used within the methods disclosed herein. These and other materials are disclosed herein, and it is understood that when combinations, subsets, interactions, groups, etc. of these materials are disclosed that while specific reference to each various individual and collective combinations and permutation of these compounds may not be explicitly disclosed, each is specifically contemplated and described herein. For example, if a particular galanin analog is disclosed and discussed and a number of modifications that can be made to a number of molecules including the variant are discussed, specifically contemplated is each and every combination and permutation of the galanin analog and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Compositions Related to Permeability of the Blood-Brain Barrier

Figure 1:
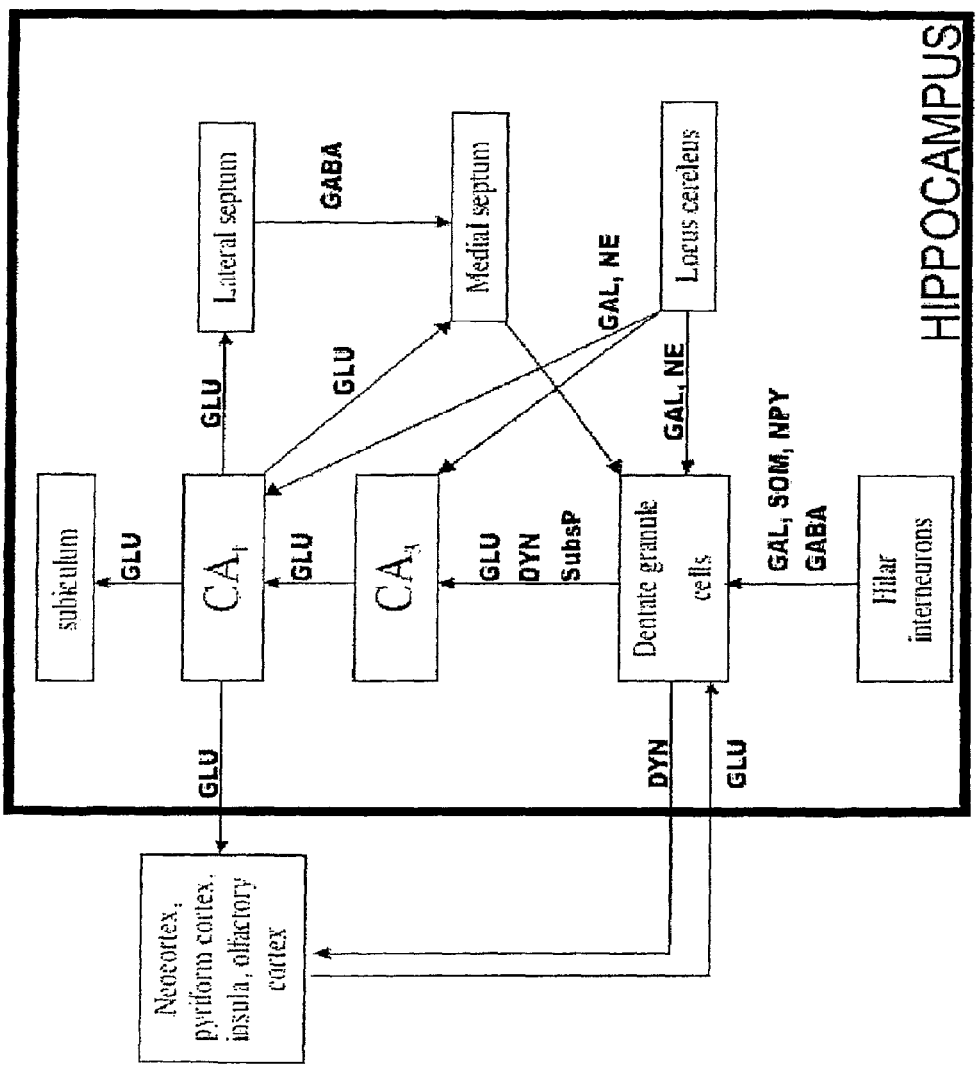

Spontaneous epileptic seizures result from excessive discharge in hyperexcitable neurons primarily located in the hippocampus. The brain controls seizures by balancing inhibitory mechanisms employing γ-aminobutyric acid (GABA) and excitation mechanisms mediated by glutamate (Wasterlain et al., 2002). Neurotransmission is modulated by a number of endogenous neuropeptides, including neuropeptide Y, galanin, nociceptin/orphanin FQ and endomorphin-1. FIG. 1 illustrates possible relationships between glutamate, GABA and neuropeptides in neuronal circuitry of hippocampus in self-sustained status epilepticus.

The role of these neuropeptides has been elucidated using both pharmacological and genetic (knockout or overexpression) approaches. For example, Oberto and coworkers (Oberto et al., 2001) used transgenic mice to characterize the interactions between the GABAergic system, neuropeptide Y and neuropeptide Y(1) receptors in the amygdala (also reviewed in (Eva et al., 2004)). Similarly, Leresche and coworkers (Leresche et al., 2000) showed that somatostatin inhibited GABA-mediated neurotransmission via a presynaptic mechanism. Modulation of glutamate release by galanin in the hippocampus was investigated in two transgenic mouse models: knockout of galanin (GalKO) and overexpressing (GalOE) mice (Mazarati et al., 2000). In GalKO and GalOE mice, depolarization-induced glutamate release was increased and decreased by centrally administered galanin, respectively, indicating a role of hippocampal galanin as an anticonvulsant through the glutamatergic system (Mazarati, 2004).

At least three neuropeptides and their receptors were shown to play a role in epileptogenesis: galanin, somatostatin and neuropeptide Y. Galanin immunoreactivity in the hippocampus is diminished after limbic status epilepticus. Injection of galanin into the hippocampal dentate hilus prevented onset of limbic status epilepticus and stopped status epilepticus. It thus appears that galanin acts as an endogenous anticonvulsant that inhibits status epilepticus (Mazarati et al., 1998). Evidence of this was shown by examining the phenotype of transgenic mice with overexpression of galanin (Kokaia et al., 2001). In this study, galanin suppressed kindling epileptogenesis.

The role of neuropeptides in modulating neurotransmitter release and seizure control has been recognized as an opportunity for new therapeutic treatments. As described below, a number of published studies showed potent anticonvulsant activity of neuropeptides in animal models.

a) Neuropeptide Y and Dynorphin

Neuropeptide Y suppressed epileptiform activity in rat hippocampal slices in vitro (Klapstein and Colmers, 1997). In another study (Baraban et al., 1997), mice lacking neuropeptide Y had uncontrollable seizures in response to kainic acid. Moreover, 93% of knockout mice progressed to death, whereas death was rare in wild-type animals. Intracerebroventricular neuropeptide Y prevented death induced by kainic acid administration. Finally, the anticonvulsant action of neuropeptide Y was demonstrated to be mediated through the Y5 receptors (Sperk and Herzog, 1997).

Figure 5:
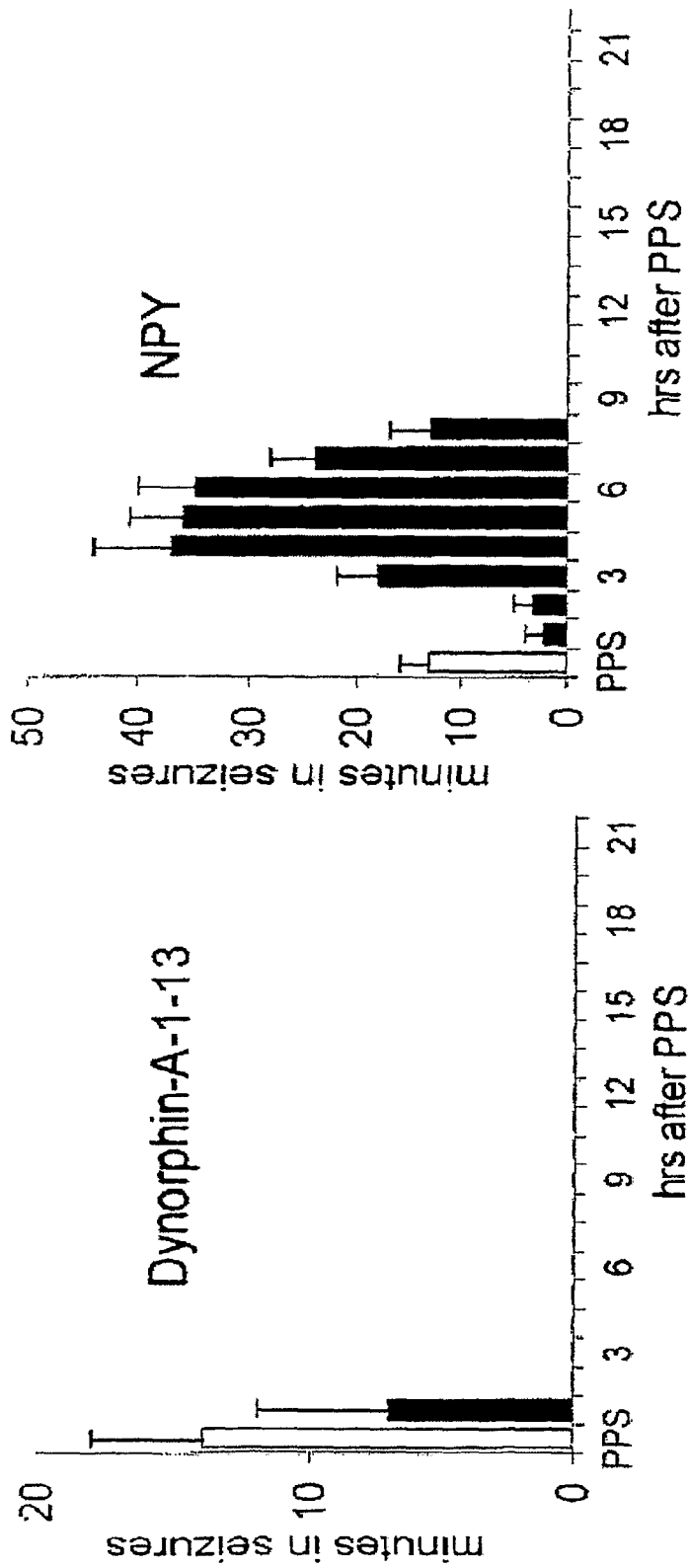
FIG. 5 shows anticonvulsive activity of dynorphin and neuropeptide Y after intrahippocampal injection in the self-sustaining status epilepticus model in rats. Refer to FIG. 4 for the control experiment. (Mazarti and Wasterlain, 2002).

Hippocampal opioid peptides, including dynorphin, have been implicated in epileptogenesis and epileptic seizures (reviewed by (Hong, 1992) and (Solbrig and Koob, 2004)). Seizures induced by either electroconvulsive shocks or amygdala kindling resulted in the initial release of both enkephalin and dynorphin, but also caused a long-term decrease in dynorphin (Gall, 1988). Anticonvulsant activity of dynorphin was shown in the rat model of self-sustained status epilepticus (Mazarati and Wasterlain, 2002), as illustrated in FIG. 5.

As with dynorphin, i.h. injection of neuropeptide Y also reduced distribution of seizures in the self-sustaining status epilepticus model (Mazarati and Wasterlain, 2002). NPY administered into the lateral ventricle appeared to be a potent inhibitor of kainate-induced seizures (Woldbye et al., 1997). It had been suggested that the antiepileptic effect was mediated by neuropeptide Y5 receptors, a finding that was confirmed in a study with Y5R-deficient mice (Marsh et al., 1999).

b) Galanin and Analogs Thereof

Figure 2:
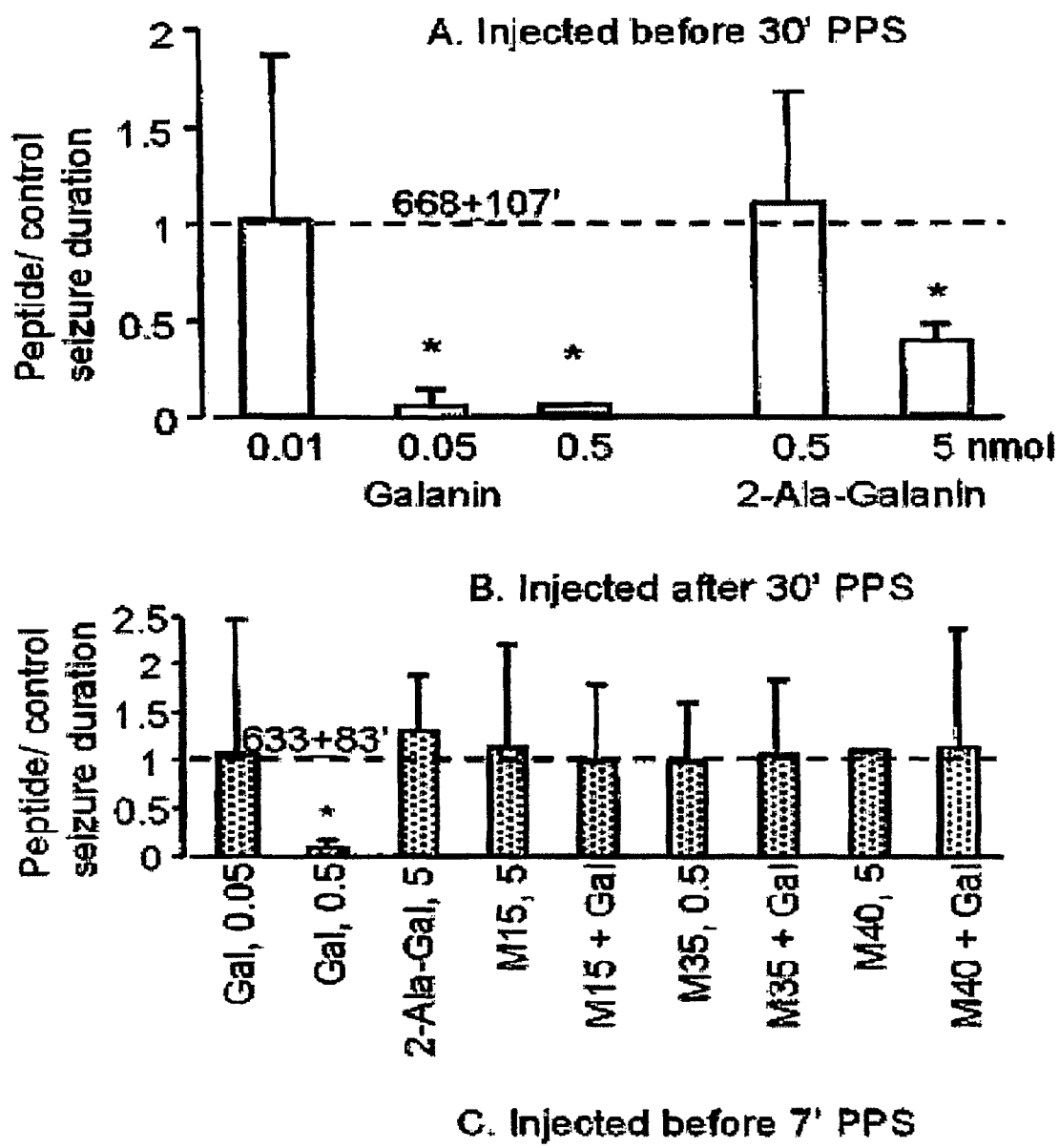

Galanin has been recognized as a potential anticonvulsant agent since the work of Mazarati and coworkers (Mazarati et al., 1992). When injected directly into the lateral brain ventricle or hippocampus, galanin decreased the severity of picrotoxin-induced kindled convulsions in rats. In the animal model of status epilepticus, perihilar injection of galanin, before or after perforant path stimulation (PPS), shortened the duration of seizures (Mazarati et al., 1998). These effects were reversed by co-application of galanin antagonists. As illustrated in FIG. 2, doses as low as 50 to 500 picomoles were effective in stopping established self-sustaining status epilepticus (SSSE).

Figure 3:
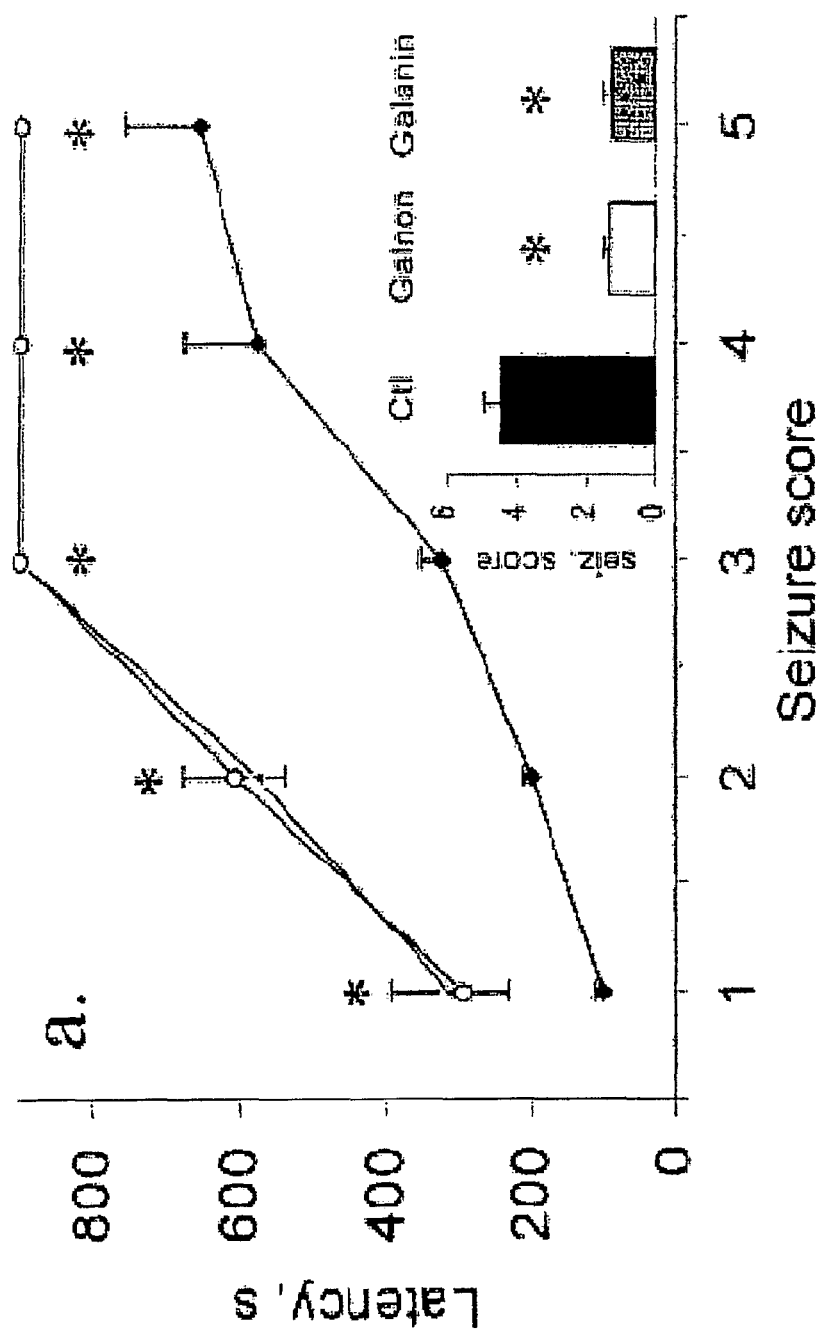
FIG. 3 shows both a nonpeptidic galanin receptor agonist and galanin increased latency and decreased seizure scores on the PTZ-induced seizures in mice. Inset summarizes the maximal seizures score (black, control; open, galnon; grey, galanin). (Saar et al. 2002).

One strategy for treating epilepsy is to use neuropeptide-based therapeutics. As a proof-of-concept, two non-peptide galanin receptor agonists, galnon and galmic, were recently shown to possess anticonvulsant and antiepileptic activities ((Saar et al., 2002) and (Bartfai et al., 2004), respectively). Both compounds appeared to possess a midrange micromolar affinity for GatR1 or GalR2 receptors, and exhibited anticonvulsant activity in animal models of epilepsy when administered systemically. As shown in FIG. 3, galnon (2 mg/kg, i.p.) or galanin (0.5 nmoles, i.c.v.) had comparable effects on both latency and seizure score in the pentylenetetrazo (PTZ)-induced test in mice (Saar et al., 2002; Ceide et al., 2004).

Below is a table showing the affinity of NAX 5055 (GAL-BBB2) toward galanin receptors:

TABLE 2

| Ligand | GalR1 | GalR2 |
|---|---|---|
| Gal(1-16) | 8.5 nM | 8.3 nM |
| NAX 5055 | ~9 nM | ~6 nM |
| Galmic | 34,000 nM | >100,000 nM |
| Galnon | 12,000 nM | 24,000 nM |

When injected i.p., galanin was found to reduce the severity and increased latency for pentylenetertazole-induced seizures in mice. Intrahippocampal injection of galnon was also demonstrated to shorten the duration of self-sustained status epilepticus. Similarly, galmic blocked status epilepticus when injected i.h. or i.p. Thus, these two galanin agonists are useful anticonvulsants, and validate galanin receptors as therapeutic targets for epilepsy.

Galanin is a 30-amino-acid neuropeptide, but SAR studies identified that the N-terminal portion is still a highly potent agonist as compared to the whole-length peptide (Langel and Bartfai, 1998). A galanin(1-16) analog can be used with the methods disclosed herein, in which the Gly$^1$ residue is replaced by N-methyl-Gly (sarcosine, SAR), as shown below:

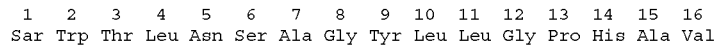

N-methylation of Gly$^1$ protected the peptide from accelerated proteolytic degradation from the N-terminus, whereas it did not significantly change its affinity for the galanin receptor (Rivera Baeza et al., 1994). SAR studies identified the following residues critical for biological activity: Gly$^1$, Trp$^2$, Asn$^5$, Tyr$^9$ and Gly$^{12}$ (Land et al., 1991). The same study identified that the N-terminal extensions caused a loss of the biological activity. On the other hand, the C-terminal portion of galanin(1-16) appears to be very robust when it comes to attaching to larger structures (Pooga et al., 1998). Therefore, the strategy for design of [Sar$^1$]galanin analogs is similar to that used with somatostatin only with regard to amino acid replacements, but it differs by introducing the extensions at the C—, rather than at the N-terminus.

The galanin analog, GAL-BBB2 (SEQ ID NO: 3), exhibited potent anticonvulsant activity (ED50~3 mg/kg) when given i.p. (Example 2). The smallest galanin analog with the most potent and long-lasting anticonvulsant activity can be obtained from GAL-BBB2. Examples of these sequences can be found in SEQ ID NOS: 4-29 (described in detail in Example 2). These peptides can have increased stability when compared to galanin, for example. Also disclosed are galanin analogs GAL-BBB3, GAL-BBB4, GAL-BBB5, GAL-BBB6, GAL-BBB7, and GAL-BBB8 (SEQ ID NOS: 49-54). Each of these can also possess anticonvulsant activity.

Limited structure-function relationship studies are carried out to identify the smallest fragment of the GAL-BBB2 analog that maintains anticonvulsant activity when administered systemically. Galanin analogs containing either the C-terminal and central truncations are synthesized and tested. In addition, limited structure-function relationship study of the C-terminal motif are carried out to optimize permeability of the analog through the blood-brain-barrier. FIG. 14 illustrates the structure of GAL-BBB2 in the context of structure-function studies.

Discussed below are various galanin analogs and methods for their design and synthesis (see examples 1 and 2).

c) Somatostatin

There are many lines of evidence showing that brain somatostatin plays an important role as an inhibitor of seizures and epileptogenesis (Vezzani and Hoyer, 1999). Somatostatin is a major neuropeptide expressed in GABAergic interneurons of the hippocampus. Moreover, somatostatin release from rat hippocampal neurons was stimulated by glutamate (Fontana et al., 1996). The expression of somatostatin and its receptors is significantly changed after epileptic seizures, and this neuropeptide has also been postulated to control neuronal excitability during epileptogenesis (reviewed in (Schwarzer et al., 1996) and (Vezzani and Hoyer, 1999)). Receptor-subtype-knockout and pharmacological studies have suggested the involvement of at least four subtypes of somatostatin receptors (sst1, sst2, sst3 and sst4) in glutamate-mediated neurotransmission in hippocampus (Pikwo et al., 1996). The recent study of Csaba and coworkers (Csaba et al., 2004) provided additional evidence that somatostatin sst2A receptors can play a key role in epileptogenesis and anticonvulsant activity.

Figure 4:
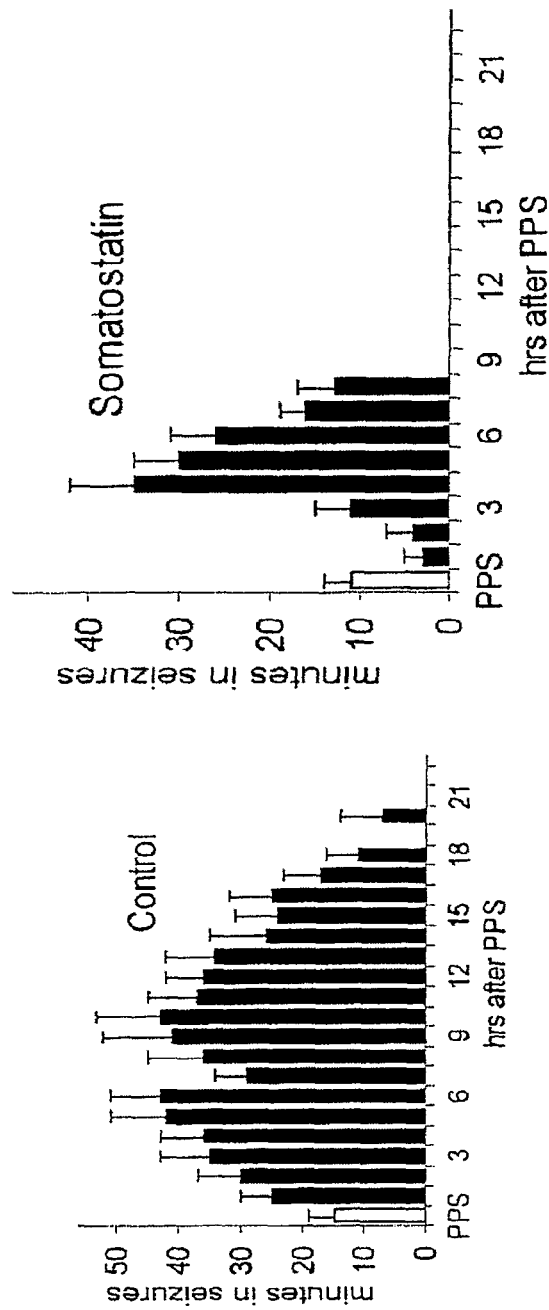
FIG. 4 shows anticonvulsive activity of somatostatin after intrahippocampal injection in the self-sustaining status epilepticus model in rats. (Mazarati and Wasterlain, 2002).

The most direct evidence of the anticonvulant activity of somatostatin comes from studying its pharmacological effects on seizures and epileptogenesis in animal epilepsy models (Vezzani et al., 1991; Perez et al., 1995; Mazarati and Wasterlain, 2002). (Mazarati and Wasterlain, 2002). Injection of somatostatin or its subtype-selective analogs resulted in a reduced number of seizures, and raised the latency to seizures induced by kainic or quinolonic acid (Vezzani et al., 1991). Similarly, infusion of RC-160, the somatostatin sst2-selective agonist decreased the number of animals with pentylenetetrazol-induced tonic-clonic seizures (Perez et al., 1995). As illustrated in FIG. 4, the intrahippocampal injection (i.h.) of somatostatin dramatically decreased the distribution of seizures in a rat model of self-sustained status epilepticus (Mazarati and Wasterlain, 2002).

Somatostatin is a 14-amino-acid hypothalamic peptide with a single disulfide bridge, originally discovered in 1973 (Brazeau et al., 1973). The sequence of somatostatin is shown below:

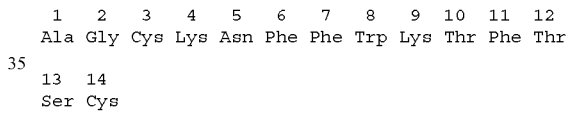

Extensive SAR studies have identified five key residues: Phe$^6$, Phe$^7$, Trp$^8$, Lys$^9$ and Phe$^{11}$, whereas alanine substitutions of Gly$^2$, Lys$^4$, Asn$^5$, Thr$^{10}$, Thr$^{12}$ or Ser$^{13}$ did not significantly affect biological activity (Vale et al., 1975). In addition, the D-Trp$^8$-containing analog was shown to be more potent, due to greater resistance to proteolysis and/or better stabilization of the active conformation.

The [D-Trp$^8$] or [L-Trp$^8$] somatostatin can be used as the metabolically stable analog with the methods disclosed herein. To increase basicity, Thr, Ser or Asn residues can be systematically replaced with isosterically similar, but positively charged DAB (diaminobutyric acid) or DAP (diaminopropionic acid) residues. To increase lipophilicity, a Lys-palmitoyl moiety can be introduced in place of Lys$^4$ or Asn$^5$, and/or Phe residues can be substituted with halogenated equivalent, chloro-Phe residues. As summarized in Table 5, nine analogs are synthesized and assayed for their affinity to somatostatin receptors. The modifications that do not negatively affect high affinity binding are combined together. These 2$^{nd}$-generation analogs comprise 2-4 combined modifications. These sequences can be found in SEQ ID NOS: 31-36.

Next, the N-terminal extensions are introduced to [D-Trp$^8$] or [L-Trp$^8$] somatostatin. These extensions (BBB/PK modulators, as shown in FIG. 8) serve a dual purpose: (1) to improve permeability through the blood-brain barrier by both passive and active mechanisms, and (2) to improve pharmacokinetic properties of neuropeptide drugs by adding a bulky moiety that reduces clearance and improves resistance to proteolytic degradation. Since such "BBB/PK modulators"

are a new concept, several combinations of a few structural modules are used that constitute extensions. Table 6 provides information about the structure and function of the proposed modules.

Also disclosed for use with the compositions and methods disclosed herein is octreotide. For example, SEQ ID NO: 40 discloses an octreotide molecule. FIG. 21 shows the chemical structure and schematic for engineering octreocide. Octreotide is a somatostatin analog that more selective toward sst2 subtype of somatostatin receptors (there are 5 known subtypes). Somatostatin has been shown to be involved in epilepsy and epileptogenesis. The following reference is incorporated in its entirety for its teaching concerning octreotide, somatostatin, and epilepsy: Vezzani A and Hoyer D, Eur Neurosci, 1999, vol 11, pp 3767-3776. Similarly, a role of somatostatin in nociception was shown in Chapman V and Dicjkenson A H, Neuropeptides 1992, vol 23, 147-152, herein incorporated by reference in its entirety for its teaching concerning somatostatin, octreotide, and nociception. A role of somatostatin in a development of Alzheimer disease has recently described (Saito T et al, Nature Medicine, 2005, vol 11, p. 434-439, herein incorporated by reference in its entirety for its teaching concerning octreotide, somatostatin, and Alzheimer disease. Discussed below are methods for designing and synthesizing somatostatin analogs (see Example 1).

d) Delta Sleep inducing Peptide

Delta Sleep Inducing Peptide (DSIP) is an anticonvulsant neuropeptide (Schoenenberger 1984; Kovalzon and Strekalova 2006). DSIP shares some structural similarity with dermorphin, a μ opioid agonist. DSIP was effective in suppressing seizures in the metaphit-induced epilepsy model. Moreover, it has been shown that DSIP potentiated anticonvulsant activity of valproate in the same epilepsy model (Hrncic, Stanojlovic et al. 2006). In addition, this peptide was shown to modulate interactions between enkephalins with opioid receptors, resulting in analgesic effects of DSIP (Nakamura, Nakashima et al. 1986). Neuroprotective activity of DSIP was shown in a model of toxic cerebral oedema. DSIP and some analogs were reported to penetrate the BBB (Kastin, Nissen et al. 1981; Kastin, Banks et al. 1982).

2. Compositions with Increased Permeability of the Blood-Brain Barrier

The compositions disclosed herein have shown increased permeability of the blood-brain barrier. As described herein, disclosed is set of neuropeptide analogs that are designed and synthesized to test their ability to bind with high affinity to their respective receptors. This set includes approximately ten analogs per neuropeptide. High-affinity analogs are further tested for their ability to penetrate the blood-brain barrier. Results from 1 st-generation analogs are followed by the synthesis and evaluation of 2nd- and, subsequently, 3rd-generation analogs. The most promising analogs are selected (high-affinity ligands with enhanced permeability through the blood-brain barrier) to confirm their agonist activity in functional assays. A subset of these analogs (potent agonists with enhanced permeability through the blood-brain barrier) are then pharmacologically tested in vivo.

To become a drug, a neuropeptide analog should possess several important features, including: (1) high potency and selectivity, (2) metabolic stability, (3) relatively long half-life and reduced clearance from systemic circulation, and (4) increased permeability through the blood-brain barrier. Most neuropeptides exhibit high potency and selectivity. Metabolic stability is often introduced by peptide backbone modifications and/or replacements of susceptible residues with residues that are not recognized by proteolytic enzymes. An increase in half-life and decrease in elimination rate can be efficiently achieved by conjugating a polymer-based moiety to a peptide (e.g., PEGylation). Greater permeability through the blood-brain barrier can be introduced by increase in lipophilicity or cationization, as well as by adding prodrug, nutrient transport mimetic or glycosylation. The structure of an ideal drug neuropeptide is schematically shown in FIG. 8.

As illustrated in FIG. 8, a new concept in neuropeptide engineering is the "BBB/PK modulator." The BBB/PK modulator comprises a polymer-based bulky moiety with lipophilic, cationic and transport mimetic modules; this modulator serves a dual purpose, enhancement of the permeability through the blood-brain barrier, and improvement of the pharmacokinetic properties. The cationic and lipophilic modules promote interactions with negatively charged membrane surfaces, and improve the diffusion through the membranes, respectively. The function of the active transport mimetic structure is to increase the specificity of neuropeptide uptake into the brain by enhancing interactions with specific nutrient transporters located on the surface of the brain endothelial cells. The structural framework comprising all of these modules can also improve pharmacokinetic properties of the peptide, mimicking/replacing the role of the commonly used PEG moiety. These bulky moieties are tested as the N- or C-terminal extensions of the model neuropeptides, and more versatile positions of attachment within the neuropeptide structure are also disclosed herein.

The following strategy was used to design neuropeptide analogs with enhanced blood-brain barrier penetrability: begin with metabolically-stable analogs, if available. Identify additional AA positions in the analogs amenable to side chain replacements. Identify positions at the N- and C-termini amenable to introduction of bulky moieties. Increase lipophilicity and basicity of analogs by side-chain replacements. Introduce the extension to a peptide analog that will further increase its lipophilicity and basicity, while improving the pharmacokinetic properties (BBB/PK modulator). Include a nutrient mimetic structure at the extension to improve specificity of the blood-brain barrier penetration. Combine the analogs with side-chain modifications with the extension moiety (BBB/PK modulator).

A key to the successful design of such analogs is the correct combination of the above-mentioned modifications. To achieve this goal, a systematic approach in designing and evaluating individual sets of modifications and their optimal combinations can be taken. The general strategy is schematically illustrated in FIG. 10. The modification of amino acids as disclosed herein can be introduced during solid-phase peptide synthesis using an automated peptide synthesizer. All non-natural amino acids or conjugated structures are as commercially available Fmoc-protected derivatives.

It is understood that when variants are referred to, the variants designate specific properties dependent on the specific substitutions denoted, however, other substitutions, deletions, and/or insertions, for example, conservative substitutions, insertions, and/or deletions at positions other than the specifically denoted positions are also contemplated provided the variants retain the disclosed activities.

Disclosed are analogs of galanin that have desirable properties, such as increased permeability of the blood brain barrier. Also disclosed are analogs of somatostatin that have increased permeability of the blood-brain barrier. As defined above, by "increasing" or "increased" is meant a higher percentage of the composition is able to cross the blood-brain barrier compared with the wild type, non-altered, or native peptide, or with a control composition. For example, the rate of increase can be 1, 2, 3, 4, 5, 6, 7, 8, 9, 10, 11, 12, 13, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 percent when compared with the control, native, or wild type peptide or composition.

It is also understood that each individual analog discussed in the tables in the Examples also has a base permeability which can be determined from the disclosed activities of the composition. It is understood that these percentages of increased activity can be calculated from a base permeability of a wild type, native, or control peptide obtained at any time which provides data in the analytical range of the assay, unless otherwise indicated.

Disclosed are substitutions, deletions, modifications, additions, and extensions to the known, or wild type, peptide, as disclosed in Examples 1 and 2. For example, in Table 7, disclosed are N-terminal extensions for somatostatin. The extensions disclosed herein can be used with a native, wild type, or known peptide, or can be used in combination with an analog of a known peptide. For example, side chain modifications can be made to the known peptide, and then combined with an extension as disclosed herein.

Also disclosed are amino acid substitutions and additions, wherein the substitution or addition is of a non-naturally occurring substance. Examples include, but are not limited to, sarcosine, diaminobutyric acid (DAB), diaminopropionic acid (DAP), Lys-palmityoyl, Chloro-phe, aminohexanoic acid (AHX), perfluorohexanoic acid (PerFHX), 8-amino-3,6,-dioxaoctanic acid, and oligo-Lys, tert-leucine, Further disclosed are replacements of amino acid residues with a "backbone prothesesis", such as a non-peptidic spacer. Examples include, but are not limited to, aminovaleric or aminohexanoic acid. This can result in a minimization of the overall molecular size without significant change of spacing between key residues. The spacer can replace 1, 2, 3, 4, 5, 6, 7, 8, 9, 10, 11, 12, 13, 14, 15, 16, 17, 18, 19, 20, 25, 30, 40, or 50 residues, for example.

Also disclosed herein are variations of amino acids wherein their conformation has been changed. For example, disclosed herein are D-Lys, D-Trp, and L-Trp.

Disclosed are analogs of known compounds, such as galanin and somatostatin, having at least 40%, 45%, 50%, 55%, 60%, 65%, 70%, 75%, 80%, 85%, 90%, or 95% identity (for example) to the parent sequence (such as galanin or somatostatin) and wherein the analog comprises at least one, at least two, at least three, at least 4, at least 5, or at least 6 of any of the substitutions, deletions, additions, or extensions disclosed herein.

3. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 40, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation method. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

4. Nucleic Acids

There are a variety of molecules disclosed herein peptides, such as various galanin and somatostatin analogs. It is understood that these peptide based molecules can be encoded by a number of nucleic acids, including for example the nucleic acids that encode, for example, SEQ ID NOS 1-55, and it is understood that for example, when a vector is expressed in a cell, that the expressed mRNA will typically be made up of A, C, G, and U.

a) Sequences

There are a variety of sequences related to, for example, galanin, which can be found at, for example, Genbank database which can be accessed at www.pubmed.gov. These sequences and others are herein incorporated by reference in their entireties as well as for individual subsequences contained therein.

One particular sequence set forth in SEQ ID NO: 3 is used herein as, an example, to exemplify the disclosed compositions and methods. It is understood that the description related to this sequence is applicable to any sequence related to a galanin analog unless specifically indicated otherwise. Those of skill in the art understand how to resolve sequence discrepancies and differences and to adjust the compositions and methods relating to a particular sequence to other related sequences (i.e. sequences of galanin analogs). Primers and/or probes can be designed for any galanin-related nucleic acid sequence, for example, given the information disclosed herein and known in the art.

5. Delivery of the Compositions to Cells (Vectors)

There are a number of compositions and methods which can be used to deliver nucleic acids or peptides to cells, either in vitro or in vivo. The vectors disclosed herein can be used in multiple ways. In one example, the vectors disclosed herein can be used to deliver nucleic acids encoding the peptides disclosed herein to cells and subjects. Vectors can also be used with peptides to facilitate the crossing of the blood-brain barrier, as discussed above.

Methods and compositions relating to vectors can largely be broken down into two classes: viral based delivery systems and non-viral based delivery systems. For example, nucleic acids and peptides can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier. For the purpose of further improvement of delivering the compositions across blood-brain barrier, the TAT protein transduction domain can be used (Dietz G P and Bahr M, Mol Cell Neurosci, 2004, vol 27, p. 85-131).

As used herein, plasmid or viral vectors are agents that transport the disclosed nucleic acids or peptides, such as those related to galanin and somatostatin analogs, into the cell without degradation. In some embodiments the delivery systems are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions, such as nucleic acids encoding galanin analogs, can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed variants or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of marine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

6. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell. Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell. Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

7. Peptides a) Protein Variants

As discussed herein there are numerous variants of a peptide that are known and herein contemplated. In addition, to the disclosed functional variants and analogs related to the positions disclosed herein, there are known functional naturally occurring variants at positions other than those disclosed herein, which also function as desired. Protein variants and derivatives are well understood to those of skill in the art and can involve amino acid sequence modifications or functional fragments. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 3 and 4 and are referred to as conservative substitutions.

TABLE 3

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 4

Amino Acid Substitutions
Original Residue Exemplary Conservative Substitutions,
others are known in the art.

| | |
|---|---|
| Ala | ser |
| Arg | lys, gln, his |
| Asn | gln; his |
| Asp | glu |
| Cys | ser |
| Gln | asn, lys |
| Glu | asp |
| Gly | Ala |
| His | asn; gln |
| Ile | leu; val |
| Leu | ile; val |
| Lys | arg; gln; his |
| Met | Leu; ile |
| Phe | met; leu; tyr |
| Ser | thr, asn |
| Thr | ser, gln |
| Trp | tyr |
| Tyr | trp; phe |
| Val | ile; leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert or disable sites for N-glycosylation (Asn-X-Thr/Ser) or O-glycosylation (Ser or Thr). Deletions or substitutions of cysteine or methionine (for example in "neutrophil-resistant" proteins due to generation of oxidants by neutrophils) or other labile residues also may be desirable Deletions or substitutions of potential proteolysis sites, e.g. Arg, may be accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of amines in the epsilon-amino group of lysine, arginine, and histidine side chains (T. E. Creighton, Proteins: Structure and Molecular Properties, W.H. Freeman & Co., San Francisco pp 79-86 [1983], acetylation of the N-terminal amine and, in some instances, amidation of the C-terminal carboxyl.

Disulfide bonds are covalent interactions between the thiol group of two cysteine molecules. Through an oxidative reaction, the hydrogen atoms are removed from the thiol groups allowing the formation of a disulfide bridge; the resulting bonded cysteines are termed cystine. Disulfide bonds fall into to categories class I and class U. It is a class II bond which serves to stabilize the three dimensional structure of a protein by linking cysteines within a chain. A class I disulfide bond results when these interactions occur between separate chains. The formation of class I disulfide bonds can aid in the formation of dimeric proteins, an important feature which is often necessary for receptors to provide proper receptor-ligand interactions. Amino acid substitutions may be made at sites where cysteine residues occur; typically, conservative substitutions do not alter cysteine residues involved in disulfide bonds. Such substitutions may have the effect of changing protein folding or altering multimer interactions if the substituted residue is involved in disulfide bonds. It can be determined which cysteines are involved in disulfide bonds.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

Also disclosed are fragments of the disclosed proteins and variants. Typically these fragments will retain at least one of the functions described herein, such as increased permeability of the blood-brain barrier. However, it is understood that fragments that do not retain this activity, for example, can still be used to, for example, generate antibodies. It is also understood that that there are a variety of different functional activities held by galanin, for example. These activities can be related but are not necessarily required. Those of skill understand how to manipulate functional domains of the disclosed analogs by, for example, altering a region contributing to a particular function. Analogs having specific functional sites removed or altered are disclosed in Examples 1 and 2.

8. Antibodies

Antibodies as disclosed herein can be useful in identifying analogs with a desired function. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an exhibit various effector functions, such as participation of the antibody in antibody in antibody dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided For example, fragments of antibodies which maintain increased permeability are included within the meaning of the term "antibody or fragment thereof." Such antibodies and fragments can be made by techniques known in the art and can be screened for specificity and activity according to the methods set forth in the general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

9. Pharmaceutical Carriers/Delivery of Pharmaceutical Products

As described above, the compositions, such as galanin analogs, can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, and topical intranasal administration or administration by inhalant can be used. The exact amount of the compositions required will vary from subject to subject, depending on the species, age, weight and general condition of the subject the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including galanin analogs, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compositions, such as galanin analogs, can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptom's of the disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

10. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

Also disclosed are chips where at least one address is the sequences or part of the sequences set forth in any of the nucleic acid sequences disclosed herein wherein the sequence includes at least one of the variant sequences disclosed herein. Also disclosed are chips where at least one address is the sequences or portion of sequences set forth in any of the peptide sequences disclosed herein, wherein the peptide sequence comprises at least one of the galanin analog disclosed herein.

Also disclosed are chips where at least one address is the sequences or part of the sequences set forth in any of the nucleic acid sequences disclosed herein wherein the sequence includes at least one of the variant sequences within the region defined herein. Also disclosed are chips where at least one address is the sequences or portion of sequences set forth in any of the peptide sequences disclosed herein, wherein the peptide sequence comprises at least one of the substitutions, additions, mutations, or deletions disclosed herein.

11. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums are. Thus, computer readable mediums on which the nucleic acids or protein sequences are recorded, stored, or saved are disclosed.

Disclosed are computer readable mediums comprising the sequences and information regarding the sequences set forth herein.

12. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include amino acids to perform the substitutions discussed in certain embodiments of the methods, as well as instructions.

13. Compositions with Similar Functions

It is understood that the compositions disclosed herein have certain functions, such as increased permeability of the blood-brain barrier. Disclosed herein are certain structural requirements for performing the disclosed functions, and it is understood that there are a variety of structures which can perform the same function which are related to the disclosed structures, and that these structures will ultimately achieve the same result.

E. METHODS OF MAKING THE COMPOSITIONS

The compositions disclosed herein and the compositions necessary to perform the disclosed methods can be made using any method known to those of skill in the art for that particular reagent or compound unless otherwise specifically noted. It is understood that general molecular biology techniques, such as those disclosed in Sambrook et al., *Molecular Cloning: A Laboratory Manual,* 2nd Edition (Cold Spring Harbor Laboratory Press, Cold Spring Harbor, N.Y., 1989) are available for making the disclosed molecules and practicing the disclosed methods unless otherwise noted.

Specifically disclosed herein is a method of making a composition with increased permeability of the blood brain barrier, comprising making a composition with increased permeability of the blood-brain bather, wherein the composition comprises a peptide with increased lipophilic character and increased basicity when compared to the non-altered form of the peptide. In one example, the lipophilic character can be increased by conjugating the peptide to a hydrophobic moiety, such as polyaliphatic chains. The lipophilic character can also be increased by increasing halogenation of aromatic residues. The basicity can be increased by introducing homo- and heterooligomers of positively charged amino acid residues, including, but not limited to Lysine, Arginine, homo-Lysine, homo-Arginine, Ornitine in L- or D-isomer configuration; 2,3-Diaminopropioic acid; 2,4-Diaminobutyric acid. In another example, the basicity can be increased by conjugation to polyamine-based moieties, such as spermine, spermidine, polyamidoamine dendrimers or polyamine toxins and derivatives thereof. The peptide can cross the blood-brain barrier with 1%, 5%, 10%, 20%, 30%, 40%, 50%, 60%, 70%, 80%, 90%, or 100% more efficiency compared to the non-altered peptide. The peptide can also have increased glycosylation when compared to the non-altered form of the peptide. The peptide can comprise a spacer. The spacer can be selected from the group consisting of: Gly, Ahx, Gly-Ahx, or PEG-O2Oc.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods; for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). (Peptide nucleic acid molecules) can be made using known methods such as those described by Nielsen et al., Bioconjug. Chem. 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxy-carbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen. L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis T et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process for Making the Compositions

Disclosed are processes for making the compositions as well as making the intermediates leading to the compositions. For example, disclosed are proteins in SEQ ID NOs: 1-55. There are a variety of methods that can be used for making these compositions, such as synthetic chemical methods and standard molecular biology methods. It is understood that the methods of making these and the other disclosed compositions are specifically disclosed.

Disclosed are proteins produced by the process comprising linking in an operative way a nucleic acid encoding a galanin analog comprising the sequence set forth in SEQ ID NO: 3 and a sequence controlling the expression of the nucleic acid.

Also disclosed are proteins produced by the process comprising linking in an operative way a nucleic acid molecule encoding a galanin analog comprising a sequence having 80% identity to a sequence set forth in SEQ ID NO: 3, and a sequence controlling the expression of the nucleic acid.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

It is understood that another way of producing the proteins would be to use rabbit expression systems, such as those types of systems produced by Biprotein Technologies. The disclosed molecules can be produced using these types of vectors and production systems. For example, these types of systems are disclosed EPO Patent Application No. 92 401 635.5, U.S. Pat. No. 5,965,788) and on a gene insulator (EPO Patent Application No. 00 403 658.8).

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Systemically-Active Anticonvulsant Galanin Analog

To obtain proof-of-concept results that anticonvulsant neuropeptides can be engineered to enhance their penetration across the blood-brain barrier, two model neuropeptides were selected: somatostatin and galanin. As described previously, both of these neuropeptides possess anticonvulsant activity.

The general experimental strategy is illustrated in FIG. 7. A set of neuropeptide analogs (the 1st generation) are designed and synthesized to test their ability to bind with high affinity to their respective receptors. This set includes approximately ten analogs per neuropeptide. High-affinity analogs are further tested for their ability to penetrate the blood-brain barrier. Results from 1st-generation analogs are followed by the synthesis and evaluation of 2nd- and, subsequently, 3rd-generation analogs. The most promising analogs are selected (high-affinity ligands with enhanced permeability through the blood-brain barrier) to confirm their agonist activity in functional assays. A subset of these analogs (potent agonists with enhanced permeability through the blood-brain barrier) are then pharmacologically tested in vivo.

To become a drug, a neuropeptide analog should possess several important features, including: (1) high potency and selectivity, (2) metabolic stability, (3) relatively long half-life and reduced clearance from systemic circulation, and (4) increased permeability through the blood-brain barrier Most neuropeptides exhibit high potency and selectivity. Metabolic stability is often introduced by peptide backbone modifications and/or replacements of susceptible residues with residues that are not recognized by proteolytic enzymes. An increase in half-life and decrease in elimination rate can be efficiently achieved by conjugating a polymer-based moiety to a peptide (e.g., PEGylation). Greater permeability through the blood-brain barrier can be introduced by increase in lipophilicity or cationization, as well as by adding prodrug, nutrient transport mimetic or glycosylation. The structure of an ideal drug neuropeptide is schematically shown in FIG. 8.

As illustrated in FIG. 8, a new concept in neuropeptide engineering is introduced: the "BBB/PK modulator." The BBB/PK modulator comprises a polymer-based bulky moiety with lipophilic, cationic and transport mimetic modules; this modulator serves a dual purpose, enhancement of the permeability through the blood-brain barrier, and improvement of the pharmacokinetic properties. The cationic and lipophilic modules promote interactions with negatively charged membrane surfaces, and improve the diffusion through the membranes, respectively. The function of the active transport mimetic structure is to increase the specificity of neuropeptide uptake into the brain by enhancing interactions with specific nutrient transporters located on the surface of the brain endothelial cells. The structural framework comprising all of these modules can also improve pharmacokinetic properties of the peptide, mimicking/replacing the role of the commonly used PEG moiety. These bulky moieties are tested as the N- or C-terminal extensions of the model neuropeptides, and more versatile positions of attachment within the neuropeptide structure are also disclosed herein.

The following strategy was used to design neuropeptide analogs with enhanced blood-brain barrier penetrability: begin with metabolically-stable analogs, if available. Identify additional AA positions in the analogs amenable to side chain replacements. Identify positions at the N- and C-termini amenable to introduction of bulky moieties. Increase lipophilicity and basicity of analogs by side-chain replacements. Introduce the extension to a peptide analog that will further increase its lipophilicity and basicity, while improving the pharmacokinetic properties (BBB/PK modulator). Include a nutrient mimetic structure at the extension to improve specificity of the blood-brain barrier penetration. Combine the analogs with side-chain modifications with the extension moiety (BBB/PK modulator).

A key to the successful design of such analogs is the correct combination of the above-mentioned modifications. To achieve this goal, a systematic approach in designing and evaluating individual sets of modifications and their optimal combinations can be taken. The general strategy is schematically illustrated in FIG. 10. The modification of amino acids as disclosed herein can be introduced during solid-phase peptide synthesis using an automated peptide synthesizer. All non-natural amino acids or conjugated structures are as commercially available Fmoc-protected derivatives.

Somatostatin is a 14-amino-acid hypothalamic peptide with a single disulfide bridge, originally discovered in 1973 (Brazeau et al., 1973). The sequence of somatostatin is shown below:

| 1 | 2 | 3 | 4 | 5 | 6 | 7 | 8 | 9 | 10 | 11 | 12 |
|---|---|---|---|---|---|---|---|---|----|----|----|
| Ala | Gly | Cys | Lys | Asn | Phe | Phe | Trp | Lys | Thr | Phe | Thr |

| 13 | 14 |
|----|----|
| Ser | Cys |

Extensive SAR studies have identified five key residues: Phe[6], Phe[7], Trp[8], Lys[9] and Phe[11], whereas alanine substitutions of Gly[2], Lys[4], Asn[5], Thr[10], Thr[12] or Ser[13] did not significantly affect biological activity (Vale et al., 1975). In addition, the D-Trp[8]-containing analog was shown to be more potent, due to greater resistance to proteolysis and/or better stabilization of the active conformation.

The [D-Trp[8]] somatostatin can be used as the metabolically stable analog with the methods disclosed herein. To increase basicity, Thr, Ser or Asn residues can be systematically replaced with isosterically similar, but positively charged DAB (diaminobutyric acid) or DAP (diaminopropionic acid) residues. To increase lipophilicity, a Lys-palmitoyl moiety can be introduced in place of Lys[4] or Asn[5], and/or Phe residues can be substituted with halogenated equivalent, chloro-Phe residues. As summarized in Table 5, nine analogs are synthesized and assayed for their affinity to somatostatin receptors. The modifications that do not negatively affect high affinity binding are combined together. These $2^{nd}$-generation analogs comprise 2-4 combined modifications.

Next, the N-terminal extensions are introduced to [D-Trp[g]] somatostatin. These extensions (BBB/PK modulators, as shown in FIG. 8) serve a dual purpose: (1) to improve permeability through the blood-brain barrier by both passive and active mechanisms, and (2) to improve pharmacokinetic properties of neuropeptide drugs by adding a bulky moiety that reduces clearance and improves resistance to proteolytic degradation. Since such "BBB/PK modulators" are a new concept, several combinations of a few structural modules are used that constitute extensions. Table 6 provides information about the structure and function of the proposed modules.

TABLE 5

Summary of side chain replacements in somatostatin proposed in this study.

| 1 | 2 | 3 | 4 | 5 | 6 | 7 | 8 | 9 | 10 | 11 | 12 | 13 | 14 |
|---|---|---|---|---|---|---|---|---|---|---|---|---|---|
| Ala | Gly | Cys | Lys | Asn | Phe | Phe | D-Trp | Lys | Thr | Phe | Thr | Ser | Cys |
| Ala | Ala | | DAB | | | | | | DAP | | DAP | DAP | |
| | | | Lys-palm | Lys-palm | | | | | | | | | |
| | | | | | Cl-Phe | Cl-Phe | | | | Cl-Phe | | | |

DAB, diaminobutyric acid; DAP, diaminopropionic acid; Lys-palm, Lys-palmitoyl; Cl-Phe, chloro-Phe.

TABLE 6

Summary of structural and functional properties of modules used to synthesize BBB/PK modulator.

| Module | Structure | Function/Comments |
|---|---|---|
| AHX | Aminohexanoic acid | Increase lipophilicity in the middle of the extension to improve passive penetration through membranes. No additional hydrogen bond donors/acceptors are introduced. |
| PerFHX | Perfluorohexanoic acid | Increase lipophilicity by capping N-terminus with extremely hydrophobic "tail". This is a very efficient strategy to increase hydrophobicity without significant increase in the molecular size of the extension. |
| PEG-spacer | 8-amino-3,6-dioxaoctanic acid | Increase length/size of the extension using a PEG-based spacer: this should result in improved pharmacokinetic properties of the analogs. |
| Phe | Phe-[D-Phe] | Mimetic of Phe as substrate recognition for active transport of nutrients; alternatively, a glycosyl moiety may also be introduced. |
| Oligo-(Lys) | Lys-(D-Lys)-Lys-(D-Lys)-Lys-(D-Lys)-Lys | Increase of basicity of the extension: this should enhance electrostatic interactions with the membranes. |

The modules can be introduced during solid-phase synthesis as extensions to the Ala$^1$ residue of [D-Trp$^8$]somatostatin. Table 7 and FIG. 11 summarize the extensions.

TABLE 7

Summary of N-terminal extensions in somatostatin analogs (for abbreviations used, refer to Table 6).

| Analog # | Module 3 | Module 2 | Module 1 | Analog |
|---|---|---|---|---|
| EXT1 | | | AHX-AHX | [D-Trp$^8$]SOM |
| EXT2 | | | PerFHX | [D-Trp$^8$]SOM |
| EXT3 | | | PEG-spacer | [D-Trp$^8$]SOM |
| EXT4 | | AHX-AHX | PEG-spacer | [D-Trp$^8$]SOM |
| EXT5 | | PerFHX | PEG-spacer | [D-Trp$^8$]SOM |
| EXT6 | | Oligo-(Lys) | PEG-spacer | [D-Trp$^8$]SOM |
| EXT7 | | Phe | AHX-AHX | [D-Trp$^8$]SOM |
| EXT8 | | Phe | AHX | [D-Trp$^8$]SOM |
| EXT9 | AHX-AHX | Oligo-(Lys) | PEG-spacer | [D-Trp$^8$]SOM |
| EXT10 | Phe | Oligo-(Lys) | PEG-spacer | [D-Trp$^8$]SOM |

Initially, ten analogs are synthesized and evaluated for their binding properties to the somatostatin receptors. High-affinity analogs are further evaluated for their permeability properties through the model blood-brain barrier permeability assay.

Once the optimal extensions are selected, they can be attached to somatostatin analogs already containing optimized side-chain replacements (see Table 5). Since it is difficult to predict the best combination of "extension analogs" with "side-chain replacement analogs", a matrix approach is utilized, wherein each selected analog is synthesized with each selected extension. 9-12 analogs can be achieved in this round. Such $3^{rd}$-generation analogs can be tested in all three in vitro assays: (1) binding to the somatostatin receptors, (2) agonist activity, and (3) permeability through the model blood-brain barrier. A limited number of the most promising analogs can be selected for pharmacological testing in the in vivo mouse epilepsy models.

TABLE 8

Matrix-approach in designing somatostatin analogs with the attached N-terminal BBB/PK modulators. Here, three selected extension structures are combined with three selected "side-chain replacement" analogs.

| | EXT-A | EXT-B | EXT-C |
|---|---|---|---|
| Analog 1 | ✓ | ✓ | ✓ |
| Analog 2 | ✓ | ✓ | ✓ |
| Analog 3 | ✓ | ✓ | ✓ |

An approach similar to that described above for somatostatin can be undertaken with galanin and its analogs. Galanin is a 30-amino-acid neuropeptide, but SAR studies identified that the N-terminal portion is still a highly potent agonist as compared to the whole-length peptide (Langel and Bartfai, 1998). A galanin(1-16) analog can be used with the methods disclosed herein, in which the Gly$^1$ residue is replaced by N-methyl-Gly (sarcosine, SAR), as shown below:

| 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|
| Sar | Trp | Thr | Leu | Asn | Ser | Ala | Gly | Tyr | Leu | Leu | Gly | Pro | His | Ala | Val |

N-methylation of Gly$^1$ protected the peptide from accelerated proteolytic degradation from the N-terminus, whereas it did not significantly change its affinity for the galanin receptor (Rivera Baeza et al., 1994). SAR studies identified the following residues critical for biological activity: Gly$^1$, Trp$^2$, Asn$^5$, Tyr$^9$ and Gly$^{12}$ (Land et al., 1991). The same study identified that the N-terminal extensions caused a loss of the biological activity. On the other hand, the C-terminal portion of galanin(1-16) appears to be very robust when it comes to attaching to larger structures (Pooga et al., 1998). Therefore, the strategy for design of [Sar$^1$]galanin analogs is similar to that used with somatostatin only with regard to amino acid replacements, but it differs by introducing the extensions at the C-, rather than at the N-terminus. Table 9 summarizes galanin analogs with amino acid replacements.

TABLE 9

Replacements of individual residues in [Sar1]galanin(1-16).
For amino acid coding, refer to Table 5.

| 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|
| Sar | Trp | Thr | Leu | Asn | Ser | Ala | Gly | Tyr | Leu | Leu | Gly | Pro | His | Ala | Val |
| | | DAP | | DAP | DAP | | | | | | | DAB | | DAP | DAB |
| | | | | | | | | | | | | Lys-palm | Lys-palm | Lys-palm | |
| | | | | | | | | Cl-Tyr | | | | | | | |

The C-terminal extensions can be identical to those shown in Table 7, but introduced at position His$^{14}$. (Sar$^1$)galanin with the Lys$^{14}$(Mmt) residue (side chain protected with a 4-methoxytrityl group) is then synthesized. After coupling sarcosine, the peptide resin can be treated with 1% TFA in dichloromethane for 30 minutes. The side-chain amino group of the Lys$^{14}$ residue can be deprotected, followed by coupling of the extension modules. The design of the 3$^{rd}$-generation analogs with combined side chain replacements and the C-terminal extensions are identical to that described for the somatostatin analogs.

Chemical Synthesis of Neuropeptides.

The peptides are synthesized using Fmoc-based solid-phase peptide synthesis protocols and an automated peptide synthesizer. Coupling methods and removal of the peptides from solid support are performed as described by Chan and White (Chan and White, 2000). The peptides can be removed from solid support by treatment with reagent K. Following wash and precipitation, the analogs are purified using preparative reversed-phase HPLC separations. The disulfide bridge in the somatostatin analogs can be formed by incubating purified peptide with 2% DMSO, 30% acetic acid in water, pH 7.0, as described (Chen et al., 2000). At least several milligrams of each peptide analog can be produced by this method.

To evaluate permeability of neuropeptide analogs though the blood-brain barrier, pION's PAMPA method can be employed. In this method, a filter with an immobilized artificial membrane is placed between two compartments: a donor and an acceptor. The analogs can be placed in the donor compartment. After the appropriate time interval, the donor and acceptor compartments are quantified using UV spectroscopy.

Somatostatin and galanin binding assays (non-selective) are performed by Novascreen Biosciences Corporation. Rat forebrain membranes and radiolabeled parent neuropeptides are used in these assays. The analogs are tested at a single (1 µM) concentration to distinguish between high- and low-affinity analogs. The agonist activity of selected somatostatin and galanin analogs can be further tested using functional assays provided by MDS-Pharma Services. The analogs can be tested at a single concentration (1

Anticonvulsant Testing.

Anticonvulsant activity can be established in the Frings AGS-susceptible mouse model of reflex epilepsy. The AGS-susceptible mouse is the ideal acute seizure model for initial proof-of-concept studies because it is non-discriminatory, and effectively detects a wide variety of CNS active compounds (White et al., 1992). Peptides found to be active in the Frings mouse can be evaluated for their ability to block seizures induced by maximal electroshock (MES) and subcutaneously (s.c.) administered pentylenetetrazol (PTZ). These two tests measure the ability of an investigational antiepileptic compound to prevent seizure spread and elevate seizure threshold, respectively (White et al., 2002). Once a modified peptide has been demonstrated to be active in one or more of these three seizure tests, complete dose-response studies are conducted at the previously determined time of peak effect following i.v. administration. Results from these proof-of-concept studies are then compared to efficacy studies conducted following intracerebroventricular (i.c.v.) administration. A leftward shift in the i.p. dose-response curve can be observed as greater penetration of the blood-brain barrier is achieved. Collectively, the results obtained from these three seizure tests provide substantial data supporting the approach to make small peptides more accessible to the brain following systemic administration. The details of each individual seizure test are outlined below.

Administration of Neuropeptide Analogs.

Each of the modified neuroactive peptides are administered intracerebroventricularly (i.c.v.) in 5 µl artificial cerebrospinal fluid via a 10 µl Hamilton syringe or intraveneously (i.v.) in 0.5% methylcellulose in a volume of 0.01 ml/g body weight.

Audiogenic Seizures.

The ability of individual modified peptides to prevent seizures induced by sound in the AGS-susceptible Frings mouse model can be assessed at the time of peak effect (White et al., 1992). For this test, individual mice are placed into a plexiglass cylinder (diameter, 15 cm; height, 18 cm) fitted with an audio transducer (Model AS-ZC; FET Research and Development, Salt Lake City, Utah), and exposed to a sound stimulus of 110 decibels (11 KHz) delivered for 20 seconds. Sound-induced seizures are characterized by wild running followed by loss of righting reflex with forelimb and hindlimb tonic extension. Mice not displaying hindlimb tonic extension are considered protected.

MES Test.

For the MES test, a drop of anesthetic/electrolyte solution (0.5% tetracaine hydrochloride in 0.9% saline) can be applied to the eyes of each animal prior to placement of the corneal electrodes. The electrical stimulus in the mouse MES test is 50 mA delivered for 0.2 sec by an apparatus similar to that originally described by Woodbury and Davenport (Woodbury and Davenport, 1952). Abolition of the hindleg tonic extensor component of the seizure is used as the endpoint.

Minimal Toxicity Tests.

Minimal toxicity can be identified in mice by the rotarod procedure (Dunham and Miya, 1957). When a mouse is placed on a 1-inch knurled rod that rotates at a speed of 6 r.p.m., the animal can maintain its equilibrium for long periods of time. The animal can be considered toxic if it falls off this rotating rod three times during a 1-minute period.

Determination of Median Effective (ED$_{50}$) or Toxic Dose (TD$_{50}$).

All quantitative in vivo anticonvulsant/toxicity studies are conducted at the previously determined TPE. Groups of at least eight mice are tested with various doses of the peptide until at least two points have been established between the limits of 100% protection or minimal toxicity, and 0% protection or minimal toxicity. The dose of drug required to produce the desired endpoint in 50% of animals (ED$_{50}$ or TD$_{50}$) in each test, the 95% confidence interval, the slope of the regression line, and the S.E.M. of the slope is then calculated by a computer program based on the method described by Finney (Finney, 1971).

Analogs of somatostatin can be found in Table 10 (all analogs have a disulfide bridge formed between two cysteine residues):

TABLE 10

SOM-BBB1  (NN3APG)(AHX)AGCKNFFWKTFTSC (SEQ ID NO: 41)

SOM-BBB2  (NN3APG)(AHX)AGCKNFF($_D$W)KT(Cl-Phe)T(Dap)C (SEQ ID NO: 42)

SOM-BBB3  W(AHX)KKCKNFF($_D$W)KT(Cl-Phe)(Dab)(Dab)C (SEQ ID NO: 43)

TABLE 10-continued

```
SOM-BBB21  KK(Lys-P)K(AHX)(DF)CF(DW)KTC-Thr(ol) (SEQ ID NO: 44)

SOM-BBB22  KKK(Lys-P)K(AHX)(AHX)(DF)CF(DW)KTC-Thr(ol) (SEQ ID NO: 45)

SOM-BBB23  (Lys-P)KK(Lys-P)K(AHX)(DF)CF(DW)KTC-Thr(ol) (SEQ ID NO: 46)

SOM-BBB24  KK(Lys-P)K(AHX)KK(Lys-P)K(AHX)(DF)CF(DW)KTC-Thr(ol)
           (SEQ ID NO: 47)

SOM-BBB25  (PFHA)K(DK)K(ACPA)KK(Lys-P)K(AHX)(DF)CF(DW)KTC-Thr(ol)
           (SEQ ID NO: 48)
```

In the above table, (AHX) is aminohexanoic acid, (Dab) is diaminobutyric acid, (Dap) is diaminopropionic acid, (Tle) is tert-Leucine, (Cl-Phe) is 4-chlorophenylalanine (NN3APG) is N,N-bis(3-aminopropyl)glycine, (AHX) is aminohexanoic acid, (Lys-P) is Lys-palmitoyl, Thr(ol) is Threoninol, $_DK$, $_DF$, $_DW$ denotes D-isomer, PFHA is 2H, 2H, 3H, 3H-perfluoroheptanoic acid, and ACPA is 8-aminocaprylic acid.

There are also other examples of analogs that can be used other than galanin and somatostatin. For example, analogs of Delta-sleep inducing peptide (DSIP) follow:

DSIP-BBB8: (AHX)GGWAGGDASGE (SEQ ID NO: 55). Additional DSIP peptides can be found in Table 31.

2. Example 2

Anticonvulsant Galanin Analogs

Galanin is a 30-amino-acid neuropeptide, with the N-terminal portion being a highly potent agonist as compared to the whole-length peptide (Langel and Bartfai, 1998). A truncated galanin(1-16) analog (below) was used to introduce modifications that enhance its permeability through the blood-brain-barrier.

```
 1   2   3   4   5   6   7   8   9   10  11  12  13  14  15  16
Gly Trp Thr Leu Asn Ser Ala Gly Tyr Leu Leu Gly Pro His Ala Val
```

The following residues critical for biological activity were identified: $Gly^1$, $Trp^2$, $Asn^5$, $Tyr^9$ and $Gly^{12}$ (Land et al., 1991). The N-terminal extensions or truncations caused a loss of the biological activity. On the other hand, the C-terminal portion of galanin (1-16) is very robust when it comes to either truncations or attaching larger structures (Pooga et al., 1998).

Based on available structure-activity relationship data, two peptide-based galanin analogs were designed, chemically synthesized, and tested. The structures of both analogs (GAL-BBB1 and GAL-BBB2) are provided below:

GAL-BBB1:
Sar-Trp-Thr-Leu-Asn-Ser-Ala-Gly-Tyr-Leu-Leu-Gly-Pro-His-(Lys-palm)-Tle-NH₂

GAL-BBB2:
Sar-Trp-Thr-Leu-Asn-Ser-Ala-Gly-Tyr-Leu-Leu-Gly-Pro-Lys-Lys-(Lys-palm)-Lys-NH₂ where Sar is sarcosine, Tle is tert-Leucine and Lys-palm is lysine residue coupled with palmityoyl moiety via epsilon amino group and —NH₂ denotes amidation at the C-terminus. The peptides were synthesized on solid support using the standard Fmoc chemistry and purified by HPLC. The purified analogs were then tested in the Frings audiogenic-seizure susceptible mouse model of epilepsy. Results from this study were compared to the native galanin peptide fragment (1-16).

Other analogs include the following:

```
GAL-BBB3:                                    (SEQ ID NO: 49)
WTLNSAGYLLGPKKXX-NH2

GAL-BBB4:                                    (SEQ ID NO: 50)
Sar-WTLNSAGYLLGP(D-Lys)(D-Lys)X(D-Lys)-NH2

GAL-BBB5:                                    (SEQ ID NO: 51)
Sar-WTLNSAGYLLGPRRXR-NH2

GAL-BBB6:                                    (SEQ ID NO: 52)
Sar-WTLNSAGYLLGPHHXH-NH2

GAL-BBB7:                                    (SEQ ID NO: 53)
Sar-WTLNSAGYLLKKKKXK-NH2

GAL-BBB8:                                    (SEQ ID NO: 54)
Sar-WTLNSAGYLLKKXK-NH2
``` where Sar is sarcosine, and X is Lys-palmitoyl residue.

The two modified galanin analogs (GAL-BBB1 and GAL-BBB2) were administered i.p. to a group of Frings audiogenic seizure susceptible mice in a dose of 4 mg/kg. At various times after administration (i.e., 15, 30, 60, 120, and 240 min) each mouse was placed into a cylindrical test chamber fitted with an audio transducer and challenged with a high-intensity sound stimulus (110 dB, 11 KHz for 20 sec). Animals not displaying tonic hind-limb extension were considered protected. As summarized in FIG. 12, the results obtained from this study demonstrated that GAL-BBB2 displays a time-dependent anticonvulsant effect that was rapid in onset (within 30 min) and moderate in duration (between two and four hours). In contrast, the other modified galanin analog GAL-BBB1 was not active at any time point tested; even at a higher dose of 12 mg/kg. In a subsequent study, anticonvulsant efficacy was quantitated at the time to peak effect (i.e., 1 h) in a dose-response study. The results of this study demonstrated that GAL-BBB2 displayed a dose-dependent effect against sound-induced seizures. The calculated median effective dose (i.e., ED50) and 95% confidence intervals were obtained from a Probit analysis of the dose-response data was 3.2 (2.3-6.1) mg/kg. The native peptide fragment GAL(1-16) was inactive at a dose of 20 mg/kg, i.p. (six times the $ED_{50}$ for GAL-BBB2) (FIG. 20).

The galanin analog, GAL-BBB2, exhibited potent anticonvulsant activity (ED50~3 mg/kg) when given i.p. This proof-of-concept analog represents the prototype on which more "drug-like" analogs are designed. The smallest galanin analog with the most potent and long-lasting anticonvulsant activity can therefore be obtained. This requires a two-step approach: (1) define the smallest fragment of GAL-BBB2 analog that maintains the anticonvulsant activity: this will include terminal and central truncations, (2) optimize the C-terminal structural motif that will further improve BBB permeability of the analog. The synthesized analogs are first screened in the galanin competitive binding assay. Those analogs that displace galanin at concentrations 1 µM or lower are further screened for anticonvulsant activity using an audiogenic-seizure mouse model of epilepsy. Those analogs that exhibit long-lasting anticonvulsant activity at a single dose (i.e., 2 mg/kg, when given i.p.), are further evaluated in more pharmacological assays. The general experimental strategy is summarized in FIG. 13. FIGS. 23 and 24 shows time-dependent anticonvulsant activity in Frings Mouse and dose-dependent protection against audiogenic seizures in the Frings mouse, respectively, when given GAL-BBB2.

Limited structure-function relationship studies are carried out to identify the minimal fragment of the GAL-BBB2 analog that maintains anticonvulsant activity when administered systemically. Galanin analogs containing either the C-terminal and central truncations are synthesized and tested. In addition, limited structure-function relationship study of the C-terminal motif are carried out to optimize permeability of the analog through the blood-brain-barrier. FIG. 14 illustrates the structure of GAL-BBB2 in the context of structure-function studies.

In order to generate truncated analogs of GAL-BBB2, four consecutive deletions are from the Pro13 to Leu10 residues (summarized in Table 11). Since Tyr9 is critical to the galanin activity, further C-terminal truncations can result in a complete loss of biological activity (reference Land et al, Int J Pept Prot 1991). In each truncated analog, the C-terminal "-Lys-Lys-LysP-Lys" is retained for improved permeability through the BBB.

TABLE 11

Structure of GAL-BBB2 and truncated analogs.

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| Sar | Trp | Thr | Leu | Asn | Ser | Ala | Gly | Tyr | Leu | Leu | Gly | Pro | Lys | Lys | Lys-P | Lys |
| Sar | Trp | Thr | Leu | Asn | Ser | Ala | Gly | Tyr | Leu | Leu | Gly | Lys | Lys | Lys-P | Lys | |
| Sar | Trp | Thr | Leu | Asn | Ser | Ala | Gly | Tyr | Leu | Leu | Lys | Lys | Lys-P | Lys | | |
| Sar | Trp | Thr | Leu | Asn | Ser | Ala | Gly | Tyr | Leu | Lys | Lys | Lys-P | Lys | | | |
| Sar | Trp | Thr | Leu | Asn | Ser | Ala | Gly | Tyr | Lys | Lys | Lys-P | Lys | | | | |

To minimize GAL-BBB2 analog, central truncations between key residues are introduced. This is an alternative strategy to design active peptide analogs with a simplified structure, without compromising the length of a given peptide. Backbone replacement (i.e., "backbone prosthesis") can be achieved by substituting two or more consecutive "non-key" residues with a non-peptide spacer, for example aminovarelic or aminohexanoic acid ("backbone spacer"). This concept is better illustrated in FIG. 15.

In the case of the GAL-BBB2 analog, three parts of the peptide are probed by systematic replacements of residues with a backbone spacer (Table 11): between Trp2 and Asn5, between Asn5 and Tyr9 and between Tyr9 and the C-terminal motif. Approximately 14 of such analogs are synthesized and tested for binding to the galanin receptor. If some analogs maintain the anticonvulsant activity, two or more spacers in different positions can be introduced (see the example in Table 12).

TABLE 12

"Backbone-prosthesis walk" in the GAL-BBB2 analog. Replacement of two residues at a time with non-peptidic backbone spacer, such as aminovaleric or aminohexanoic acids results in a minimization of the overall molecular size without significant change of a spacing between the key pharmacophore residues.

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| Sar | Trp | Thr | Leu | Asn | Ser | Ala | Gly | Tyr | Leu | Leu | Gly | Pro | Lys | Lys | Lys-P | Lys |
| Sar | Trp | spacer | | Asn | Ser | Ala | Gly | Tyr | Leu | Leu | Gly | Pro | Lys | Lys | Lys-P | Lys |
| Sar | Trp | Thr | Leu | Asn | spacer | | Gly | Tyr | Leu | Leu | Gly | Pro | Lys | Lys | Lys-P | Lys |
| Sar | Trp | Thr | Leu | Asn | Ser | spacer | | Tyr | Leu | Leu | Gly | Pro | Lys | Lys | Lys-P | Lys |
| Sar | Trp | Thr | Leu | Asn | Ser | Ala | Gly | Tyr | spacer | | Gly | Pro | Lys | Lys | Lys-P | Lys |
| Sar | Trp | Thr | Leu | Asn | Ser | Ala | Gly | Tyr | Leu | spacer | | Pro | Lys | Lys | Lys-P | Lys |
| Sar | Trp | Thr | Leu | Asn | Ser | Ala | Gly | Tyr | Leu | Leu | spacer | | Lys | Lys | Lys-P | Lys |
| Sar | Trp | Thr | Leu | Asn | Spacer | | | Tyr | Leu | Leu | Gly | Pro | Lys | Lys | Lys-P | Lys |
| Optional: | | | | | | | | | | | | | | | | |
| Sar | Trp | spacer | | Asn | Spacer | | | Tyr | Leu | Leu | Gly | Pro | Lys | Lys | Lys-P | Lys |

Next, the C-terminal structural motif, "-Lys-Lys-LysP-Lys-NH2", can be optimized to improve the BBB permeability. The initial compound, GAL-BBB2 can be optimized by introduction of the following structural changes, summarized in Table 13. Replacements of Lys residues with homo-Lys, D-Lys or diaminobutyric acid probes efficiency of the BBB permeability of positively charged residues with varying lipophilic nature of their side chains. Replacement of Lys-palmitoyl moiety in the position 16 with 2-amino-tetradecanoic acid or 3,3-diphenylalanine determines how flexible is this position to other hydrophobic residues that can also enhance the BBB permeability.

TABLE 13

Modification of the C-terminal motif that enhances permeability of the galanin analogs through the BBB.

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| Sar | Trp | Thr | Leu | Asn | Ser | Ala | Gly | Tyr | Leu | Leu | Gly | Pro | Lys | Lys | Lys-P | Lys |
| Sar | Trp | Thr | Leu | Asn | Ser | Ala | Gly | Tyr | Leu | Leu | Gly | Lys | Lys | Lys | Lys-P | Lys |
| Sar | Trp | Thr | Leu | Asn | Ser | Ala | Gly | Tyr | Leu | Leu | Lys | Lys | Lys | Lys | Lys-P | Lys |
| Sar | Trp | Thr | Leu | Asn | Ser | Ala | Gly | Tyr | Leu | Leu | Gly | Pro | Lys | Lys | Lys | Lys |
| Sar | Trp | Thr | Leu | Asn | Ser | Ala | Gly | Tyr | Leu | Leu | Gly | Pro | Lys | Lys-P | Lys | Lys |
| Sar | Trp | Thr | Leu | Asn | Ser | Ala | Gly | Tyr | Leu | Leu | Gly | Pro | Lys-P | Lys | Lys | Lys |
| Sar | Trp | Thr | Leu | Asn | Ser | Ala | Gly | Tyr | Leu | Leu | Gly | Pro | D-Lys | D-Lys | Lys-P | D-Lys |
| Sar | Trp | Thr | Leu | Asn | Ser | Ala | Gly | Tyr | Leu | Leu | Gly | Pro | h-Lys | h-Lys | Lys-P | h-Lys |
| Sar | Trp | Thr | Leu | Asn | Ser | Ala | Gly | Tyr | Leu | Leu | Gly | Pro | DAB | DAB | Lys-P | DAB |
| Sar | Trp | Thr | Leu | Asn | Ser | Ala | Gly | Tyr | Leu | Leu | Gly | Pro | Lys | Lys | TDA | Lys |
| Sar | Trp | Thr | Leu | Asn | Ser | Ala | Gly | Tyr | Leu | Leu | Gly | Pro | Lys | Lys | DPA | Lys |

TDA is 2-amino-tetradecanoic acid, DAB is diaminobyturicc acid, D-Lys is D-isomer of Lys and h-Lys is homo-Lys, DPA is 3,3-diphenylamine

| Sar | Trp | Thr | Leu | Asn | Ser | Ala | Gly | Tyr | Leu | Leu | Gly | Pro | Lys | Lys | Lys-P | Lys | X |

In addition to the above list of analogs, two analogs with a lipophilic, non-peptidic extension at the C-terminus can be produced, as shown below:

where X denotes: 12-amino-dodecanoic acid or 2-amino-tetradecanoic acid.

As illustrated in FIG. 13, each synthesized and purified analog is tested for its binding properties to galanin receptors. Only those analogs that displace full-length galanin at concentration 1 µM or lower are studied further. Galanin binding assays can be performed by Novascreen Biosciences Corporation, for example. Rat forebrain membranes and radiolabeled parent neuropeptides can be used in these assays. The analogs can be tested at a single (1 µM) concentration to distinguish between high- and low-affinity analogs. The agonist activity of selected galanin analogs can be further tested using functional assays provided by MDS-Pharma Services. For example, the analogs can be tested at a single concentration (1 µM).

The below table summarizes various SAR analogs, and the percentage of protection afforded at 1, 2 and 4 hours by a dose of 4 mg/kg, i.p.

electroshock (MES) and subcutaneously (s.c.) administered pentylenetetrazol (PTZ). These two tests measure the ability of an investigational antiepileptic compound to prevent seizure spread and elevate seizure threshold, respectively (White et al., 2002). Once a modified peptide has been demonstrated to be active in one or more of these three seizure tests, complete dose-response studies are conducted at the previously determined time of peak effect following i.p. administration. Results from these proof-of-concept studies are then be compared to efficacy studies conducted following intracerebroventricular (i.c.v.) administration. A leftward shift in the i.p. dose-response curve can be observed as greater penetration of the blood-brain barrier is achieved. Collectively, the results obtained from these three seizure tests provides substantial data supporting the approach to make small peptides more accessible to the brain following systemic administration. The details of each individual seizure test are outlined below.

Administration of Neuropeptide Analogs.

Each of the modified galanin analogs are administered intracerebroventricularly (i.c.v.) in 5 µl artificial cerebrospi-

TABLE 14

| NAX | Structure | % Protection at 1, 2 and 4 hours afforded by a dose of 4 mg/kg, i.p. |
|---|---|---|
| Gal(1-16) | GWTLNSAGYLLGPHAV (SEQ ID NO: 1) | Not active |
| 5055 | (Sar)WTLNSAGYLLGPKK(Lys-P)K (SEQ ID NO: 56) | 100%, 100%, 0% (0.8 mg/kg) |
| Subtype selectivity | | |
| 1205-1 | WTLNSAGYLLGPKK(Lys-P)K (SEQ ID NO: 57) | 50%, 50%, 0%, * (5.7 mg/kg) |
| "KKKpK" motif | | |
| 1205-2 | (Sar)WTLNSAGYLLGPDKDK(Lys-P)DK (SEQ ID NO: 50) | 100%, 50%, 75% (1.2 mg/kg) |
| 1205-3 | (Sar)WTLNSAGYLLGPRR(Lys-P)R (SEQ ID NO: 59) | 100%, 75%, 0% |
| 1205-4 | (Sar)WTLNSAGYLLKKKK(Lys-P)K (SEQ ID NO: 60) | 75%, 100%, 66%, * |
| 1105-2 | (Sar)WTLNSAGYLLGPKKKK (SEQ ID NO: 61) | 30%, 0%, 0% (3.7 mg/kg) |
| Truncations | | |
| 1205-5 | (Sar)WTLNSAGYLLKK(Lys-P)K (SEQ ID NO: 62) | 100%, 25%, 0% (2.8 mg/kg) |
| 306-3 | (Sar)WTLNSAGYKK(Lys-P)K (SEQ ID NO: 63) | 75%, 25%, 0% (2.7 mg/kg) |
| Backbone spacers | | |
| 306-2 | (Sar)WTLNSAGYLLGP(Ahx)KK(Lys-P)K (SEQ ID NO: 64) | 100%, 75%, 0%, * |
| 306-4 | (Sar)WTLNSAGY(Ahx)KK(Lys-P)K (SEQ ID NO: 65) | 50%, 0%, 0% (2.95 mg/kg) |

Anticonvulsant activity can first be established in the Frings AGS-susceptible mouse model of reflex epilepsy. The AGS-susceptible mouse is the ideal acute seizure model because it is non-discriminatory, and effectively detects a wide variety of CNS active compounds (White et al., 1992). Peptides found to be active in the Frings mouse can be evaluated for their ability to block seizures induced by maximal nal fluid via a 10 µl Hamilton syringe or intraperitoneally (i.p.) in 0.5% methylcellulose in a volume of 0.01 ml/g body weight.

Audiogenic Seizures.

The ability of individual modified analogs to prevent seizures induced by sound in the AGS-susceptible Frings mouse model can be assessed at the time of peak effect (White et al., 1992). For this test, individual mice are placed into a plexiglass cylinder (diameter, 15 cm; height, 18 cm) fitted with an audio transducer (Model AS-ZC; FET Research and Development, Salt Lake City, Utah), and exposed to a sound stimulus of 110 decibels (11 KHz) delivered for 20 seconds. Sound-induced seizures are characterized by wild running followed by loss of righting reflex with forelimb and hindlimb tonic extension. Mice not displaying hindlimb tonic extension are considered protected.

MES Test.

For the MES test, a drop of anesthetic/electrolyte solution (0.5% tetracaine hydrochloride in 0.9% saline) is applied to the eyes of each animal prior to placement of the corneal electrodes. The electrical stimulus in the mouse MES test is 50 mA delivered for 0.2 sec by an apparatus similar to that originally described by Woodbury and Davenport (Woodbury and Davenport, 1952). Abolition of the hindleg tonic extensor component of the seizure is used as the endpoint.

s.c. PTZ Test.

For the s.c. PTZ test, a dose of 85 mg/kg PTZ is s.c. into a loose fold of skin on the back of each mouse. Mice will be placed into individual plexiglas observation boxes and observed for 30 minutes for the presence of a minimal clonic seizure. Mice not displaying clonic seizure activity will be considered protected.

Minimal Toxicity Tests.

Minimal toxicity will be identified in mice by the rotarod procedure (Dunham and Miya, 1957). When a mouse is placed on a 1-inch knurled rod that rotates at a speed of 6 r.p.m., the animal can maintain its equilibrium for long periods of time. The animal is considered toxic if it falls off this rotating rod three times during a 1-minute period.

Determination of Median Effective ($ED_{50}$) or Toxic Dose ($TD_{50}$).

All quantitative in vivo anticonvulsant/toxicity studies are conducted at the previously determined TPE. Groups of at least eight mice are tested with various doses of the peptide until at least two points have been established between the limits of 100% protection or minimal toxicity, and 0% protection or minimal toxicity. The dose of drug required to produce the desired endpoint in 50% of animals ($ED_{50}$ or $TD_{50}$) in each test, the 95% confidence interval, the slope of the regression line, and the S.E.M. of the slope are calculated by a computer program based on the method described by Finney (Finney, 1971).

3. Example 3

GAL-BBB2 Possesses Potent Pain Relief a) Formalin Test

An injection of 0.5% formalin is made into the planter region of a mouse right hind paw. This elicits a distinct biphasic behavioral profile characterized by the mouse licking the affected paw. Immediately following the injection the mouse licks the paw for about 10 minutes. This is phase 1 (acute) and is followed by a brief latent period where there is little behavioral activity. A more prolonged period of about 20 to 30 minutes of paw licking ensues which constitutes phase 2 (inflammatory).

Prior to the administration of the active peptide, drug or vehicle each mouse undergoes a 15-minute conditioning period in one of several 6" tall plexiglass observation tubes (4" diameter) that are placed in front of a mirror. Following the conditioning period, mice were treated i.p. with either GAL-BBB2, the inactive native fragment Gal 1-16, or gabapentin then returned to its home tube. One hour after treatment, formalin was injected sub-dermally (20 μl; 27 gauge needle) into the plantar surface of the right hind foot. The bevel of the needle is placed facing down toward the skin surface. Following the injection of the formalin each animal is observed for first 2 minutes of each 5 minute epoch for a total of 45 minutes. The cumulative length of licking for each 2 minute time period was measured. An animal receiving the requisite volume of vehicle was alternated with each mouse given GAL-BBB2, Gal 1-16, or gabapentin. Animals were euthanized following the conclusion of the experiment.

In a further experiment (in table below), two additional galanin analogs with unique structural motifs (i.e., NAX 306-3 and 306-4) were found to be potent, as well as NAX 5055, in the mouse formalin assay of inflammatory pain. These findings show that the active pharmacophore is amenable to structural modifications.

TABLE 15

| NAX | Structure | Active at: |
|---|---|---|
| 5055 | (Sar)WTLNSAGYLLGPKK(Lys-P)K (SEQ ID NO: 56) | 5 mg/kg ("flat phase II") |
| 306-3 | (Sar)WTLNSAGYKK(Lys-P)K (SEQ ID NO: 66) | 2.7 mg/kg ("flat phase II") |
| 306-4 | (Sar)WTLNSAGY(Ahx)KK(Lys-P)K (SEQ ID NO: 67) | 2.9 mg/kg ("flat phase II") |

Area under the curve (AUC) determination was made using the GraphPad Prism Version 3.03. Total AUC is calculated for both the test and control groups for both the acute and inflammatory phases. The AUC for individual animals for each phase is also calculated and converted to percentage of total AUC of control. The average percentages and SEM for both the drug treated and control were calculated and tested for significant difference.

b) Ligation of the Sciatic Nerve

Just prior to surgery, rats are treated subcutaneously with 0.1 to 0.5 mg/kg of the long acting opiate buprenorphine. Rats are then anesthetized with pentobarbital and the depth of anesthesia monitored by their response to a tail pinch and observation of the depth of respiration. Sterile technique was used throughout the surgery.

The upper thigh of each rat was shaved and wiped off with ethanol and betadine. A small incision was made in the skin and through the underlying muscle of the upper thigh until the sciatic nerve was exposed. The nerve was then separated from the surrounding connective tissue and slightly elevated by a pair of fine, curved forceps. Approximately ⅓ to ½ of the nerve was then tied off by passing a needle and nylon suture (7.0) through the nerve. The muscle and skin incision was then closed sutured separately with 5.0 suture and the animals were kept warm by placing on a thermostatically controlled heat blanket until they have recovered from the anesthesia. This procedure was conducted on the right side (ipsilateral) while a sham surgery was performed on the left hind leg (contralateral). The latter involves a similar procedure with the exception that the sciatic nerve on this side was only exposed and not ligated. Twelve hours post surgery, a second dose of buprenorphine was administered to minimize any discomfort from the surgical procedure. Rats were closely monitored daily for the development of infection or untoward effects of the surgery.

After an appropriate time for recovery (e.g., 7-14 days) the animals were tested for the development of mechanical allodynia (pain response to a non-noxious stimulus). For this study, the animals placed in a bottomless plexiglass box placed on a wire mesh (¼") platform. After a 30-60 minute acclimation period, a baseline mechanical sensitivity was determined. This procedure was done by applying a series of calibrated Von Frey fibers perpendicularly to the plantar surface of each hind paw and holding it there for about 6 secs with enough force to slightly bend the fiber. After a positive response (withdrawal of the foot) is noted a smaller diameter fiber was applied. This procedure was repeated until a 50% threshold for withdrawal could be determined.

Following i.p. injection of 2 mg/kg GAL-BBB2 (n=8 rats per drug) the mechanical threshold was assessed 30 min post-injection and at various times thereafter (e.g., 1, 2, 4, and 6 h) to determine the duration of action of the test compound. Results obtained with GAL-BBB2 were compared to those obtained with 2 mg/kg morphine, and 40 mg/kg gabapentin.

c) Results

A number of anticonvulsants have demonstrated efficacy in the treatment of pain. Therefore, GAL-BBB2 was examined in the mouse formalin model to assess whether it possessed analgesic properties. In this test, GAL-BBB2 was found to significantly reduce the pain associated with s.c. plantar formalin as estimated by quantification of the time that an animal spends licking the ipsilateral paw. As shown in FIG. 16, GAL-BBB2 (0.52-5 mg/kg) produced a dose-dependent reduction in paw licking during both the initial acute phase as well as the prolonged inflammatory phase. In contrast, the un-modified native fragment Gal 1-16 was found to be inactive following i.p. administration of a dose 4 times higher than the highest dose of GAL-BBB2 tested (i.e., 20 mg/kg). In addition, 5 mg/kg GAL-BBB2 (FIG. 16) was found to be equivalent to a 10 mg/kg dose of gabapentin (FIG. 17).

As shown in FIG. 18, GAL-BBB2 displayed a time-dependent increase in the threshold for mechanical allodynia in the sciatic ligation model of chronic pain. Furthermore, GAL-BBB2 was equi-potent to morphine and several fold more potent that gabapentin in this test (inset to FIG. 18).

Collectively, the results obtained in these two established models of pain show that GAL-BBB2 possesses potent pain relief in rodent models of chronic pain.

4. Example 4

Galanin Analogs that Penetrate the Blood-Brain-Barrier

Table 16 shows galanin analogs that can be used with the compositions and methods disclosed herein:

```
(Sar)WTLNSAGY(D-Lys)(D-Lys)(Lys-P)(D-Lys)  (SEQ ID NO: 119)          Gal-BBB25

(Sar)WTLNSAGY(Ahx)(D-Lys)(D-Lys)(Lys-P)(D-Lys)  (SEQ ID NO: 120)     Gal-BBB26

(Sar)WTLNSAGY(7-Ahp)(D-Lys)(D-Lys)(Lys-P)(D-Lys)  (SEQ ID NO: 121)   Gal-BBB27

(Sar)WTLNSAGY(3,5-dibromo-Tyr)LLGPKK(Lys-P)K  (SEQ ID NO: 122)       Gal-BBB28

(Sar)WTLNSAGYLLGPHH(Lys-P)K  (SEQ ID NO: 123)                        Gal-BBB29

(Sar)WTLNSAGYLLGPKK(Cys-Mmt)K  (SEQ ID NO: 124)                      Gal-BBB30

(Sar)WTLNSAGYLLGPKK(Lys-Biotin-anainocaproyl)K  (SEQ ID NO: 125)     Gal-BBB31

(Sar)WTLNSAGYLLGPKK(Lys-sterol)K  (SEQ ID NO: 126)                   Gal-BBB32

(Sar)WTLNSAGYLLGPKK(Lys-decanoyl)K  (SEQ ID NO: 127)                 Gal-BBB33

(Sar)WTLNSAGYLLGPKK(Lys-octanoyl)K  (SEQ ID NO: 128)                 Gal-BBB34

(Sar)WTLNSAGYLLGPKK(Lys-linoyl)K  (SEQ ID NO: 129)                   Gal-BBB35

(Sar)WTLNSAGYLLGPKK(Ser-melbiose)K  (SEQ ID NO: 130)                 Gal-BBB36

(Sar)WTLNSAGYLLGPKK(Lys-adamentoyl)K  (SEQ ID NO: 131)               Gal-BBB37

(Sar)WTLNSAGYLLGPKK(Glu(β-Lac-PEG₃-amine))K  (SEQ ID NO: 132)        Gal-BBB38

(Sar)WTLTSAGYLLGPKK(Lys-palmitoyl)K  (SEQ ID NO: 133)                Gal-BBB39

(Sar)WTLLSAGYLLGPKK(Lys-palmitoyl)K  (SEQ ID NO: 134)                Gal-BBB40

(Sar)WTLDSAGYLLGPKK(Lys-palmitoyl)K  (SEQ ID NO: 135)                Gal-BBB41
```

Lipophilicity and basicity contribute to increased permeability of peptides through the BBB without the need for specific transporters or carriers. The lipophilic character of a peptide (measured by a logP value) may be altered by either conjugation of a hydrophobic moiety (e.g., lipoamino acids), or halogenation of aromatic residues. Regarding the basicity, the Poduslo group showed that polyamine-modified proteins and peptides cross the BBB more efficiently (Poduslo and Curran 1996; Poduslo and Curran 1996; Poduslo, Curran et al. 1998; Poduslo, Curran et al. 1999). Tamai and coworkers (Tamai, Sai et al. 1997) provided evidence that the increased basicity of small peptides was an important determinant of transport through the BBB via absorptive-mediated endocytosis (AME).

Glycosylation appeared as a very efficient approach to produce systemically-active opioid peptides (Elmagbari, Egleton et al. 2004; Polt, Dhanasekaran et al. 2005). SAR studies showed that the structure of saccharides was an important determinant of the activity, but monosaccharides were generally less effective than disaccharides. O-glycosylated serine with beta-melibiose or beta-lactose were among the most efficient modifications that yielded potent analgesic compounds.

Role of galanin and its receptors in epilepsy and epileptogenesis. Neuropeptides are potent modulators of classic neurotransmitters and neuronal excitability (Hokfelt, Broberger et al. 2000). Coexistence of neuropeptides with classic neurotransmitters in select neuronal populations implies that neuronal excitability can be regulated through modification of peptidergic transmission (Baraban and Tallent 2004). Under ambient conditions, peptides are "silent" and exert little effect on normal neurotransmission. In contrast, under conditions of excessively high neuronal firing (as occurs in a seizure focus), neuropeptides are released and exert a modulatory effect on neurotransmission.

Galanin produces multiple effects in the brain (Hokfelt, Xu et al. 1998; Landstrom, Elmquist et al. 2005). Three galanin receptor subtypes identified to date belong to the superfamily of G protein coupled receptors (GPCR) (Branchek, Smith et al. 2000; Landstrom, Elmquist et al. 2005). Galanin receptor type 1 (GalR1) is present in many brain areas, but displays the highest expression in the hippocampus (Burgevin, Loquet et al. 1995). The galanin receptor type 2 (GalR2) is as widely distributed as GalR1. In the brain it is expressed in the hypothalamus, the hippocampus (dentate gyrus>CA3>CA1), the amygdala, piriform cortex, basal forebrain (medial septum/diagonal band), the cerebellum, and the brainstem. Galanin receptor type 3 (GalR3) exhibits very restricted expression in the brain. It is most abundant in the hypothalamus, medial reticular formation and diagonal band, and is absent from the hippocampus.

Since the pioneer work of Mazarati and coworkers (Mazarati, Halaszi et al. 1992), there has been increasing evidence that galanin is a potent anticonvulsant peptide. The acute administration of galanin receptor agonists or virus-mediated overexpression of galanin in the hippocampus has been found to inhibit limbic status epilepticus, pentylenetetrazol and picrotoxin seizures in rats and mice (Mazarati, Halaszi et al. 1992; Mazarati, Liu et al. 1998; Saar, Mazarati et al. 2002; Haberman, SamulsId et al. 2003; Lin, Richichi et al. 2003; Bartfai, Lu et al. 2004). Furthermore, the seizure threshold of galanin overexpressing transgenic animals is increased in status epilepticus and kindling models (Mazarati, Hohmann et al. 2000; Kokaia, Holmberg et al. 2001; Schlifke, Kuteeva et al. 2006).

In vitro, galanin inhibits glutamate release from the hippocampus (Zini, Roisin et al. 1993; Mazarati, Hohmann et al. 2000). Results obtained from studies with GalR1 knockout mice and rats treated with GalR2 peptide nucleic acid antisense suggests that galanin exerts its anticonvulsant effect through an action at both GalR1 and GalR2 (Mazarati, Lu et al. 2004; Mazarati, Lu et al. 2004). Furthermore, GalR2 is thought to play an important role in the neuroprotective effects of galanin in hippocampal neurons (Haberman et al., 2003; Mazarati et al., 2004a; Pirondi et al., 2005; Elliot-Hunt et al., 2004; Lee et al., 2005; Hwang et al., 2004).

It should be emphasized that galanin is effective in preventing the expression of acute seizures and modifying the development of epilepsy following various insults. For example, several reports have shown that galanin can modify the damage associated with limbic seizures and delay or prevent the development of epilepsy (i.e. antiepileptogenic). Kokaia et al. (Kokaia, Holmberg et al. 2001) reported delayed kindling in galanin peptide overexpressing mice. Results from a recent study in a model of rapid kindling show that hippocampal GalR2 coupled to $G_{i/o}$ protein exerts an antiepileptogenic effect independent of GIRK, while GalR1 delays the acquisition of kindling by GIRK activation (Mazarati, Lundstrom et al. 2006).

Structure-activity-relationships (SAR) in galanin and galanin receptor ligands. Galanin was first discovered in 1983 (Tatemoto, Rokaeus et al. 1983). It is a 29-30 amino acid long peptide with the following sequence:

| | | |
|---|---|---|
| Human | GWTLNSAGYLLGPHAVGNHRSFSDKNGLTS-COOH | (SEQ ID NO: 93) |
| Rat/mouse | GWTLNSAGYLLGPHAIDNHRSFSDKHGLT-NH2 | (SEQ ID NO: 94) |
| Porcine | GWTLNSAGYLLGPHAIDNHRSFHDKYGLA-NH2 | (SEQ ID NO: 95) |

The first N-terminal 14 residues (shaded) are highly conserved among galanin sequences from different animal species (Langel and Bartfai 1998). Since the structure-activity-relationship of galanin has been extensively studied we will only review those SAR results that are relevant to this grant application. The N-terminal fragments of GAL, consisting of the first 15 residues (analog GAL(1-15)) or 16 residues (analog GAL(1-16)) have been shown to maintain high affinity toward galanin receptors (Fisone, Berthold et al. 1989; Land, Langel et al. 1991). As shown in the following table, systematic truncation of GAL(1-16) results in a gradual decrease of the affinity toward its receptors (Land, Langel et al. 1991).

TABLE 17

Effects of truncation of GAL(1-16) fragment on its affinity towards galanin receptors.

| Fragment | Sequence | $K_D$ [µM] |
|---|---|---|
| 1-16 | GWTLNSAGYLLGPHAI (SEQ ID NO: 96) | 0.007 |
| 1-14 | GWTLNSAGYLLGPH (SEQ ID NO: 97) | 0.15 |
| 1-12 | GWTLNSAGYLLG (SEQ ID NO: 98) | 3 |
| 1-10 | GWTLNSAGYL (SEQ ID NO: 99) | 25 |
| 1-9 | GWTLNSAGY (SEQ ID NO: 100) | 100 |

In the same study, the authors demonstrated that the Gly1, Trp2, Asn5, Tyr9 and Gly12 residues are important for high affinity binding of the GAL(1-16) analog to the galanin receptors. Alanine-walk analogs of GAL(1-16) indicated that replacement of the these residues affects their affinity toward GalR2, rather than GalR1 (Carpenter, Schmidt et al. 1999). An alanine-shaving approach revealed that a sequence spanning from Tyr9 to His 14 was critical for recognition of galanin receptors (Jureus, Langel et al. 1997).

A very extensive SAR study of the GAL(1-16) analog was described by (Pooga, Jureus et al. 1998). Modification of Gly1 or Trp2 resulted in a significant loss of affinity toward galanin receptors. All analogs of GAL(1-13) with Lys14 epsilon-NH group coupled to different groups varying in size retained high affinity. Based on these results, the C-terminal part of GAL(1-13) can accommodate relatively bulky groups without compromising binding properties. In summary, the SAR of galanin and its truncated analogs indicate that Trp2, Asn5 and Tyr9 are key residues for protecting an interaction between galanin and GalR1 and GarR2 receptors. Mutagenesis and modeling studies show that Trp2 interacts with Phe282 of hGalR1, whereas Tyr9 with His264 (Kask et al, 1996; Berthold et al 1997; Church et al, 2002).

As a result of extensive structure-activity relationship studies, a number of peptide-based galanin analogs, both agonists and antagonists, have been synthesized and functionally characterized. The binding properties of selected galanin receptor ligands is summarize in Table 18.

TABLE 18

Selected galanin receptor ligands and their binding properties to different galanin receptor subtypes.

| Ligand | Affinity[a], $K_D$ [nM] | | |
|---|---|---|---|
| | hGalR1 | hGalR2 | hGalR3 |
| Agonists | | | |
| hGAL(1-29) | 9.4 | 8.6 | 7.1 |
| GAL(1-16) | 8.5 | 8.3 | 6.5 |
| GAL(2-11) | 879 | 1.8 | n.d. |
| Agonists that cross blood-brain-barrier | | | |
| Galnon | 12,000 | 24,000 | n.d. |
| Galmic | 34,000 | >100,000 | n.d. |
| Analog 5055[b] | ~9 | ~6 | n.d. |
| Antagonists | | | |
| M35 | 0.1 | 2 | 15 |
| M15 (galantide) | 0.3 | 1 | 40 |

[a]$K_D$ values were compiled from (Branchek, Smith et al. 2000; Lundstrom, Elmquist et al. 2005; Lundstrom, Sollenberg et al. 2005; Sollenberg, Lundstrom et al. 2006). Galnon and galmic are two non-peptide galanin receptor agonists that have become very useful pharmacological tools to study the effects of galanin receptors in the CNS (Saar, Mazarati et al. 2002; Bartfai, Lu et al. 2004; Badie-Mahdavi, Behrens et al. 2005; Lu, Barr et al. 2005; Schlifke, Kuteeva et al. 2006). However, as recently stated: "The drawback of galnon and galmic are that they are low affinity (micromolar affinities), non-receptor subtype selective, and interacting with other pharmacologically important targets . . ." (Lu, Lundstrom et al. 2005).

Rational Design and Chemical Synthesis of NAX 5055, a Galanin Analog that Penetrates the BBB.

As disclosed herein, galanin is a 30-amino-acid neuropeptide, and it has been demonstrated that the N-terminal fragment GAL(1-16) is still a highly potent agonist at the hippocampal galanin receptor (Fisone, Berthold et al. 1989). Results obtained to date were obtained with a truncated GAL(1-16) analog (FIG. 31) that has been modified in a way to increase metabolic stability, and improve permeability through the BBB.

Based on available structure-activity relationship data, the following modifications were introduced to the GAL(1-16) analog to improve its metabolic stability and permeability through the BBB: (1) Gly1 residue was replaced by Sarcosine. N-methylation of Gly1 does not affect galanin receptor affinity (Rivera Baeza, Kask et al. 1994). Furthermore, aminopeptidases N are known to degrade neuropeptides, and thus capping of the N-terminal amino group is likely to decrease the rate of metabolic degradation of Sarcosine-containing analogs; (2) His14 and Ala15 were replaced by Lys residues. Amidated Lys residue was added to the C-terminus. These additional positive charges increase BBB permeability mediated through adsorptive-mediated endocytosis (Tamai, Sai et al. 1997); (3) Val16 was replaced by Lysine-palmitoyl (Lys-palm) residue. This long, hydrophobic can increase passive diffusion, and provide additional resistance to metabolic degradation (Yuan, Wang et al. 2005). NAX 5055 was chemically synthesized on a solid support using the standard Fmoc protocols and automated peptide synthesizer.

Pharmacological Properties of NAX 5055.

To date, NAX 5055 has been evaluated in a radioligand binding assay and a battery of in vivo acute seizure tests. The results obtained from these investigations show that the approach disclosed herein can yield potent, high affinity galanin receptor modulators that penetrate the BBB.

NAX 5055 Retains High Affinity Towards GalR1 and GalR2.

Affinity of NAX 5055 for human hGalR1 and hGalR2 was confirmed in a preliminary radioligand binding study that was conducted by MDS-PS contract screening company (report#1077561, reference: MDSPS 231510 and 231600). In this study, hGalR1 was expressed in HEK-293 cells, whereas hGalR2 was expressed in CHO-K1 cells and human [$^{125}$I] galanin was used as the radioligand. NAX 5055 retained high affinity toward both subtypes with an estimated Ki of 9 nM for hGalR1 and 6 nM for hGalR2.

NAX 5055 Displays Potent Anticonvulsant Activity Following Systemic Administration. NAX 5055 was initially tested in the Frings audiogenic seizure (AGS)-susceptible mouse model of reflex epilepsy following i.p. administration of 4 mg/kg. At various times after administration (i.e., 15, 30, 60, 120, and 240 min) each mouse was placed into a cylindrical test chamber fitted with an audio transducer and challenged with a high-intensity sound stimulus (110 dB, 11 KHz for 20 sec).

Animals not Displaying Tonic Hind-Limb Extension were Considered Protected.

As shown in FIG. 24, the results obtained from this experiment demonstrate that NAX5055 displays a time-dependent anticonvulsant effect that is rapid in onset (within 30 min) and moderate in duration (between two and four hours). In a subsequent dose-response study, anticonvulsant efficacy was quantitated at the time to peak effect (i.e., 1 h). The calculated median effective dose (i.e., ED50) and 95% confidence intervals obtained from a Probit analysis of the dose-response data was 3.2 (2.3-6.1) mg/kg. When tested one-hour after i.p. administration, NAX 5055 (4 mg/kg), but not the native GAL (1-16) fragment (20 mg/kg) was effective in blocking sound-induced seizures in the Frings mouse.

NAX 5055 was also tested in two well-established seizure models; i.e., the maximal electroshock seizure (model of generalized tonic-clonic epilepsy) and the s.c. Metrazol-seizure test (model of generalized myoclonic epilepsy). For this study, 4 mg/kg NAX 5055 was administered i.p. and mice were tested one-hour later for protection against tonic-extension (maximal electroshock) and clonic (s.c. Metrazol) seizures. NAX 5055 was minimally active (25% protection) in the s.c. Metrazol seizure test and was completely inactive in the maximal electroshock seizure test (results not shown). Although these results might be interpreted as negative from a clinical efficacy point of view, the profile of NAX 5055 described thus far is virtually identical to that of the novel antiepileptic drug levetiracetam which was introduced in 2000 for the treatment of human partial seizures.

Thus, in an effort to expand the anticonvulsant profile of NAX 5055, we have also evaluated it in another levetiracetam-sensitive acute seizure model; i.e., the 6 Hz psychomotor test. The 6 Hz seizure test is evolving as a unique model for differentiating potential anticonvulsant compounds that might be useful for the treatment of refractory partial epilepsy (Barton, Klein et al. 2001; White 2003). NAX 5055 is very potent following in this model of pharmaco-resistant epilepsy following i.p. administration (Table 19). Unlike levetiracetam and even valproic acid, the potency of NAX 5055 is retained as the stimulus intensity is increased from 22 to 44 mA. Thus, NAX 5055 is relatively unique among the anticonvulsant drugs tested in the 6 Hz test in that it remains very potent at all three current intensities evaluated. In contrast, the potency of the other drugs decreases as the stimulation intensity is increased from 22 to 44 mA. NAX 5055 was subsequently tested in the mouse 6 Hz limbic seizure model following subcutaneous (s.c.) administration. Interestingly, activity is preserved following s.c. administration (FIG. 26). The finding that there was only a slight rightward shift in the ED50 of NAX following s.c. administration shows that NAX 5055 possesses good bioavailability.

In an effort to confirm that the native peptide fragment is active when it has access to the brain, a subsequent study was conducted wherein NAX 5055 and GAL (1-16) were both administered directly into the ventricular space. Results obtained from this intracerebroventricular (i.c.v.) study are summarized in FIG. 22. As shown in FIG. 22, both analogs were very potent (i.e., $ED_{50}$'s:0.07 and 1.7 nmoles for NAX 5055 and GAL(1-16) respectively) following i.c.v. administration. It is interesting to note that NAX 5055 may actually be more potent and efficacious than the native peptide fragment GAL(1-16).

TABLE 19

PHARMACOLOGY OF 6 Hz MODEL

| AED | 22 mA | 32 mA | 44 mA |
|---|---|---|---|
| Phenytoin | 9.4 (4.7-14.9) | >60 | >60 |
| Lamotrigine | 4.4 (2.2-6.6) | >60 | >60 |
| Ethosuximide | 86.9 (37.8-156) | 167 (114-223) | 600 |
| Levetiracetam | 4.6 (1.1-8.7) | 19.4 (9.9-36.0) | 1089 (787-2650) |
| Valporic acid | 41.5 (16.1-68.8) | 126 (94.5-152) | 310 (258-335) |
| NAX 5055 | <4 | 2.9 (2.2-4.0) | 5.5 (4.6-8.5) |

Structure—Activity Relationships of the NAX 5055 analog. SAR studies have been carried out in an effort to better understand structural determinants of its activity following systemic administration. First, it was tested whether individual chemical modifications at the C-terminus could produce comparable effects as compared to the combination of both modifications. As shown below, none of individual modifications had a long-lasting and potent anticonvulsant activity, as compared to NAX 5055. The analog 1105-2 exhibited lower potency ($ED_{50}$=3.8 mg/kg, as compared to 0.8 mg/kg for 5055), shorter duration of action and toxicity (motor impairment) not observed in 5055. Presence of the Lys-palm residue was insufficient to produce any observable anticonvulsant activity. These results strongly suggested that the combination of both modifications is very important for pharmacological properties of the 5055 analog.

TABLE 20

| Analog | Structure | % Protection at 1, 2 and 4 hours afforded by a dose of 4 mg/kg, i.p. |
|---|---|---|
| Gal(1-16) | GWTLNSAGYLLGPHAV (SEQ ID NO: 1) | Not active |
| 5055 | (Sar)WTLNSAGYLLGPKK(Lys-P)K (SEQ ID NO: 56) | 100%, 100%, 0% |
| 1105-2 | (Sar)WTLNSAGYLLGPKKKK (SEQ ID NO: 60) | 30%, 0%, 0%, toxic |
| 306-5 | (Sar)WTLNSAGYLLGPHA(Lys-P) (SEQ ID NO: 68) | Not active |

Note:
all analogs, including NAX 5055 are amidated at the C-terminus.

Secondly, a role of Lys residues at the C-terminus was investigated by replacing Lys with $_D$Lys, or Arg, or by changing a number of Lys residues. Replacing Lys with Arg only slightly changed the activity of the analog. Replacing Lys with its isomer $_D$Lys resulted in a longer-lasting analog (1205-2) with comparable potency ($ED_{50}$=1.2 mg/kg). Replacing Gly12-Pro13 with two additional Lys residues maintained the anticonvulsant activity, but also generated toxicity. Results from these experiments are summarized below in Table 21:

| NAX | Structure | % Protection at 1, 2 and 4 hours afforded by a dose of 4 mg/kg, i.p. |
|---|---|---|
| 5055 | (Sar)WTLNSAGYLLGPKK(Lys-P)K (SEQ ID NO: 56) | 100%, 100%, 0% |

-continued

| NAX | Structure | % Protection at 1, 2 and 4 hours afforded by a dose of 4 mg/kg, i.p. |
|---|---|---|
| 1205-2 | (Sar)WTLNSAGYLLGP$_D$K$_D$K(Lys-P)$_D$K (SEQ ID NO: 69) | 100%, 50%, 75% |
| 1205-3 | (Sar)WTLNSAGYLLGPRR(Lys-P)R (SEQ ID NO: 70) | 100%, 75%, 0% |
| 1205-4 | (Sar)WTLNSAGYLLKKKK(Lys-P)K (SEQ ID NO: 71) | 75%, 100%, 66%, toxic |

Next, functional consequences of central truncation of NAX 5055 were determined. As shown in Table 22, a truncation of Gal(1-16) by "G12,P13" or "L10,L11,G12,P13" reduced the affinity toward galanin receptors by at least two orders of magnitude. Systematic central truncations of the 5055 analog (analogs 1205-5 and 306-3) produced only slightly lower potency in the 6 Hz model (ED$_{50}$=2.7 mg/kg both analogs, as compared to 0.8 mg/kg for the 5055 analog) and a shorter duration of action.

residue would reduce the affinity of the analog toward GalR1 subtype, while maintaining the high affinity toward GalR2 (see binding data for the Gal(2-11) analog in Table 21). The 1205-1 analog had reduced potency in the 6 Hz limbic seizure model (ED$_{50}$=5.7 mg/kg).

In summary, the SAR results show that a combination of cationization and lipidization is superior over individual chemical-modifications.

TABLE 22

| NAX | Structure | % Protection at 1, 2 and 4 hours afforded by a dose of 4 mg/kg, i.p. |
|---|---|---|
| 5055 | (Sar)WTLNSAGYLLGPKK(Lys-P)K (SEQ ID NO: 56) | 100%, 100%, 0% |
| 1205-5 | (Sar)WTLNSAGYLLKK(Lys-P)K (SEQ ID NO: 72) | 100%, 25%, 0% |
| 306-3 | (Sar)WTLNSAGYKK(Lys-P)K (SEQ ID NO: 66) | 75%, 25%, 0% |

Introduction of backbone spacers, such as 6-aminohexanoic acid, were also explored between the galanin fragment and the KKKpK motif might affect the anticonvulsant activity of the analogs. The analogs 306-2 and 306-4 maintained its anticonvulsant activity (ED$_{50}$=2.95 mg/kg for 306-4). Interestingly, the 306-4 analog appeared very active in the second response phase of the inflammatory pain assay in mice at the 2.95 mg/kg dose (ED$_{50}$ in the 6 Hz model), suggesting that the potency of its anticonvulsant and antinociceptive activity may not be directly correlated.

a) Design and Chemical Synthesis of Galanin Analogs that Penetrate the BBB

Based on the current SAR results, the synthesis and characterization of the analogs containing a combination of chemical modifications is carried out. A new strategy for cationization is employed: polyamine-based compounds, such as spermine, or lipo-polyamine conjugates are used. Since glycosylation of peptides is a well-established strategy to improve their BBB penetration, glycosylated galanin analogs are employed.

TABLE 23

| NAX | Structure | % Protection at 1, 2 and 4 hours afforded by a dose of 4 mg/kg, i.p. |
|---|---|---|
| 5055 | (Sar)WTLNSAGYLLGPKK(Lys-P)K (SEQ ID NO: 56) | 100%, 100%, 0% |
| 306-2 | (Sar)WTLNSAGYLLGP(Ahx)KK(Lys-P)K (SEQ ID NO: 65) | 100%, 75%, 0% |
| 306-4 | (Sar)WTLNSAGY(Ahx)KK(Lys-P)K (SEQ ID NO: 67) | 50%, 0%, 0% |

Lastly, the activity of the 5055 analog missing the N-terminal sarcosine residue was examined (analog 1205-1: WTLNSAGYLLGPKK(Lys-P)K). This analog was designed based on the galanin agonist analog Gal(2-11), also known as AR-M1896: the assumption was that the removal of the first Cationization.

Positively charged Lys residues and their combinations with Lys-palm can improve delivery of the analogs into the CNS. Examples of these relatively conservative analogs are shown in Table 24.

TABLE 24

Analogs with modifications of the KKKpK motif.
All analogs are amidated at the C-terminus.

| Analogs | Rationale |
| --- | --- |
| (Sar)WTLNSAGYLLGPKK(Lys-P)K (SEQ ID NO: 56) | NAX 5055 (shown as a reference) |
| (Sar)WTLNSAGYLLGP(Orn)(Orn)(Lys-P)(Orn) (SEQ ID NO: 73) | Replacing Lys with Ornithine (Orn) results in shorter side chains by one methylene group. This addresses a relative role of hydrophobicity in the BBB-penetration of NAX 5055. |
| (Sar)WTLNSAGYLLGP(Dab)(Dab)(Lys-P)(Dab) (SEQ ID NO: 74) | Replacing Lys with 2,4-diaminobutyric acid (Dab) results in shorter side chains by two methylene groups. See the rationale above. |
| (Sar)WTLNSAGYLLGP$_b$K$_b$K(Lys-P)$_b$K (SEQ ID NO: 75) | beta-homo-Lys is (1) metabolically stable and (2) more hydrophobic. |
| (Sar)WTLNSAGYLLGPHH(Lys-P)H (SEQ ID NO: 76) | Lys-to-His replacement decreases basicity of the analog |
| (Sar)WTLNSAGYLLGP(Lys-P)KKK (SEQ ID NO: 77) | Chaning relative positions of the Lys and Lys-palm residues |
| (Sar)WTLNSAGYLLGPK(Lys-P)KK (SEQ ID NO: 78) | As abc |
| (Sar)WTLNSAGYLLGPKKK(Lys-P) (SEQ ID NO: 79) | As above |

Since cationization is critical for the penetration of the galanin analogs through the BBB, galanin analogs containing polyamines are explored. The rationale behind exploring analogs containing spermine is to replace several Lys residues (present in the NAX 5055) with a single molecule carrying several amine groups, while lacking peptide bonds (reduced susceptibility for proteolysis and a lack of hydrogen-bonding donors/acceptors. Several galanin analogs are synthesized in which spermine is either a part of the backbone or a side chain. Table 25 summarizes structures and a rationale for the galanin-spermine analogs.

TABLE 25

NAX 5055 analogs containing spermine as a backbone spacer or as a side chain. SpermineS is 1,5,10,14-tetra-azaquatrodecan-N4-succinamic acid.
All analogs are amidated at the C-terminus.

| Analog | Rationale |
| --- | --- |
| (Sar)WTLNSAGY(SpermineS)(Lys-P) (SEQ ID NO: 80) | Spermine-N4succinamic acid has 18 backbone atoms, replacing in principle 6 AA. SpermineS plays a role as a backbone spacer replacing "LLGPKK." in NAX 5055. |
| (Sar)WTLNSAGYLLGPKK(Lys-P)-(SpermineS) (SEQ ID NO: 81) | Replacing of the Lys17 with spermine will increase basicity of the analog. |
| (Sar)WTLNSAGYLLGPKK(Glu-Spermine)K (SEQ ID NO: 82) | Replacing of the Lys-palm with spermine coupled to side chain of glutamic acid. |
| (Sar)WTLNSAGYLLGPKK(Lys-Spermine-Palmitoyl)K (SEQ ID NO: 83) | Replacing Lys-palm moiety with spermine-palmitoyl will increase basicity of the analog. |

Lipidization.

In the next set of analogs (Table 26), the effects of lipidization in the position 16 on the penetration of the analogs through the BBB are explored.

TABLE 26

Analogs with modifications of in position 16. All analogs are amidated at the C-terminus.

| Analogs | Rationale |
| --- | --- |
| (Sar)WTLNSAGYLLGPKK(TDA)K (SEQ ID NO: 84) | Testing effects of replacing the Lys-palmityoyl moiety with a shorter lipoamino acid: tetradecanoic moiety. |
| (Sar)WTLNSAGYLLGPKK(NorL)K (SEQ ID NO: 85) | Replacing the Lys-palmityoyl moiety with norleucine is a "truncated" analog missing palmitoyl residue (and amino group). |

Glycosylation.

Two glycosylated galanin analogs containing alpha-mannosyl or beta-melibiose serine residues in the position 16 are synthesized first. Thus, in these analogs, the saccharide moiety replaces the Lys-palm residue.

TABLE 27

Glycosylated galanin analogs. All analogs are amidated at the C-terminus.

| Analogs | Rationale |
| --- | --- |
| (Sar)WTLNSAGYLLGPKK(Lys-P)K (SEQ ID NO: 56) | NAX 5055 (shown as a reference) |
| (Sar)WTLNSAGYLLGPKK(Man)K (SEQ ID NO: 86) | Testing effects of replacing Lys-palmityoyl moiety with a monosaccharide derivative: L-Ser-alpha-Mannose. |
| (Sar)WTLNSAGYLLGPKK(Mel)K (SEQ ID NO: 87) | Testing effects of replacing Lys-palmityoyl moiety with a disaccharide derivative: L-Ser-beta-Melibiose. Rationale as above. |

Backbone Spacers.

Effects of backbone spacers on the anticonvulsant activity of the NAX-5055 based analogs are explored. Main advantages of replacing parts of the peptidic backbone with non-peptidic-based spacers are: (1) reducing molecular size that should improve the BBB-permeability, (2) reducing susceptibility of proteolytic degradation, and (3) a lack of hydrogen bond donors/acceptors. Examples of these analogs are shown in Table 28.

Chemical Synthesis of the Analogs.

All analogs are synthesized using Fmoc-based solid-phase peptide synthesis (SPPS) protocols and an automated peptide synthesizer. All building blocks for SPPS are commercially available, including Fmoc protected backbone spacers, glycoamino acids, spermine, spermine-succinamic acid or spermine-palimitoyl (Sussex Research Laboratories, Iris Biotech, NeoMPS, Chem-Impex). Coupling methods will be per-

TABLE 28

NAX 5055 analogs containing extended glycine backbone spacers. All analogs are amidated at the C-terminus.

| Analogs | Spacer |
| --- | --- |
| (Sar)WTLNSAGYLL(1PEG)KK(Lys-P)K (SEQ ID NO: 88) | 5-amino-3-oxapemtanoic acid |
| (Sar)WTLNSAGYLL(5AVA)KK(Lys-P)K (SEQ ID NO: 89) | 5-aminovaleric acid |
| (Sar)WTLNSAGYL(2PEG)KK(Lys-P)K (SEQ ID NO: 90) | 8-amino-3,6-dioxaoctanoic acid |
| (Sar)WTLNSAGYL(8AOA)KK(Lys-P)K (SEQ ID NO: 91) | 8-aminooctanoic acid |
| (Sar)WTLNSAGY(1PEG)(5AVA)KK(Lys-P)K (SEQ ID NO: 92) | 5-amino-3-oxapemtanoic acid, 5-aminovaleric acid | formed as described previously (Fields and Noble 1990; Albericio 2000). The For the analogs in which spermine or its derivatives are conjugated in the position 16, the analogs have incorporated glutamic acid protected with gamma-2-phenylisopropyl ester (0-2-PhiPr). The side chain carboxyl is deprotected on-resin using 1% TFA in dichloromethane. Coupling of spermine or its palmitoyl derivative (Fmoc/Boc protected on other amino groups) is carried out using 1,3-diisopropylcarbodiimide (DIC). The peptides are removed from solid support, washed and precipitated with MTBE. The analogs are purified using a diphenyl preparative reversed-phase HPLC. Linear gradient of acetonitrile (in 0.1% TFA) from 20% to 90% of 90% acetonitrile/10% water/0.1% TFA in 15 minutes is used for elution. Analogs are quantified using molar absorbance coefficient 7,000 at 280 nm (1 Tpr 5,600 and 1 Tyr 1,400). These procedures have been efficient for preparing NAX 5055 and similar analogs with individual batches ranging from 10 to 50 milligrams.

b) In Vitro Characterization of Galanin Analogs that Cross BBB

In order to characterize biological activity of the synthesized galanin analogs, binding constants for GalR1 and GalR2 receptors are determined. The three main objectives were: (1) to assess what effect chemical modifications introduced to GAL(1-16) change affinity toward galanin receptors, (2) to determine the selectivity profile for galanin analogs, and (3) to develop a reliable screening assay of high-affinity galanin analogs that penetrate the BBB. It has been shown that NAX 5055 retains low nanomolar affinity toward both GalR1 and GalR2.

A fluorescence-based binding assay with europium-labeled galanin (Delfia assay from Perkin Elmer) can be used. This assay, previously described by (Valenzano, Miller et al. 2000), is validated and used to characterize binding properties of all previously synthesized analogs. The main advantage of the fluorescence-based binding assay over more traditionally used radioligand binding assay is to avoid drawbacks of radioactivity (health, disposal, short shelf-life, long duration of acquiring signals), making such assays more friendly for medium- and high-throughput screening. Labeling receptor ligands with lanthanides offers an advantage of high sensitivity due to their long fluorescence lifetimes. Using time-resolved fluorescence detection with a delay of 400 microseconds, less that 1 femtomole of europium can be detected in a single well.

Two galanin receptors are acquired from Perkin Elmer or Multispan, Inc. in the form of membrane preparations. Europium-labeled galanin (Eu-Galanin) is purchased from Perkin Elmer. Binding reactions are carried out with 10 micrograms of membrane protein (concentrations) in a volume of 60 microliters of the binding buffer (EDTA, BSA, PEG in a hypotonic buffer). Saturation binding curves are generated with a range of Eu-galanin from 0.01 to 10 nM ligand concentration. For determining binding constants, 0.2 nM Eu-Galanin is incubated with membranes for 2 hours. The reactions is terminated by a rapid filtration through Acro Well filter plates using a vacuum box, and washed three times with 300 mL of hypotonic buffer. Enhancement solution is added to each well and the TRF signal is recorded on Victor3 spectrofluorimeter with TFR.

c) In Vivo Characterization of Galanin Analogs that Cross the BBB

The anticonvulsant activity of galanin-based neuropeptides in a pharmaco-resistant model of epilepsy and their antiepileptogenic properties.

Selected analogs in the 6 Hz limbic seizure model of pharmaco-resistant partial epilepsy are characterized. The potency of the analogs in this model of pharmaco-resistant epilepsy is determined by generating dose-response curves following i.p. administration. All compounds are administered i.p. or in. 0.9% NaCl in a volume of 0.01 ml/g body weight. In addition to the acute efficacy studies in the 6 Hz seizure test, the ability of NAX 5055 and other galanin analogs to prevent kindling acquisition in the mouse corneal kindling model of partial epilepsy is analyzed (Matagne and Klitgaard 1998).

Anticonvulsant Testing.

The ability of each analog to prevent seizures induced by 6 Hz corneal stimulation (3 sec duration) is assessed at three different stimulus intensities (i.e., 22, 32, and 44 mA). The 6 Hz seizure is characterized by a minimal clonic phase that is followed by stereotyped, automatistic behaviors described originally as being similar to the aura of human patients with partial seizures (Toman, Everett et al. 1952; Barton, Klein et al. 2001). Animals not displaying this behavior are considered protected. As mentioned above, the 6 Hz seizure becomes more resistant to block by antiepileptic drugs as the current is increased from 22 mA to 44 mA. Activity for each of the analogs in the 6 Hz seizure test is quantitated at the time to peak effect following i.p. according to the methods described by (Barton, Klein et al. 2001). For this test, a drop of anesthetic/electrolyte solution (0.5% tetracaine hydrochloride in 0.9% saline) is applied to the eyes of each animal prior to placement of the corneal electrodes. For the time to peak effect studies, a total of 20 CF-1 mice is employed. Groups of 4 mice are tested at various times (i.e., 0.25, 0.5, 1, 2, and 4 h). For the dose-response studies, groups of at least eight mice are tested with various doses of the candidate peptide until at least two points have been established between the limits of 100% efficacy and 0% efficacy. The dose of drug required to produce the median effective dose (i.e., $ED_{50}$) in 50% of the animals exposed, the 95% confidence interval, the slope of the regression line, and the S.E.M. of the slope is calculated by a computer program based on the method described by Finney (Finney 1971; Finney 1971).

Acquisition of Corneal Kindling.

NAX 5055 and a select number of other galanin analogs are evaluated for their ability to prevent the acquisition of kindling in the mouse corneal kindling model as described by (Matagne and Klitgaard 1998). Daily electrical stimulation via the cornea results in a stable kindled state within 15-20 days. This is an ideal model to initially assess the ability of selected galanin analogs to prevent kindling acquisition because the amount of peptide required is much lower than what is required for a rat kindling study. Those compounds found to be effective in preventing the acquisition of kindling are subsequently evaluated in a more traditional rat kindling model; i.e., amygdala kindled rat. For the proposed studies two groups of mice (n=8 mice per group) are randomized to receive either vehicle or peptide prior to each kindling stimulation. Each peptide is administered i.p. at a dose that approximates the $ED_{50}$ for prevention of 6 Hz (44 mA) seizures. At the time to peak effect (obtained from the 6 Hz study), they are stimulated via corneal electrodes with a subconvulsive current (50 Hz, 3 mA, for 3.0 sec) and observed for the presence or absence of seizure activity. Seizure activity is scored according to the criteria established by Racine et al., (1972). Animals receive two stimulations per day until they display their first Stage 5 behavioral seizure and then once daily until they display stable secondarily generalized seizures (5 consecutive Stage 4-5 seizures). Peptide treatment continues in the experimental group until the point that the control mice become fully kindled. At this point, mice in both groups are permitted a one-week stimulus and treatment-free week. On the 8$^{th}$ day, mice in both groups are stimulated in the absence of peptide or vehicle and their seizure score recorded.

Mice in the vehicle-treated group can reach a fully kindled state by the end of the second full week of stimulation (FIGS. 32 and 33). Furthermore, given that i.c.v. galanin has been previously found to prevent the development of kindling (Mazarati, Lundstrom et al. 2006), mice in the experimental group do not kindle or kindle at a rate slower than vehicle-treated mice. Therefore, the seizure score on the last day of the active kindling study can be at 1 or less and the seizure score would remain low following the wash-out period; e.g., treated (antiepileptogenic). If the post-washout period seizure score of the experimental group is not significantly different from the vehicle-treated group, it can be concluded that the effect of the peptide during the active treatment period was due to its anticonvulsant effect; e.g., treated (anticonvulsant). When an antiepileptogenic effect is observed, all mice in both the vehicle- and treated-groups are kindled in the absence of drug to see whether the previously treated mice kindle in the absence of peptide.

5. Example 5

Design and Chemical Synthesis of Analogs a) Neuropeptide Analogs that Penetrate the BBB

Table 29 summarizes structures of several neuropeptide analogs. For each of the analogs, the "KKK$_p$K" motif is attached to either N- or C-terminus during the solid-phase peptide synthesis. Below, provided is a brief rationale for designing analogs of each neuropeptide.

TABLE 29

Structures of selected neuropeptides.

| Neuropeptide | Structure |
|---|---|
| SOM | Ala-Gly-Cys-Lys-Asn-Phe-Phe-Trp-Lys-Thr-Phe-Thr-Ser-Cys (SEQ ID NO: 30) |
| Octreotide-NH2 | $_D$Phe-Cys-Phe-$_D$Trp-Lys-Thr-Cys-Thr-NH$_2$ (SEQ ID NO: 101) |
| DSIP | Trp-Ala-Gly-Gly-Asp-Phe-Ser-Gly-Glu (SEQ ID NO: 102) |
| Dynorphin A(1-16) | Tyr-Gly-Gly-Phe-Leu-Arg-Arg-Ile-Arg-Pro-Lys-Leu-Lys-Trp-Asp-Asn-Gln (SEQ ID NO: 103) |
| NPY(13-36) | PAEDLARYYSALRAYINLITRQRY-NH$_2$ (SEQ ID NO: 104) |

Somatostatin and its subtype-selective analog, octreotide, can "accommodate" the N-terminal extensions without compromising their bioactivity (Dasgupta and Mukherjee 2000; Dasgupta, Singh et al. 2002; Na, Murty et al. 2003). N-terminal acetylation of the RC-160 analog resulted in an increase of the CNS concentrations of this somatostatin analog (Banks, Schally et al. 1990). Octreotide can also penetrate the BBB to some extent without additional modifications (Fricker, Nobmann et al. 2002).

DSIP.

It has been shown that the N-terminal extensions did not affect antiepileptic activity of DSIP, whereas the C-terminal extensions resulted in inactive analogs. Thus, DSIP analogs can be created with vectors attached to the N-terminus.

The "KKK$_2$K" motif is introduced to the N-terminus of SOM, octreotide or DSIP. Attaching the "KKK$_p$K" motif using three distinct spacers (Gly, 6-aminohexanoix acid (Ahx), Ahx-Gly) minimizes the possibility that the bulky Lys-palm residue can affect interactions with a target receptor. The following analogs are synthesized:

```
                                        (SEQ ID NO: 105)
KK(K_p)K-(neuropeptide)

(SEQ ID NO: 106)
KK(K_p)KG-(neuropeptide)

(SEQ ID NO: 107)
KK(K_p)K(Ahx)-(neuropeptide)

(SEQ ID NO: 108)
KK(K_p)K(Ahx)G-(neuropeptide)
```

Dynorphin A(1-16) can be truncated or modified at the C-terminus, without significant reduction of the affinity toward opioid receptors (Lapalu, Moisand et al. 1997; Naqvi, Haq et al. 1998; Schlechtingen, DeHavert et al. 2003). Thus, similar to galanin analogs that penetrate the BBB, dynorphin A (1-16) analogs are synthesized in which the last several residues are replaced by the "KKK$_p$K" motif. The following analogs are shown:

```
                                        (SEQ ID NO: 109)
Tyr-Gly-Gly-Phe-Leu-Arg-Arg-Ile-Arg-Pro-Lys-Leu-
Lys-Lys-(Lys-palm)-Lys-NH_2

(SEQ ID NO: 110)
Tyr-Gly-Gly-Phe-Leu-Arg-Arg-Ile-Arg-Pro-Lys-Leu-
Lys-Lys-Lys-(Lys-palm)-Lys-NH_2

(SEQ ID NO: 111)
Tyr-Gly-Gly-Phe-Leu-Arg-Arg-Ile-Arg-Pro-Lys-Lys-
Lys-(Lys-palm)-Lys-NH_2

(SEQ ID NO: 112)
Tyr-Gly-Gly-Phe-Leu-Arg-Arg-Ile-Arg-Pro-Lys-Leu-
Lys-(Ahx)-Lys-Lys-(Lys-palm)-Lys-NH_2
```

Neuropeptide Y analogs are designed based on data from numerous sAR studies carried out in the laboratory of Prof.

Annette G. Beck-Sickinger (comprehensive reviews (Beck-Sickinger and Jung 1995; Cabrele and Beck-Sickinger 2000)). Specifically, the design is based on $^{99m}$Tc-labeled NPY analogs that were synthesized and tested as tumor imaging agents (Langer, La Bella et al. 2001). The truncated NPY analog (Ac-[Ahx5-24,K4(99 mTc(CO)3-PADA),A26]-NPY, containing bulky 2-picolylamine-N,N-diacetic acid with chelated $^{99m}$Tc was very potent against Y2 receptor subtype ($IC_{50}$=1 nM). Thus, 2-picolylamine-N,N-diacetic acid can be replaced with Lys-palmitoyl residue. The following two NPY analogs are shown:

```
                                       (SEQ ID NO: 113)
KKK(K_p)(Ahx)RAYINLITRQRY-NH_2

(SEQ ID NO: 114)
KK(K_p)K(Ahx)RAYINLITRQRY-NH_2
```

Four analogs of NPY(13-36) are also produced with the N-terminal extensions:

```
                                       (SEQ ID NO: 115)
KK(K_p)K-[NPY(13-16)]

(SEQ ID NO: 116)
KK(K_p)KG-[NPY(13-36)]

(SEQ ID NO: 117)
KK(K_p)K(Ahx)-[NPY(13-36)]

(SEQ ID NO: 118)
KK(K_p)K(Ahx)G-[NPY(13-36)]
```

All analogs are synthesized using standard Fmoc-based solid-phase peptide synthesis (SPPS) protocols and an automated peptide synthesizer. All building blocks for SPPS are commercially available, including Fmoc protected aminohexanoic acid, Lys-palmitoyl, and glycoamino acids (Sussex Research Laboratories, Iris Biotech, NeoMPS, Chem-Impex). Coupling methods are performed as described previously (Fields and Noble 1990; Albericio 2000). The peptides are removed from solid support with reagents and then precipitated with MTBE. The analogs are purified using a diphenyl preparative reversed-phase HPLC. Linear gradient are used for elution. Initial and final concentrations of 90% acetonitrile/10% water/0.1% TFA is determined for each analog based on their retention times from analytical HPLC analysis. Analogs are quantified using molar absorbance coefficient calculated for each analog at 280 nm (Trp $\epsilon$=5,600 and Tyr $\epsilon$=1,400). These procedures have been efficient for preparing galanin analogs in quantities ranging from 10 to 50 milligrams. For oxidation of the disulfide bridge in somatostatin or octreotide analogs, Clear-Ox resin is used (Darlak, Weigandt Long et al. 2004; Green and Bulaj 2006). Oxetreotide analogs described herein were oxidized with yields exceeding 95%. Final oxidation products are purified by preparative HPLC.

Anticonculsant Activity of Neuropeptide Analogs.

Analogs in the 6 Hz limbic seizure model of pharmacoresistant partial epilepsy are characterized. The activity of the analogs following i.c.v. and i.p. administration can be determined. The strategy is to test the analogs i.c.v. (2 nmoles) first: active analogs are further tested using i.p. bolus injections (4 mg/kg). Anticonvulsant activity of dynorphin A(1-16), NPY and NPY(13-36) is also tested at 2 nmoles, following i.c.v. administration. These results serve as a reference for screening their modified analogs.

Anticonvulsant Testing.

The ability of each analog to prevent seizures induced by 6 Hz corneal stimulation (3 sec duration) is assessed at 32 mA stimulus intensity. The 6 Hz seizure is characterized by a minimal clonic phase that is followed by stereotyped, automatistic behaviors described originally as being similar to the aura of human patients with partial seizures (Toman, Everett et al. 1952; Barton, Klein et al. 2001). Animals not displaying this behavior are considered protected. Activity for each of the analogs in the 6 Hz seizure test are quantitated at the time to peak effect following i.c.v or i.p. according to the methods described by (Barton, Klein et al. 2001). For this test, a drop of anesthetic/electrolyte solution (0.5% tetracaine hydrochloride in 0.9% saline) is applied to the eyes of each animal prior to placement of the corneal electrodes. For the time to peak effect studies, a total of 20 CF-1 mice are employed. Groups of 4 mice are tested at various times (i.e., 0.25, 0.5, 1, 2, and 4 h). All compounds are administered in 0.9% NaCl in a volume of 0.01 ml/g body weight.

Design and Chemical Synthesis of Glycosylated Neuropeptide Analogs.

Glycosylation appeared very effective in improving penetration of opioid peptides through the BBB (Elmagbari, Egleton et al. 2004; Polt, Dhanasekaran et al. 2005). FIG. 34 shows structures of sugar residues that were used for enkephalin analogs. Introduction of β-melibiose into the peptide produced analog with the best analgesic potency following i.v. administration.

β-melibiose-Ser residue can be introduced into selected neuropeptide analogs in place of either the full-length "KKKpK" motif or Lys-palmitoyl residue (as described above). For chemical synthesis of the glycosylated analogs, an Fmoc-protected peracetyl-β-melibiose-Ser derivative available from Sussex Research is used. The standard solid-phase synthesis protocol is applied. Deacetylation of melibiose residue is accomplished by pH-controlled (pH 10) incubation of analogs in 10 mM sodium methoxide in methanol for 4-5 hours. The analogs are purified by preparative HPLC and dried in a speedvac prior to testing their anticonvulsant activity.

6. Example 6

Effects of NAX5055 on Mouse Corneal Kindling Acquisition

The ability of the blood-brain-barrier penetrant galanin-based neuropeptide NAX-5055 to prevent the development of corneal kindling was studied in CF#1 mice. The mouse corneal kindling model is a non-intrusive animal model of partial epilepsy wherein mice receive an initially subconvulsive current (3 mA) for 3 seconds via corneal electrodes twice daily for several days. Vehicle treated mice usually require between 12-16 days to reach a stable Stage 5 seizure; i.e., a secondary generalized focal seizure. In the present study, 16 mice were randomized to one of two experimental groups; saline or NAX-5055. Mice in the NAX-5055 group received an intraperitoneal (i.p.) injection of NAX-5055 (4 mg/kg, n=8) 12 hours and 1 hour prior to their first corneal stimulation and 1 hour prior to each subsequent stimulation. In contrast, mice in the vehicle group received 0.9% NaCl (n=8) one hour prior each corneal stimulation. Prior to each stimulation a drop of 0.5% tetracaine in 0.9% saline was applied to the cornea. Following stimulation seizure activity was scored on a scale of 0-5 as established by Racine (1972). Treatment was continued until control animals consistently displayed stage 5 seizures.

As shown in FIGS. 32 and 33, mice in the NAX-5055 group segregated into two separate populations; i.e., those that were sensitive (n=3) and those that were insensitive to NAX-5055

(n=5) treatment. Sensitivity was defined as those mice that failed to display a Stage 5 seizure during the period of stimulation. NAX-5055 sensitive animals required a significantly greater number of stimulations to reach stage 1, 2 and 3 compared to both controls and NAX-5055 insensitive animals. Furthermore, upon re-challenge after a one-week stimulation and peptide free period, NAX-5055 sensitive animals required significantly more stimulations to reach stage 4/5 seizures compared to controls and NAX-5055 insensitive animals. These results show that NAX-5055 can delay kindling acquisition and thus may be useful for the early treatment of patients at risk for the development of epilepsy following a given brain insult. (Racine R J. Modification of seizure activity by electrical stimulation. II. Motor seizure. Electroencephalogr Clin Neurophysiol. 1972 March; 32(3): 281-94.)

Table 30 shows anticonvulsant activity of octreotide or DSIP analogs following systemic delivery.

| Analogs | % Protection at 30 min (4 mg/kg, i.p.) |
|---|---|
| Octreotide analogs | |
| $_D$Phe-Cys-Phe-$_D$Trp-Lys-Thr-Cys-Thr-NH$_2$ | 50% |
| Lys-Lys-Lys(palm)-Lys-Ahx-$_D$Phe-Cys-Phe-$_D$Trp-Lys-Thr-Cys-Thr-NH$_2$ | 100% |
| DSIP analogs | |
| Trp-Ala-Gly-Gly-Asp-Phe-Ser-Gly-Glu | 0% |
| Ahx-Gly-Gly-Trp-Ala-Gly-Gly-Asp-Phe-Ser-Gly-Glu | 50% (100% after 2 hours) |

Table 31 shows additional Delta Sleep Inducing Peptides:

| Analog | Structure |
|---|---|
| DSIP-BBB8 | (Ahx)GGWAGGDASGE (SEQ ID NO: 136) |
| DSIP-BBB99 | (Palm)GGWAGGDASGE (SEQ ID NO: 137) |
| DSIP-BBB100 | ($K_p$)GGWAGGDASGE (SEQ ID NO: 138) |
| DSIP-BBB101 | KKK($K_p$)GGWAGGDASGE (SEQ ID NO: 139) |
| DSIP-BBB102 | KK($K_p$)KGGWAGGDASGE (SEQ ID NO: 140) |
| DSIP-BBB103 | KKKGGWAGGDASGE (SEQ ID NO: 141) |
| DSIP-BBB104 | (DK)(DK)(DK)(Kp)GGWAGGDASGE (SEQ ID NO: 58) |

The invention claimed is:

1. A method of increasing permeability of the blood brain barrier for a neuropeptide comprising modifying the neuropeptide, the neuropeptide being derived from an unmodified neuropeptide selected from galanin, somatostatin, delta-sleep inducing peptide, and neuropeptide Y, comprising:
generating a first modification relative to the unmodified neuropeptide that increases the lipophilic character of the modified neuropeptide when compared to the unmodified neuropeptide; with the first modification being selected from at least one of:
(a) a hydrophobic moiety conjugated to one or more amino acid residues of the modified neuropeptide; and
(b) substitution of one or more aromatic amino acid residues with a halogenated aromatic amino acid residue; and
generating a second modification relative to the unmodified neuropeptide that increases the basicity of the modified neuropeptide when compared to the unmodified neuropeptide, with the second modification being selected from at least one of:
(a) an oligomer of positively charged amino acid residues introduced into the amino acid sequence of the unmodified neuropeptide, wherein the oligomer is selected from the group consisting of homooligomers and heterooligomers comprising Lysine, Arginine, homo-Lysine, homo-Arginine, L-Ornithine, D-Ornithine, 2,3-Diaminopropioic acid, and 2,4-Diaminobutyric acid, and
(b) a polyamine-based moiety conjugated to the modified neuropeptide, wherein the polyamine-based moiety is selected from the group consisting of spermine, spermidine, polyamidoamine, dendrimers, and polyamine toxins.

2. The method of claim 1, wherein the hydrophobic moiety is one or more polyaliphatic chains.

3. The method of claim 1, wherein the first modification is (b) substitution of one or more aromatic amino acid residues with a halogenated aromatic amino acid residue.

4. The method of claim 1 wherein the second modification is (a) an oligomer of positively charged amino acid residues introduced into the amino acid sequence of the unmodified neuropeptide, wherein the oligomer is selected from the group consisting of homooligomers and heterooligomers comprising Lysine, Arginine, homo-Lysine, homo-Arginine, L-Ornithine, D-Ornithine, 2,3-Diaminopropioic acid, and 2,4-Diaminobutyric acid.

5. The method of claim 1, wherein the second modification is (b) a polyamine-based moiety conjugated to the modified neuropeptide, wherein the polyamine-based moiety is selected from the group consisting of spermine, spermidine, polyamidoamine, dendrimers and polyamine toxins.

6. The method of claim 1, wherein the modified neuropeptide can cross the blood-brain barrier with 1%, 5%, 10%, 20%, 30%, 40%, 50%, 60%, 70%, 80%, 90%, or 100% more efficiency compared to the unmodified neuropeptide.

7. The method of claim 1, further comprising increasing glycosylation of the neuropeptide compared to the unmodified form of the neuropeptide.

* * * * *

SEQUENCE LISTING

```
<160> NUMBER OF SEQ ID NOS: 142

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 1

Gly Trp Thr Leu Asn Ser Ala Gly Tyr Leu Leu Gly Pro His Ala Val
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 15
<223> OTHER INFORMATION: Xaa = Lys-palm
<220> FEATURE:
<221> NAME/KEY: MOD_RES
<222> LOCATION: 16
<223> OTHER INFORMATION: Xaa = tert-Leucine
```

```
<220> FEATURE:
<221> NAME/KEY: MOD_RES
<222> LOCATION: 16
<223> OTHER INFORMATION: Amidation at the C-terminus

<400> SEQUENCE: 2

Xaa Trp Thr Leu Asn Ser Ala Gly Tyr Leu Leu Gly Pro His Xaa Xaa
 1               5                  10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
<221> NAME/KEY: MOD_RES
<222> LOCATION: 17
<223> OTHER INFORMATION: Amidation at the C-terminus

<400> SEQUENCE: 3

Xaa Trp Thr Leu Asn Ser Ala Gly Tyr Leu Leu Gly Pro Lys Lys Xaa
 1               5                  10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 4

Xaa Trp Thr Leu Asn Ser Ala Gly Tyr Leu Leu Gly Pro Lys Lys Xaa
 1               5                  10                  15

Lys

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 15
<223> OTHER INFORMATION: Xaa = Lys-palm
```

```
<400> SEQUENCE: 5

Xaa Trp Thr Leu Asn Ser Ala Gly Tyr Leu Leu Gly Lys Lys Xaa Lys
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm

<400> SEQUENCE: 6

Xaa Trp Thr Leu Asn Ser Ala Gly Tyr Leu Leu Lys Lys Xaa Lys
 1               5                  10                  15

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 13
<223> OTHER INFORMATION: Xaa = Lys-palm

<400> SEQUENCE: 7

Xaa Trp Thr Leu Asn Ser Ala Gly Tyr Leu Lys Lys Xaa Lys
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 12
<223> OTHER INFORMATION: Xaa = Lys-palm

<400> SEQUENCE: 8

Xaa Trp Thr Leu Asn Ser Ala Gly Tyr Lys Lys Xaa Lys
 1               5                  10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
```

-continued

```
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 9

Xaa Trp Thr Leu Asn Ser Ala Gly Tyr Leu Leu Gly Pro Lys Lys Xaa
 1               5                  10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (3)...(4)
<223> OTHER INFORMATION: Xaa = represents spacer between residue 2 and
      residue 5
<220> FEATURE:
<221> NAME/KEY: MOD_RES
<222> LOCATION: 16
<223> OTHER INFORMATION: Xaa = Lys-palm

<400> SEQUENCE: 10

Xaa Trp Xaa Xaa Asn Ser Ala Gly Tyr Leu Leu Gly Pro Lys Lys Xaa
 1               5                  10                  15

Lys

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (6)...(7)
<223> OTHER INFORMATION: Xaa = represents spacer between residue 5 and
      residue 8
<220> FEATURE:
<221> NAME/KEY: MOD_RES
<222> LOCATION: 16
<223> OTHER INFORMATION: Xaa = Lys-palm

<400> SEQUENCE: 11

Xaa Trp Thr Leu Asn Xaa Xaa Gly Tyr Leu Leu Gly Pro Lys Lys Xaa
 1               5                  10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence = Synthetic
```

```
                Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (7)...(8)
<223> OTHER INFORMATION: Xaa = represents spacer between residue 6 and
      residue 9
<220> FEATURE:
<221> NAME/KEY: MOD_RES
<222> LOCATION: 16
<223> OTHER INFORMATION: Xaa = Lys-palm

<400> SEQUENCE: 12

Xaa Trp Thr Leu Asn Ser Xaa Xaa Tyr Leu Leu Gly Pro Lys Lys Xaa
 1               5                  10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (10)...(11)
<223> OTHER INFORMATION: Xaa = represents spacer between residue 9 and
      residue 12
<220> FEATURE:
<221> NAME/KEY: MOD_RES
<222> LOCATION: 16
<223> OTHER INFORMATION: Xaa = Lys-palm

<400> SEQUENCE: 13

Xaa Trp Thr Leu Asn Ser Ala Gly Tyr Xaa Xaa Gly Pro Lys Lys Xaa
 1               5                  10                  15

Lys

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (11)...(12)
<223> OTHER INFORMATION: Xaa = represents spacer between residue 10 and
      residue 13
<220> FEATURE:
<221> NAME/KEY: MOD_RES
<222> LOCATION: 16
<223> OTHER INFORMATION: Xaa = Lys-palm

<400> SEQUENCE: 14

Xaa Trp Thr Leu Asn Ser Ala Gly Tyr Leu Xaa Xaa Pro Lys Lys Xaa
 1               5                  10                  15

Lys
```

```
<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (12)...(13)
<223> OTHER INFORMATION: Xaa = represents spacer between residue 11 and
      residue 14
<220> FEATURE:
<221> NAME/KEY: MOD_RES
<222> LOCATION: 16
<223> OTHER INFORMATION: Xaa = Lys-palm

<400> SEQUENCE: 15

Xaa Trp Thr Leu Asn Ser Ala Gly Tyr Leu Leu Xaa Xaa Lys Lys Xaa
 1               5                  10                  15

Lys

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (6)...(8)
<223> OTHER INFORMATION: Xaa = represents spacer between residue 5 and
      residue 9
<220> FEATURE:
<221> NAME/KEY: MOD_RES
<222> LOCATION: 16
<223> OTHER INFORMATION: Xaa = Lys-palm

<400> SEQUENCE: 16

Xaa Trp Thr Leu Asn Xaa Xaa Xaa Tyr Leu Leu Gly Pro Lys Lys Xaa
 1               5                  10                  15

Lys

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: (3)...(4)
<223> OTHER INFORMATION: Xaa = represents spacer between residue 2 and
      residue 5
<220> FEATURE:
<221> NAME/KEY: MOD_RES
<222> LOCATION: (6)...(8)
```

```
<223> OTHER INFORMATION: Xaa = represents spacer between residue 5 and
      residue 9
<220> FEATURE:
<221> NAME/KEY: MOD_RES
<222> LOCATION: 16
<223> OTHER INFORMATION: Xaa = Lys-palm

<400> SEQUENCE: 17

Xaa Trp Xaa Xaa Asn Xaa Xaa Xaa Tyr Leu Leu Gly Pro Lys Lys Xaa
 1               5                   10                  15

Lys

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 18

Xaa Trp Thr Leu Asn Ser Ala Gly Tyr Leu Leu Gly Pro Lys Lys Xaa
 1               5                   10                  15

Lys

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 19

Xaa Trp Thr Leu Asn Ser Ala Gly Tyr Leu Leu Gly Lys Lys Lys Xaa
 1               5                   10                  15

Lys

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
```

```
<400> SEQUENCE: 20

Xaa Trp Thr Leu Asn Ser Ala Gly Tyr Leu Leu Lys Lys Lys Lys Xaa
 1               5                  10                  15
Lys

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly

<400> SEQUENCE: 21

Xaa Trp Thr Leu Asn Ser Ala Gly Tyr Leu Leu Gly Pro Lys Lys Lys
 1               5                  10                  15
Lys

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 15
<223> OTHER INFORMATION: Xaa = Lys-palm

<400> SEQUENCE: 22

Xaa Trp Thr Leu Asn Ser Ala Gly Tyr Leu Leu Gly Pro Lys Xaa Lys
 1               5                  10                  15
Lys

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm

<400> SEQUENCE: 23

Xaa Trp Thr Leu Asn Ser Ala Gly Tyr Leu Leu Gly Pro Xaa Lys Lys
 1               5                  10                  15
Lys

<210> SEQ ID NO 24
<211> LENGTH: 17
<212> TYPE: PRT
```

```
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14, 15, 17
<223> OTHER INFORMATION: Xaa = D-Lys
<220> FEATURE:
<221> NAME/KEY: MOD_RES
<222> LOCATION: 16
<223> OTHER INFORMATION: Xaa = Lys-palm

<400> SEQUENCE: 24

Xaa Trp Thr Leu Asn Ser Ala Gly Tyr Leu Leu Gly Pro Xaa Xaa Xaa
 1               5                  10                  15

Xaa

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14, 15, 17
<223> OTHER INFORMATION: Xaa = homo-Lys
<220> FEATURE:
<221> NAME/KEY: MOD_RES
<222> LOCATION: 16
<223> OTHER INFORMATION: Xaa = Lys-palm

<400> SEQUENCE: 25

Xaa Trp Thr Leu Asn Ser Ala Gly Tyr Leu Leu Gly Pro Xaa Xaa Xaa
 1               5                  10                  15

Xaa

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14, 15, 17
<223> OTHER INFORMATION: Xaa = Dbu
<220> FEATURE:
<221> NAME/KEY: MOD_RES
<222> LOCATION: 16
<223> OTHER INFORMATION: Xaa = Lys-palm

<400> SEQUENCE: 26

Xaa Trp Thr Leu Asn Ser Ala Gly Tyr Leu Leu Gly Pro Xaa Xaa Xaa
 1               5                  10                  15

Xaa
```

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = 2-amino-tetradecanoic acid

<400> SEQUENCE: 27

Xaa Trp Thr Leu Asn Ser Ala Gly Tyr Leu Leu Gly Pro Lys Lys Xaa
 1               5                  10                  15

Lys

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = 3,3-diphenylalanine

<400> SEQUENCE: 28

Xaa Trp Thr Leu Asn Ser Ala Gly Tyr Leu Leu Gly Pro Lys Lys Xaa
 1               5                  10                  15

Lys

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
<221> NAME/KEY: MOD_RES
<222> LOCATION: 18
<223> OTHER INFORMATION: Xaa = 12-amino-dodecanoic acid or 2-amino-
      tetradecanoic acid

<400> SEQUENCE: 29

Xaa Trp Thr Leu Asn Ser Ala Gly Tyr Leu Leu Gly Pro Lys Lys Xaa
 1               5                  10                  15

Lys Xaa

```
<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 30

Ala Gly Cys Lys Asn Phe Phe Trp Lys Thr Phe Thr Ser Cys
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 5
<223> OTHER INFORMATION: Xaa = Dbu
<220> FEATURE:
<221> NAME/KEY: VARIANT
<222> LOCATION: 8
<223> OTHER INFORMATION: Xaa = D-Trp
<220> FEATURE:
<221> NAME/KEY: MOD_RES
<222> LOCATION: 10, 12, 13
<223> OTHER INFORMATION: Xaa = Dpr

<400> SEQUENCE: 31

Ala Ala Cys Lys Xaa Phe Phe Xaa Lys Xaa Phe Xaa Xaa Cys
 1               5                  10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 4, 5
<223> OTHER INFORMATION: Xaa = Lys-palm
<220> FEATURE:
<221> NAME/KEY: VARIANT
<222> LOCATION: 8
<223> OTHER INFORMATION: Xaa = D-Trp

<400> SEQUENCE: 32

Ala Gly Cys Xaa Xaa Phe Phe Xaa Lys Thr Phe Thr Ser Cys
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 6, 7, 11
<223> OTHER INFORMATION: Xaa = Chloro-Phe
<220> FEATURE:
<221> NAME/KEY: VARIANT
<222> LOCATION: 8
<223> OTHER INFORMATION: Xaa = D-Trp

<400> SEQUENCE: 33
```

```
Ala Gly Cys Lys Asn Xaa Xaa Xaa Lys Thr Xaa Thr Ser Cys
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 5
<223> OTHER INFORMATION: Xaa = Dbu
<220> FEATURE:
<221> NAME/KEY: MOD_RES
<222> LOCATION: 10, 12, 13
<223> OTHER INFORMATION: Xaa = Dpr

<400> SEQUENCE: 34

```
Ala Ala Cys Lys Xaa Phe Phe Trp Lys Xaa Phe Xaa Xaa Cys
1               5                   10
```

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 4, 5
<223> OTHER INFORMATION: Xaa = Lys-palm

<400> SEQUENCE: 35

```
Ala Gly Cys Xaa Xaa Phe Phe Trp Lys Thr Phe Thr Ser Cys
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 6, 7, 11
<223> OTHER INFORMATION: Xaa = Chloro-Phe

<400> SEQUENCE: 36

```
Ala Gly Cys Lys Asn Xaa Xaa Trp Lys Thr Xaa Thr Ser Cys
1               5                   10
```

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 13, 14, 15
<223> OTHER INFORMATION: Xaa = Chloro-Phe

```
<400> SEQUENCE: 37

Xaa Trp Thr Leu Asn Ser Ala Gly Tyr Leu Leu Gly Xaa Xaa Xaa Val
 1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 3, 6, 7, 15
<223> OTHER INFORMATION: Xaa = Dpr
<220> FEATURE:
<221> NAME/KEY: MOD_RES
<222> LOCATION: 13, 16
<223> OTHER INFORMATION: Xaa = Dbu

<400> SEQUENCE: 38

Xaa Trp Xaa Leu Asn Xaa Xaa Gly Tyr Leu Leu Gly Xaa His Xaa Xaa
 1               5                  10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 9
<223> OTHER INFORMATION: Xaa = Chloro-Phe

<400> SEQUENCE: 39

Xaa Trp Thr Leu Asn Ser Ala Gly Xaa Leu Leu Gly Pro His Ala Val
 1               5                  10                  15

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: VARIANT
<222> LOCATION: 1
<223> OTHER INFORMATION: Xaa = D-Phe
<220> FEATURE:
<221> NAME/KEY: VARIANT
<222> LOCATION: 4
<223> OTHER INFORMATION: Xaa = D-Trp
<220> FEATURE:
<221> NAME/KEY: VARIANT
<222> LOCATION: 8
<223> OTHER INFORMATION: Xaa = Threoninol

<400> SEQUENCE: 40

Xaa Cys Phe Xaa Lys Thr Cys Xaa
 1               5
```

```
<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = N,N-bis(3aminopropyl) glycine
<220> FEATURE:
<221> NAME/KEY: MOD_RES
<222> LOCATION: 2
<223> OTHER INFORMATION: Xaa = aminohexanoic acid

<400> SEQUENCE: 41

Xaa Xaa Ala Gly Cys Lys Asn Phe Phe Trp Lys Thr Phe Thr Ser Cys
 1               5                  10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = N,N-bis(3aminopropyl) glycine
<220> FEATURE:
<221> NAME/KEY: MOD_RES
<222> LOCATION: 2
<223> OTHER INFORMATION: Xaa = aminohexanoic acid
<220> FEATURE:
<221> NAME/KEY: VARIANT
<222> LOCATION: 10
<223> OTHER INFORMATION: Xaa = D-Trp
<220> FEATURE:
<221> NAME/KEY: MOD_RES
<222> LOCATION: 13
<223> OTHER INFORMATION: Xaa = Chloro-Phe
<220> FEATURE:
<221> NAME/KEY: MOD_RES
<222> LOCATION: 15
<223> OTHER INFORMATION: Xaa = Dpr

<400> SEQUENCE: 42

Xaa Xaa Ala Gly Cys Lys Asn Phe Phe Xaa Lys Thr Xaa Thr Xaa Cys
 1               5                  10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 2
<223> OTHER INFORMATION: Xaa = aminohexanoic acid
<220> FEATURE:
<221> NAME/KEY: VARIANT
<222> LOCATION: 10
<223> OTHER INFORMATION: Xaa = D-Trp
<220> FEATURE:
<221> NAME/KEY: MOD_RES
<222> LOCATION: 13
<223> OTHER INFORMATION: Xaa = Chloro-Phe
<220> FEATURE:
<221> NAME/KEY: MOD_RES
<222> LOCATION: 14, 15
```

```
<223> OTHER INFORMATION: Xaa = Dpr

<400> SEQUENCE: 43

Trp Xaa Lys Lys Cys Lys Asn Phe Phe Xaa Lys Thr Xaa Xaa Xaa Cys
 1               5                   10                  15

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = aminohexanoic acid
<220> FEATURE:
<221> NAME/KEY: VARIANT
<222> LOCATION: 6
<223> OTHER INFORMATION: Xaa = D-Phe
<220> FEATURE:
<221> NAME/KEY: VARIANT
<222> LOCATION: 9
<223> OTHER INFORMATION: Xaa = D-Trp
<220> FEATURE:
<221> NAME/KEY: MOD_RES
<222> LOCATION: 13
<223> OTHER INFORMATION: Xaa = Threoninol

<400> SEQUENCE: 44

Lys Lys Xaa Lys Xaa Xaa Cys Phe Xaa Lys Thr Cys Xaa
 1               5                   10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 4
<223> OTHER INFORMATION: Xaa = Lys-palm
<220> FEATURE:
<221> NAME/KEY: MOD_RES
<222> LOCATION: 6, 7
<223> OTHER INFORMATION: Xaa = aminohexanoic acid
<220> FEATURE:
<221> NAME/KEY: VARIANT
<222> LOCATION: 8
<223> OTHER INFORMATION: Xaa = D-Phe
<220> FEATURE:
<221> NAME/KEY: VARIANT
<222> LOCATION: 11
<223> OTHER INFORMATION: Xaa = D-Trp
<220> FEATURE:
<221> NAME/KEY: MOD_RES
<222> LOCATION: 15
<223> OTHER INFORMATION: Xaa = Threoninol

<400> SEQUENCE: 45

Lys Lys Lys Xaa Lys Xaa Xaa Xaa Cys Phe Xaa Lys Thr Cys Xaa
 1               5                   10                  15

<210> SEQ ID NO 46
<211> LENGTH: 14
<212> TYPE: PRT
```

```
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1, 4
<223> OTHER INFORMATION: Xaa = Lys-palm
<220> FEATURE:
<221> NAME/KEY: MOD_RES
<222> LOCATION: 6
<223> OTHER INFORMATION: Xaa = aminohexanoic acid
<220> FEATURE:
<221> NAME/KEY: VARIANT
<222> LOCATION: 7
<223> OTHER INFORMATION: Xaa = D-Phe
<220> FEATURE:
<221> NAME/KEY: VARIANT
<222> LOCATION: 10
<223> OTHER INFORMATION: Xaa = D-Trp
<220> FEATURE:
<221> NAME/KEY: MOD_RES
<222> LOCATION: 14
<223> OTHER INFORMATION: Xaa = Threoninol

<400> SEQUENCE: 46

Xaa Lys Lys Xaa Lys Xaa Xaa Cys Phe Xaa Lys Thr Cys Xaa
 1               5                  10

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3, 8
<223> OTHER INFORMATION: Xaa = Lys-palm
<220> FEATURE:
<221> NAME/KEY: MOD_RES
<222> LOCATION: 5, 10
<223> OTHER INFORMATION: Xaa = aminohexanoic acid
<220> FEATURE:
<221> NAME/KEY: VARIANT
<222> LOCATION: 11
<223> OTHER INFORMATION: Xaa = D-Phe
<220> FEATURE:
<221> NAME/KEY: VARIANT
<222> LOCATION: 14
<223> OTHER INFORMATION: Xaa = D-Trp
<220> FEATURE:
<221> NAME/KEY: MOD_RES
<222> LOCATION: 18
<223> OTHER INFORMATION: Xaa = Threoninol

<400> SEQUENCE: 47

Lys Lys Xaa Lys Xaa Lys Lys Xaa Lys Xaa Xaa Cys Phe Xaa Lys Thr
 1               5                  10                  15

Cys Xaa

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = 2H, 2H, 3H 3H-perfluoroheptanoic acid
<220> FEATURE:
```

```
<221> NAME/KEY: VARIANT
<222> LOCATION: 3
<223> OTHER INFORMATION: Xaa = D-Lys
<220> FEATURE:
<221> NAME/KEY: MOD_RES
<222> LOCATION: 5
<223> OTHER INFORMATION: Xaa = 8-aminocaprylic acid
<220> FEATURE:
<221> NAME/KEY: MOD_RES
<222> LOCATION: 8
<223> OTHER INFORMATION: Xaa = Lys-palm
<220> FEATURE:
<221> NAME/KEY: MOD_RES
<222> LOCATION: 10
<223> OTHER INFORMATION: Xaa = aminohexanoic acid
<220> FEATURE:
<221> NAME/KEY: VARIANT
<222> LOCATION: 11
<223> OTHER INFORMATION: Xaa = D-Phe
<220> FEATURE:
<221> NAME/KEY: VARIANT
<222> LOCATION: 14
<223> OTHER INFORMATION: Xaa = D-Trp
<220> FEATURE:
<221> NAME/KEY: MOD_RES
<222> LOCATION: 18
<223> OTHER INFORMATION: Xaa = Threoninol

<400> SEQUENCE: 48

Xaa Lys Xaa Lys Xaa Lys Lys Xaa Lys Xaa Xaa Cys Phe Xaa Lys Thr
 1               5                  10                  15

Cys Xaa

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 15
<223> OTHER INFORMATION: Xaa = Lys-palm
<220> FEATURE:
<221> NAME/KEY: MOD_RES
<222> LOCATION: 16
<223> OTHER INFORMATION: Amidation at the C-terminus

<400> SEQUENCE: 49

Trp Thr Leu Asn Ser Ala Gly Tyr Leu Leu Gly Pro Lys Lys Xaa Lys
 1               5                  10                  15

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: VARIANT
<222> LOCATION: 14, 15, 17
<223> OTHER INFORMATION: Xaa = D-Lys
<220> FEATURE:
<221> NAME/KEY: MOD_RES
<222> LOCATION: 16
<223> OTHER INFORMATION: Xaa = Lys-palm

<400> SEQUENCE: 50
```

```
Xaa Trp Thr Leu Asn Ser Ala Gly Tyr Leu Leu Gly Pro Xaa Xaa Xaa
1               5                   10                  15

Xaa

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
<221> NAME/KEY: MOD_RES
<222> LOCATION: 17
<223> OTHER INFORMATION: Amidation at the C-terminus

<400> SEQUENCE: 51

Xaa Trp Thr Leu Asn Ser Ala Gly Tyr Leu Leu Gly Pro Arg Arg Xaa
1               5                   10                  15

Arg

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
<221> NAME/KEY: MOD_RES
<222> LOCATION: 17
<223> OTHER INFORMATION: Amidation at the C-terminus

<400> SEQUENCE: 52

Xaa Trp Thr Leu Asn Ser Ala Gly Tyr Leu Leu Gly Pro His His Xaa
1               5                   10                  15

His

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
```

```
<221> NAME/KEY: MOD_RES
<222> LOCATION: 17
<223> OTHER INFORMATION: Amidation at the C-terminus

<400> SEQUENCE: 53

Xaa Trp Thr Leu Asn Ser Ala Gly Tyr Leu Leu Lys Lys Lys Lys Xaa
1               5                   10                  15
Lys

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm
<220> FEATURE:
<221> NAME/KEY: MOD_RES
<222> LOCATION: 15
<223> OTHER INFORMATION: Amidation at the C-terminus

<400> SEQUENCE: 54

Xaa Trp Thr Leu Asn Ser Ala Gly Tyr Leu Leu Lys Lys Xaa Lys
1               5                   10                  15

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = aminohexanoic acid

<400> SEQUENCE: 55

Xaa Gly Gly Trp Ala Gly Gly Asp Ala Ser Gly Glu
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 56

Xaa Trp Thr Leu Asn Ser Ala Gly Tyr Leu Leu Gly Pro Lys Lys Xaa
1               5                   10                  15
Lys
```

```
<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 15
<223> OTHER INFORMATION: Xaa = Lys-palm

<400> SEQUENCE: 57

Trp Thr Leu Asn Ser Ala Gly Tyr Leu Leu Gly Pro Lys Lys Xaa Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: VARIANT
<222> LOCATION: 1, 2, 3
<223> OTHER INFORMATION: Xaa = D-Lys
<220> FEATURE:
<221> NAME/KEY: MOD_RES
<222> LOCATION: 4
<223> OTHER INFORMATION: Xaa = Lys-palm

<400> SEQUENCE: 58

Xaa Xaa Xaa Xaa Gly Gly Trp Ala Gly Gly Asp Ala Ser Gly Glu
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 59

Xaa Trp Thr Leu Asn Ser Ala Gly Tyr Leu Leu Gly Pro Arg Arg Xaa
1               5                   10                  15

Arg

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
```

```
<223> OTHER INFORMATION: Xaa = Lys-palm

<400> SEQUENCE: 60

Xaa Trp Thr Leu Asn Ser Ala Gly Tyr Leu Leu Lys Lys Lys Lys Xaa
 1               5                  10                  15

Lys

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly

<400> SEQUENCE: 61

Xaa Trp Thr Leu Asn Ser Ala Gly Tyr Leu Leu Gly Pro Lys Lys Lys
 1               5                  10                  15

Lys

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm

<400> SEQUENCE: 62

Xaa Trp Thr Leu Asn Ser Ala Gly Tyr Leu Leu Lys Lys Xaa Lys
 1               5                  10                  15

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 12
<223> OTHER INFORMATION: Xaa = Lys-palm

<400> SEQUENCE: 63

Xaa Trp Thr Leu Asn Ser Ala Gly Tyr Lys Lys Xaa Lys
 1               5                  10

<210> SEQ ID NO 64
<211> LENGTH: 18
<212> TYPE: PRT
<213> ORGANISM: Artificial Sequence
<220> FEATURE:
```

```
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = aminohexanoic acid
<220> FEATURE:
<221> NAME/KEY: MOD_RES
<222> LOCATION: 17
<223> OTHER INFORMATION: Xaa = Lys-palm

<400> SEQUENCE: 64

Xaa Trp Thr Leu Asn Ser Ala Gly Tyr Leu Leu Gly Pro Xaa Lys Lys
 1               5                  10                  15

Xaa Lys

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = aminohexanoic acid
<220> FEATURE:
<221> NAME/KEY: MOD_RES
<222> LOCATION: 13
<223> OTHER INFORMATION: Xaa = Lys-palm

<400> SEQUENCE: 65

Xaa Trp Thr Leu Asn Ser Ala Gly Tyr Xaa Lys Lys Xaa Lys
 1               5                  10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 12
<223> OTHER INFORMATION: Xaa = Lys-palm

<400> SEQUENCE: 66

Xaa Trp Thr Leu Asn Ser Ala Gly Tyr Lys Lys Xaa Lys
 1               5                  10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
```

```
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = aminohexanoic acid
<220> FEATURE:
<221> NAME/KEY: MOD_RES
<222> LOCATION: 13
<223> OTHER INFORMATION: Xaa = Lys-palm

<400> SEQUENCE: 67

Xaa Trp Thr Leu Asn Ser Ala Gly Tyr Xaa Lys Lys Xaa Lys
 1               5                  10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 68

Xaa Trp Thr Leu Asn Ser Ala Gly Tyr Leu Leu Gly Pro His Ala Xaa
 1               5                  10                  15

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: VARIANT
<222> LOCATION: 14, 15, 17
<223> OTHER INFORMATION: Xaa = D-Lys
<220> FEATURE:
<221> NAME/KEY: MOD_RES
<222> LOCATION: 16
<223> OTHER INFORMATION: Xaa = Lys-palm

<400> SEQUENCE: 69

Xaa Trp Thr Leu Asn Ser Ala Gly Tyr Leu Leu Gly Pro Xaa Xaa Xaa
 1               5                  10                  15

Xaa

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
```

```
<220> FEATURE:
<221> NAME/KEY: MOD_RES
<222> LOCATION: 16
<223> OTHER INFORMATION: Xaa = Lys-palm

<400> SEQUENCE: 70

Xaa Trp Thr Leu Asn Ser Ala Gly Tyr Leu Leu Gly Pro Arg Arg Xaa
 1               5                  10                  15

Arg

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 71

Xaa Trp Thr Leu Asn Ser Ala Gly Tyr Leu Leu Lys Lys Lys Lys Xaa
 1               5                  10                  15

Lys

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm

<400> SEQUENCE: 72

Xaa Trp Thr Leu Asn Ser Ala Gly Tyr Leu Leu Lys Lys Xaa Lys
 1               5                  10                  15

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14, 15, 17
<223> OTHER INFORMATION: Xaa = Orn
<220> FEATURE:
<221> NAME/KEY: MOD_RES
<222> LOCATION: 16
<223> OTHER INFORMATION: Xaa = Lys-palm
```

-continued

```
<400> SEQUENCE: 73

Xaa Trp Thr Leu Asn Ser Ala Gly Tyr Leu Leu Gly Pro Xaa Xaa Xaa
1               5                   10                  15

Xaa

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14, 15, 17
<223> OTHER INFORMATION: Xaa = Dbu
<220> FEATURE:
<221> NAME/KEY: MOD_RES
<222> LOCATION: 16
<223> OTHER INFORMATION: Xaa = Lys-palm

<400> SEQUENCE: 74

Xaa Trp Thr Leu Asn Ser Ala Gly Tyr Leu Leu Gly Pro Xaa Xaa Xaa
1               5                   10                  15

Xaa

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 13, 14, 16
<223> OTHER INFORMATION: Xaa = beta-homo-lysine
<220> FEATURE:
<221> NAME/KEY: MOD_RES
<222> LOCATION: 15
<223> OTHER INFORMATION: Xaa = Lys-palm

<400> SEQUENCE: 75

Xaa Trp Thr Leu Asn Ser Ala Gly Tyr Leu Leu Gly Xaa Xaa Xaa Xaa
1               5                   10                  15

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 76
```

```
Xaa Trp Thr Leu Asn Ser Ala Gly Tyr Leu Leu Gly Pro His His Xaa
 1               5                  10                  15

His

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 14
<223> OTHER INFORMATION: Xaa = Lys-palm

<400> SEQUENCE: 77

Xaa Trp Thr Leu Asn Ser Ala Gly Tyr Leu Leu Gly Pro Xaa Lys Lys
 1               5                  10                  15

Lys

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 15
<223> OTHER INFORMATION: Xaa = Lys-palm

<400> SEQUENCE: 78

Xaa Trp Thr Leu Asn Ser Ala Gly Tyr Leu Leu Gly Pro Lys Xaa Lys
 1               5                  10                  15

Lys

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 17
<223> OTHER INFORMATION: Xaa = Lys-palm

<400> SEQUENCE: 79

Xaa Trp Thr Leu Asn Ser Ala Gly Tyr Leu Leu Gly Pro Lys Lys Lys
 1               5                  10                  15

Xaa
```

```
<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = Spermine-N4 succinic acid
<220> FEATURE:
<221> NAME/KEY: MOD_RES
<222> LOCATION: 11
<223> OTHER INFORMATION: Xaa = Lys-palm

<400> SEQUENCE: 80

Xaa Trp Thr Leu Asn Ser Ala Gly Tyr Xaa Xaa
 1               5                  10

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm
<220> FEATURE:
<221> NAME/KEY: MOD_RES
<222> LOCATION: 17
<223> OTHER INFORMATION: Xaa = Spermine-N4 succinic acid

<400> SEQUENCE: 81

Xaa Trp Thr Leu Asn Ser Ala Gly Tyr Leu Leu Gly Pro Lys Lys Xaa
 1               5                  10                  15

Xaa

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Glu-spermine

<400> SEQUENCE: 82

Xaa Trp Thr Leu Asn Ser Ala Gly Tyr Leu Leu Gly Pro Lys Lys Xaa
 1               5                  10                  15

Lys

<210> SEQ ID NO 83
```

```
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-spermine-palm

<400> SEQUENCE: 83

Xaa Trp Thr Leu Asn Ser Ala Gly Tyr Leu Leu Gly Pro Lys Lys Xaa
 1               5                  10                  15

Lys

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Tetradecanoic acid

<400> SEQUENCE: 84

Xaa Trp Thr Leu Asn Ser Ala Gly Tyr Leu Leu Gly Pro Lys Lys Xaa
 1               5                  10                  15

Lys

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Nle

<400> SEQUENCE: 85

Xaa Trp Thr Leu Asn Ser Ala Gly Tyr Leu Leu Gly Pro Lys Lys Xaa
 1               5                  10                  15

Lys

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
```

```
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = L-Ser-alpha-mannose

<400> SEQUENCE: 86

Xaa Trp Thr Leu Asn Ser Ala Gly Tyr Leu Leu Gly Pro Lys Lys Xaa
 1               5                  10                  15

Lys

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = L-Ser-beta-melibose

<400> SEQUENCE: 87

Xaa Trp Thr Leu Asn Ser Ala Gly Tyr Leu Leu Gly Pro Lys Lys Xaa
 1               5                  10                  15

Lys

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 12
<223> OTHER INFORMATION: Xaa = 5-amino-3-oxapemtanoic acid
<220> FEATURE:
<221> NAME/KEY: MOD_RES
<222> LOCATION: 15
<223> OTHER INFORMATION: Xaa = Lys-palm

<400> SEQUENCE: 88

Xaa Trp Thr Leu Asn Ser Ala Gly Tyr Leu Leu Xaa Lys Lys Xaa Lys
 1               5                  10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
```

```
<222> LOCATION: 12
<223> OTHER INFORMATION: Xaa = 5-aminovaleric acid
<220> FEATURE:
<221> NAME/KEY: MOD_RES
<222> LOCATION: 15
<223> OTHER INFORMATION: Xaa = Lys-palm

<400> SEQUENCE: 89

Xaa Trp Thr Leu Asn Ser Ala Gly Tyr Leu Leu Xaa Lys Lys Xaa Lys
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 11
<223> OTHER INFORMATION: Xaa = 8-amino-3, 6-dioxaoctanoic acid
<220> FEATURE:
<221> NAME/KEY: MOD_RES
<222> LOCATION: 14
<223> OTHER INFORMATION: Xaa = Lys-palm

<400> SEQUENCE: 90

Xaa Trp Thr Leu Asn Ser Ala Gly Tyr Leu Xaa Lys Lys Xaa Lys
 1               5                  10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 11
<223> OTHER INFORMATION: Xaa = 8-amino octanoic acid
<220> FEATURE:
<221> NAME/KEY: MOD_RES
<222> LOCATION: 14
<223> OTHER INFORMATION: Xaa = Lys-palm

<400> SEQUENCE: 91

Xaa Trp Thr Leu Asn Ser Ala Gly Tyr Leu Xaa Lys Lys Xaa Lys
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
```

```
<223> OTHER INFORMATION: Xaa = 5-amino-3-oxapemtanoic acid
<220> FEATURE:
<221> NAME/KEY: MOD_RES
<222> LOCATION: 11
<223> OTHER INFORMATION: Xaa = 5-aminovaleric acid
<220> FEATURE:
<221> NAME/KEY: MOD_RES
<222> LOCATION: 14
<223> OTHER INFORMATION: Xaa = Lys-palm

<400> SEQUENCE: 92

Xaa Trp Thr Leu Asn Ser Ala Gly Tyr Xaa Xaa Lys Lys Xaa Lys
1               5                   10                  15

<210> SEQ ID NO 93
<211> LENGTH: 30
<212> TYPE: PRT
<213> ORGANISM: Homo sapien

<400> SEQUENCE: 93

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 94
<211> LENGTH: 29
<212> TYPE: PRT
<213> ORGANISM: Murinae
<220> FEATURE:
<221> NAME/KEY: AMIDATION
<222> LOCATION: 29
<223> OTHER INFORMATION: Amidation at the C-terminus

<400> SEQUENCE: 94

Gly Trp Thr Leu Asn Ser Ala Gly Tyr Leu Leu Gly Pro His Ala Ile
1               5                   10                  15

Asp Asn His Arg Ser Phe Ser Asp Lys His Gly Leu Thr
            20                  25

<210> SEQ ID NO 95
<211> LENGTH: 29
<212> TYPE: PRT
<213> ORGANISM: Sus scrofa

<400> SEQUENCE: 95

Gly Trp Thr Leu Asn Ser Ala Gly Tyr Leu Leu Gly Pro His Ala Ile
1               5                   10                  15

Asp Asn His Arg Ser Phe His Asp Lys Tyr Gly Leu Ala
            20                  25

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 96

Gly Trp Thr Leu Asn Ser Ala Gly Tyr Leu Leu Gly Pro His Ala Ile
1               5                   10                  15

<210> SEQ ID NO 97
<211> LENGTH: 14
<212> TYPE: PRT
```

```
<213> ORGANISM: Artificial Sequence
<220> FEATURE:
<223> OTHER INFORMATION: Description of Artificial Sequence = Synthetic
      Construct

<400> SEQUENCE: 97

Gly Trp Thr Leu Asn Ser Ala Gly Tyr Leu Leu Gly Pro His
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 98

Gly Trp Thr Leu Asn Ser Ala Gly Tyr Leu Leu Gly
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 99

Gly Trp Thr Leu Asn Ser Ala Gly Tyr Leu
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 100

Gly Trp Thr Leu Asn Ser Ala Gly Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: VARIANT
<222> LOCATION: 1
<223> OTHER INFORMATION: Xaa = D-Phe
<220> FEATURE:
<221> NAME/KEY: VARIANT
<222> LOCATION: 4
<223> OTHER INFORMATION: Xaa = D-Trp
<220> FEATURE:
<221> NAME/KEY: AMIDATION
<222> LOCATION: 8
<223> OTHER INFORMATION: Amidation at the C terminus

<400> SEQUENCE: 101

Xaa Cys Phe Xaa Lys Thr Cys Thr
1               5
```

```
<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 102

Trp Ala Gly Gly Asp Phe Ser Gly Glu
1               5

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 103

Tyr Gly Gly Phe Leu Arg Arg Ile Arg Pro Lys Leu Lys Trp Asp Asn
1               5                   10                  15

Gln

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: AMIDATION
<222> LOCATION: 24
<223> OTHER INFORMATION: Amidation at the C terminus

<400> SEQUENCE: 104

Pro Ala Glu Asp Leu Ala Arg Tyr Tyr Ser Ala Leu Arg Ala Tyr Ile
1               5                   10                  15

Asn Leu Ile Thr Arg Gln Arg Tyr
            20

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: VARIANT
<222> LOCATION: 5
<223> OTHER INFORMATION: Xaa = any amino acid

<400> SEQUENCE: 105

Lys Lys Xaa Lys Xaa
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence = Synthetic
```

-continued

```
                    Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: VARIANT
<222> LOCATION: 6
<223> OTHER INFORMATION: Xaa = any amino acid

<400> SEQUENCE: 106

Lys Lys Xaa Lys Gly Xaa
 1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence = Synthetic
                    Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: VARIANT
<222> LOCATION: 6
<223> OTHER INFORMATION: Xaa = any amino acid

<400> SEQUENCE: 107

Lys Lys Xaa Lys Xaa Xaa
 1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence = Synthetic
                    Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: VARIANT
<222> LOCATION: 7
<223> OTHER INFORMATION: Xaa = any amino acid

<400> SEQUENCE: 108

Lys Lys Xaa Lys Xaa Gly Xaa
 1               5

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence = Synthetic
                    Construct
<220> FEATURE:
<221> NAME/KEY: MOD_RES
<222> LOCATION: 15
<223> OTHER INFORMATION: Xaa = Lys-palm
```

```
<220> FEATURE:
<221> NAME/KEY: AMIDATION
<222> LOCATION: 16
<223> OTHER INFORMATION: Amidation at the C terminus

<400> SEQUENCE: 109

Tyr Gly Gly Phe Leu Arg Arg Ile Arg Pro Lys Leu Lys Lys Xaa Lys
1               5                   10                  15

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 16
<223> OTHER INFORMATION: Xaa = Lys-palm
<220> FEATURE:
<221> NAME/KEY: AMIDATION
<222> LOCATION: 17
<223> OTHER INFORMATION: Amidation at the C terminus

<400> SEQUENCE: 110

Tyr Gly Gly Phe Leu Arg Arg Ile Arg Pro Lys Leu Lys Lys Lys Xaa
1               5                   10                  15

Lys

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 14
<223> OTHER INFORMATION: Xaa = Lys-palm
<220> FEATURE:
<221> NAME/KEY: AMIDATION
<222> LOCATION: 15
<223> OTHER INFORMATION: Amidation at the C terminus

<400> SEQUENCE: 111

Tyr Gly Gly Phe Leu Arg Arg Ile Arg Pro Lys Lys Lys Xaa Lys
1               5                   10                  15

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 14
<223> OTHER INFORMATION: Xaa = Aminohexanoic acid
<220> FEATURE:
<221> NAME/KEY: MOD_RES
<222> LOCATION: 17
<223> OTHER INFORMATION: Xaa = Lys-palm
<220> FEATURE:
<221> NAME/KEY: AMIDATION
<222> LOCATION: 18
<223> OTHER INFORMATION: Amidation at the C terminus

<400> SEQUENCE: 112
```

Tyr Gly Gly Phe Leu Arg Arg Ile Arg Pro Lys Leu Lys Xaa Lys Lys
1               5                   10                  15

Xaa Lys

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 4
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: AMIDATION
<222> LOCATION: 17
<223> OTHER INFORMATION: Amidation at the C terminus

<400> SEQUENCE: 113

Lys Lys Lys Xaa Xaa Arg Ala Tyr Ile Asn Leu Ile Thr Arg Gln Arg
1               5                   10                  15

Tyr

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: AMIDATION
<222> LOCATION: 17
<223> OTHER INFORMATION: Amidation at the C terminus

<400> SEQUENCE: 114

Lys Lys Xaa Lys Xaa Arg Ala Tyr Ile Asn Leu Ile Thr Arg Gln Arg
1               5                   10                  15

Tyr

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = any amino acid

<400> SEQUENCE: 115

```
Lys Lys Xaa Lys Xaa
 1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 6
<223> OTHER INFORMATION: Xaa = any amino acid

<400> SEQUENCE: 116

Lys Lys Xaa Lys Gly Xaa
 1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: MOD_RES
<222> LOCATION: 6
<223> OTHER INFORMATION: Xaa = any amino acid

<400> SEQUENCE: 117

Lys Lys Xaa Lys Xaa Xaa
 1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm
<220> FEATURE:
<221> NAME/KEY: MOD_RES
<222> LOCATION: 5
<223> OTHER INFORMATION: Xaa = Aminohexanoic acid
<220> FEATURE:
<221> NAME/KEY: MOD_RES
<222> LOCATION: 7
<223> OTHER INFORMATION: Xaa = any amino acid

<400> SEQUENCE: 118

Lys Lys Xaa Lys Xaa Gly Xaa
 1               5
```

-continued

```
<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: VARIANT
<222> LOCATION: 10, 11, 13
<223> OTHER INFORMATION: Xaa = D-Lys
<220> FEATURE:
<221> NAME/KEY: MOD_RES
<222> LOCATION: 12
<223> OTHER INFORMATION: Xaa = Lys-palm

<400> SEQUENCE: 119

Xaa Trp Thr Leu Asn Ser Ala Gly Tyr Xaa Xaa Xaa Xaa
 1               5                  10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = Aminohexanoic acid
<220> FEATURE:
<221> NAME/KEY: VARIANT
<222> LOCATION: 11, 12, 13, 14
<223> OTHER INFORMATION: Xaa = D-Lys

<400> SEQUENCE: 120

Xaa Trp Thr Leu Asn Ser Ala Gly Tyr Xaa Xaa Xaa Xaa Xaa
 1               5                  10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = 7-Ahp
<220> FEATURE:
<221> NAME/KEY: VARIANT
<222> LOCATION: 11, 12, 14
<223> OTHER INFORMATION: Xaa = D-Lys
<220> FEATURE:
<221> NAME/KEY: MOD_RES
<222> LOCATION: 13
<223> OTHER INFORMATION: Xaa = Lys-palm

<400> SEQUENCE: 121

Xaa Trp Thr Leu Asn Ser Ala Gly Tyr Xaa Xaa Xaa Xaa Xaa
```

```
<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 10
<223> OTHER INFORMATION: Xaa = 3,5-dibromo-Tyr
<220> FEATURE:
<221> NAME/KEY: MOD_RES
<222> LOCATION: 17
<223> OTHER INFORMATION: Xaa = Lys-palm

<400> SEQUENCE: 122

Xaa Trp Thr Leu Asn Ser Ala Gly Tyr Xaa Leu Leu Gly Pro Lys Lys
1               5                   10                  15

Xaa Lys

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 123

Xaa Trp Thr Leu Asn Ser Ala Gly Tyr Leu Leu Gly Pro His His Xaa
1               5                   10                  15

Lys

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = 4-methyltrityl

<400> SEQUENCE: 124

Xaa Trp Thr Leu Asn Ser Ala Gly Tyr Leu Leu Gly Pro Lys Lys Xaa
1               5                   10                  15

Lys
```

```
<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-Biotin-aminocaproyl

<400> SEQUENCE: 125

Xaa Trp Thr Leu Asn Ser Ala Gly Tyr Leu Leu Gly Pro Lys Lys Xaa
 1               5                  10                  15
Lys

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-sterol

<400> SEQUENCE: 126

Xaa Trp Thr Leu Asn Ser Ala Gly Tyr Leu Leu Gly Pro Lys Lys Xaa
 1               5                  10                  15
Lys

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-decanoyl

<400> SEQUENCE: 127

Xaa Trp Thr Leu Asn Ser Ala Gly Tyr Leu Leu Gly Pro Lys Lys Xaa
 1               5                  10                  15
Lys

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
```

```
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-octanoyl

<400> SEQUENCE: 128

Xaa Trp Thr Leu Asn Ser Ala Gly Tyr Leu Leu Gly Pro Lys Lys Xaa
 1               5                  10                  15

Lys

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-linoyl

<400> SEQUENCE: 129

Xaa Trp Thr Leu Asn Ser Ala Gly Tyr Leu Leu Gly Pro Lys Lys Xaa
 1               5                  10                  15

Lys

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Ser-melbiose

<400> SEQUENCE: 130

Xaa Trp Thr Leu Asn Ser Ala Gly Tyr Leu Leu Gly Pro Lys Lys Xaa
 1               5                  10                  15

Lys

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
```

```
<223> OTHER INFORMATION: Xaa = Lys-adamentoyl

<400> SEQUENCE: 131

Xaa Trp Thr Leu Asn Ser Ala Gly Tyr Leu Leu Gly Pro Lys Lys Xaa
 1               5                  10                  15

Lys

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Glu(Beta-Lac-PEG3-amine)

<400> SEQUENCE: 132

Xaa Trp Thr Leu Asn Ser Ala Gly Tyr Leu Leu Gly Pro Lys Lys Xaa
 1               5                  10                  15

Lys

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 133

Xaa Trp Thr Leu Thr Ser Ala Gly Tyr Leu Leu Gly Pro Lys Lys Xaa
 1               5                  10                  15

Lys

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 134

Xaa Trp Thr Leu Leu Ser Ala Gly Tyr Leu Leu Gly Pro Lys Lys Xaa
 1               5                  10                  15
```

Lys

```
<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = MeGly
<220> FEATURE:
<221> NAME/KEY: MOD_RES
<222> LOCATION: 16
<223> OTHER INFORMATION: Xaa = Lys-palm

<400> SEQUENCE: 135

Xaa Trp Thr Leu Asp Ser Ala Gly Tyr Leu Leu Gly Pro Lys Lys Xaa
 1               5                  10                  15
Lys

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = Aminohexanoic acid

<400> SEQUENCE: 136

Xaa Gly Gly Trp Ala Gly Gly Asp Ala Ser Gly Glu
 1               5                  10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = palmitic acid

<400> SEQUENCE: 137

Xaa Gly Gly Trp Ala Gly Gly Asp Ala Ser Gly Glu
 1               5                  10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = Lys-palm

<400> SEQUENCE: 138

Xaa Gly Gly Trp Ala Gly Gly Asp Ala Ser Gly Glu
 1               5                  10
```

```
<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 4
<223> OTHER INFORMATION: Xaa = Lys-palm

<400> SEQUENCE: 139

Lys Lys Lys Xaa Gly Gly Trp Ala Gly Gly Asp Ala Ser Gly Glu
 1               5                  10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 3
<223> OTHER INFORMATION: Xaa = Lys-palm

<400> SEQUENCE: 140

Lys Lys Xaa Lys Gly Gly Trp Ala Gly Gly Asp Ala Ser Gly Glu
 1               5                  10                  15

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence = Synthetic
      Construct

<400> SEQUENCE: 141

Lys Lys Lys Gly Gly Trp Ala Gly Gly Asp Ala Ser Gly Glu
 1               5                  10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence = Synthetic
      Construct
<220> FEATURE:
<221> NAME/KEY: MOD_RES
<222> LOCATION: 1
<223> OTHER INFORMATION: Xaa = Aminohexanoic acid

<400> SEQUENCE: 142

Xaa Gly Gly Trp Ala Gly Gly Asp Phe Ser Gly Glu
 1               5                  10
```